(12) United States Patent
Fortier et al.

(10) Patent No.: US 8,801,752 B2
(45) Date of Patent: Aug. 12, 2014

(54) ARTICULATING SURGICAL DEVICE

(75) Inventors: Richard Fortier, Concord, MA (US); Andrew Ziegler, Arlington, MA (US); Amos Cruz, Wrentham, MA (US); Gene A. Stellon, Burlington, CT (US); Steve Evans, Westford, MA (US)

(73) Assignee: Covidien LP, Mansfield, MA (US)

( * ) Notice: Subject to any disclaimer, the term of this patent is extended or adjusted under 35 U.S.C. 154(b) by 810 days.

(21) Appl. No.: 12/511,614

(22) Filed: Jul. 29, 2009

(65) Prior Publication Data

US 2010/0030018 A1 Feb. 4, 2010

Related U.S. Application Data

(60) Provisional application No. 61/085,997, filed on Aug. 4, 2008.

(51) Int. Cl.
*A61B 17/00* (2006.01)

(52) U.S. Cl.
USPC .......................................................... 606/205

(58) Field of Classification Search
USPC ...................... 606/205–208, 1, 170, 174, 180; 451/344–359; 81/177.75, 177.85; 600/141–147
See application file for complete search history.

(56) References Cited

U.S. PATENT DOCUMENTS

| | | | |
|---|---|---|---|
| 2,028,635 A | 1/1936 | Wappler |
| 2,507,710 A | 5/1950 | Grosso |
| 2,790,437 A | 4/1957 | Moore |
| 3,557,780 A | 1/1971 | Sato |
| 3,858,577 A | 1/1975 | Bass et al. |
| 3,895,636 A | 7/1975 | Schmidt |
| 4,483,562 A | 11/1984 | Schoolman |
| 4,688,554 A | 8/1987 | Habib |
| 4,728,020 A | 3/1988 | Green et al. |
| 4,763,669 A | 8/1988 | Jaeger |
| 4,872,456 A | 10/1989 | Hasson |

(Continued)

FOREIGN PATENT DOCUMENTS

| | | |
|---|---|---|
| EP | 0095970 A2 | 12/1983 |
| EP | 0448284 A2 | 9/1991 |

(Continued)

OTHER PUBLICATIONS

Eureopean Search Report for EP 08 252797.9-2319 date of completion is Nov. 7, 2008 (6 pages).

(Continued)

*Primary Examiner* — Darwin Erezo
*Assistant Examiner* — Amy Shipley

(57) ABSTRACT

A surgical device for performing surgery generally includes a handle assembly, an elongate member extending from the handle assembly, an articulation mechanism operatively associated with the handle assembly, and an end effector. The elongate member has an articulating section and straight section. The articulating section is configured to articulate with respect to the straight section. The articulation mechanism is operatively associated with the handle assembly and the articulating section such that the articulating section articulates toward a first direction relative to the straight section upon movement of the handle assembly towards the first direction with respect to the straight section. The end effector is operatively coupled to the articulating section of the elongate member and includes first and second jaw members. The surgical device further includes a locking mechanism configured for fixing a relative position of first and second jaw members.

32 Claims, 37 Drawing Sheets

(56) References Cited

U.S. PATENT DOCUMENTS

| | | | |
|---|---|---|---|
| 4,880,015 A | 11/1989 | Nieman | |
| 4,944,093 A | 7/1990 | Falk | |
| 4,944,741 A | 7/1990 | Hasson | |
| 4,945,920 A | 8/1990 | Clossick | |
| 5,002,543 A | 3/1991 | Bradshasw et al. | |
| 5,042,707 A | 8/1991 | Taheri | |
| 5,209,747 A | 5/1993 | Knoepfler | |
| 5,271,381 A | 12/1993 | Ailinger et al. | |
| 5,273,026 A | 12/1993 | Wilk | |
| 5,275,608 A | 1/1994 | Forman et al. | |
| 5,290,299 A * | 3/1994 | Fain et al. | 606/142 |
| 5,314,424 A | 5/1994 | Nicholas | |
| 5,330,502 A | 7/1994 | Hassler et al. | |
| 5,344,428 A | 9/1994 | Griffiths | |
| 5,383,880 A | 1/1995 | Hooven | |
| 5,386,818 A | 2/1995 | Schneebaum et al. | |
| 5,395,367 A | 3/1995 | Wilk | |
| 5,405,344 A * | 4/1995 | Williamson et al. | 606/1 |
| 5,433,721 A | 7/1995 | Hooven et al. | |
| 5,441,494 A | 8/1995 | Ortiz | |
| 5,454,827 A | 10/1995 | Aust et al. | |
| 5,476,479 A * | 12/1995 | Green et al. | 606/205 |
| 5,501,654 A | 3/1996 | Failla et al. | |
| 5,511,564 A | 4/1996 | Wilk | |
| 5,520,678 A | 5/1996 | Heckele et al. | |
| 5,601,601 A * | 2/1997 | Tal et al. | 606/207 |
| 5,618,294 A | 4/1997 | Aust et al. | |
| 5,626,608 A * | 5/1997 | Cuny et al. | 606/205 |
| 5,643,294 A | 7/1997 | Tovey et al. | |
| 5,702,408 A | 12/1997 | Wales et al. | |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,868,785 A * | 2/1999 | Tal et al. | 606/207 |
| 5,873,817 A | 2/1999 | Kokish et al. | |
| 5,899,425 A | 5/1999 | Corey Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,938,678 A | 8/1999 | Zirps et al. | |
| 5,944,713 A | 8/1999 | Schuman | |
| 6,096,037 A * | 8/2000 | Mulier et al. | 606/49 |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,440,130 B1 * | 8/2002 | Mulier et al. | 606/49 |
| 6,443,952 B1 * | 9/2002 | Mulier et al. | 606/49 |
| 6,551,238 B2 | 4/2003 | Staud | |
| 6,623,424 B2 | 9/2003 | Hayakawa et al. | |
| 6,638,214 B2 | 10/2003 | Akiba | |
| 6,641,595 B1 * | 11/2003 | Moran et al. | 606/205 |
| 6,656,195 B2 | 12/2003 | Peters et al. | |
| 6,666,854 B1 * | 12/2003 | Lange | 606/1 |
| 6,752,756 B2 | 6/2004 | Lunsford et al. | |
| 6,761,717 B2 | 7/2004 | Bales et al. | |
| 6,773,434 B2 | 8/2004 | Ciarrocca | 606/51 |
| 6,858,028 B2 * | 2/2005 | Mulier et al. | 606/51 |
| 7,147,638 B2 * | 12/2006 | Chapman et al. | 606/51 |
| 7,147,650 B2 | 12/2006 | Lee | |
| 7,156,846 B2 * | 1/2007 | Dycus et al. | 606/51 |
| 7,160,299 B2 * | 1/2007 | Baily | 606/51 |
| 7,195,631 B2 * | 3/2007 | Dumbauld | 606/51 |
| 7,278,563 B1 | 10/2007 | Green | |
| 7,364,582 B2 | 4/2008 | Lee | |
| 7,655,007 B2 * | 2/2010 | Baily | 606/51 |
| 7,708,758 B2 * | 5/2010 | Lee et al. | 606/205 |
| 7,846,161 B2 * | 12/2010 | Dumbauld et al. | 606/51 |
| 8,287,449 B2 * | 10/2012 | Tanaka | 600/149 |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0045900 A1 | 3/2003 | Hahnen et al. | |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0149338 A1 | 8/2003 | Francois et al. | |
| 2003/0216618 A1 | 11/2003 | Arai | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0158268 A1 | 8/2004 | Danitz | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0107667 A1 | 5/2005 | Danitz et al. | |
| 2005/0228440 A1 | 10/2005 | Brock et al. | |
| 2005/0251112 A1 | 11/2005 | Danitz et al. | |
| 2005/0273084 A1 | 12/2005 | Hinman | |
| 2005/0273085 A1 | 12/2005 | Hinman et al. | |
| 2006/0069396 A1 | 3/2006 | Meade et al. | |
| 2006/0190034 A1 | 8/2006 | Nishizawa et al. | |
| 2007/0179524 A1 * | 8/2007 | Weber et al. | 606/205 |
| 2007/0221700 A1 * | 9/2007 | Ortiz et al. | 227/175.1 |
| 2007/0225562 A1 * | 9/2007 | Spivey et al. | 600/121 |
| 2007/0250113 A1 * | 10/2007 | Hegeman et al. | 606/207 |
| 2008/0033428 A1 * | 2/2008 | Artale et al. | 606/51 |
| 2008/0188868 A1 | 8/2008 | Weitzner et al. | |
| 2009/0131974 A1 * | 5/2009 | Pedersen et al. | 606/205 |
| 2010/0041945 A1 * | 2/2010 | Isbell, Jr. | 600/104 |
| 2010/0057121 A1 * | 3/2010 | Piskun et al. | 606/206 |
| 2011/0022052 A1 * | 1/2011 | Jorgensen | 606/83 |
| 2011/0144430 A1 * | 6/2011 | Spivey et al. | 600/106 |
| 2011/0163146 A1 * | 7/2011 | Ortiz et al. | 227/175.1 |
| 2011/0295242 A1 * | 12/2011 | Spivey et al. | 606/1 |
| 2012/0209254 A1 * | 8/2012 | Park et al. | 606/1 |
| 2013/0012931 A1 * | 1/2013 | Spivey et al. | 606/1 |
| 2013/0197556 A1 * | 8/2013 | Shelton et al. | 606/170 |

FOREIGN PATENT DOCUMENTS

| | | |
|---|---|---|
| EP | 0626604 A2 | 5/1994 |
| EP | 0427949 B1 | 6/1994 |
| EP | 1 813 203 A2 | 8/2007 |
| EP | 1 915 957 A2 | 4/2008 |
| EP | 1 915 966 A1 | 4/2008 |
| EP | 2 044 890 A1 | 4/2009 |
| GB | 2143920 | 2/1985 |
| WO | WO 90/05491 | 5/1990 |
| WO | WO 92/01414 | 2/1992 |
| WO | WO 94/17965 | 8/1994 |
| WO | WO 94/22377 A | 10/1994 |
| WO | WO 02/34147 A1 | 5/2002 |
| WO | WO 2006113216 | 10/2006 |
| WO | WO 2007/002545 A | 1/2007 |
| WO | WO 2008/042423 A2 | 4/2008 |

OTHER PUBLICATIONS

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

European Search Report for EP 11 25 0257 dated Jun. 15, 2011.

European Search Report for Appln. No. 09251932.1-2310 dated Dec. 23, 2009, 3 pages.

* cited by examiner

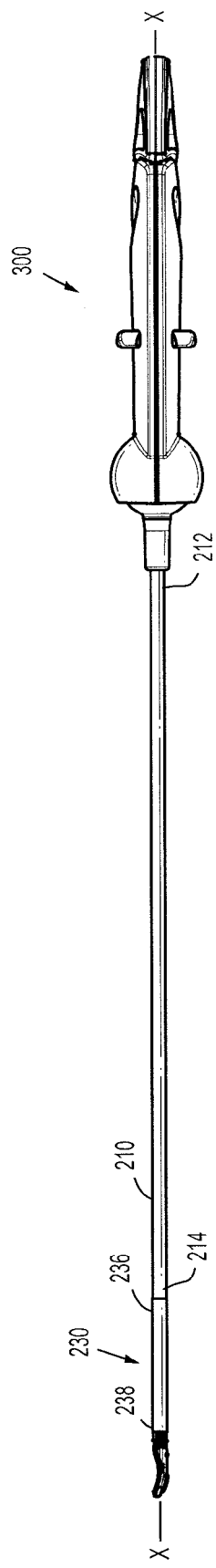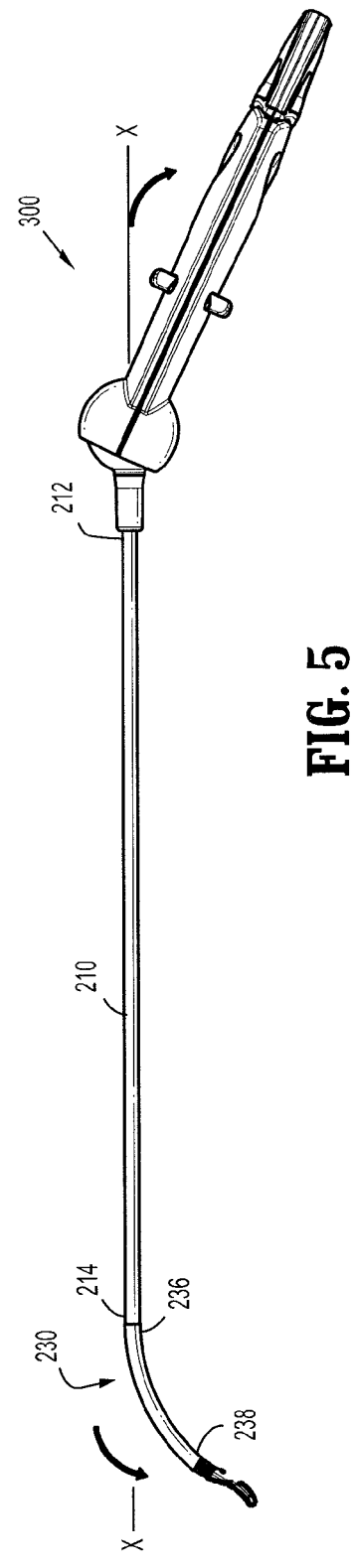
FIG. 4
FIG. 5

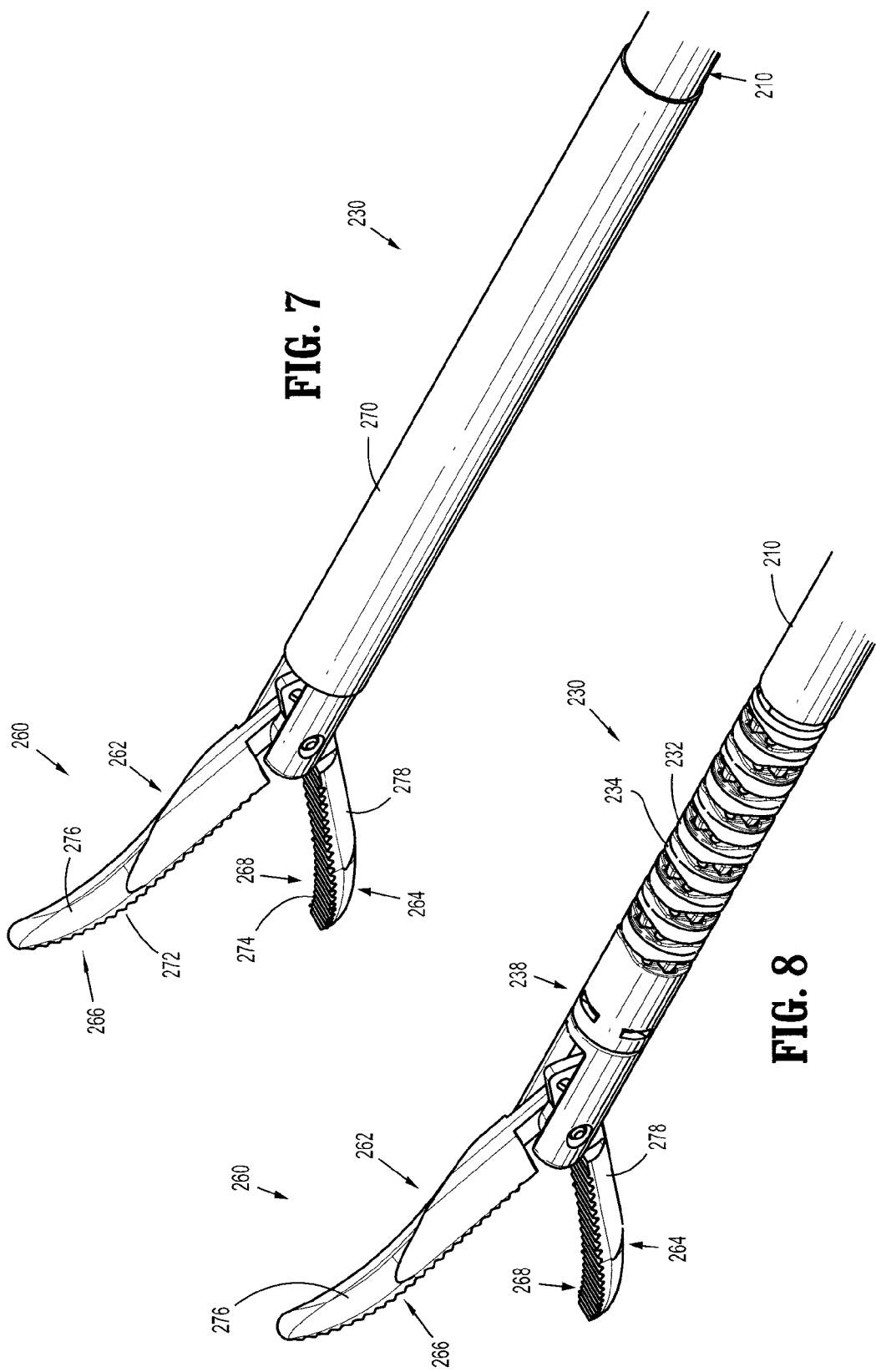

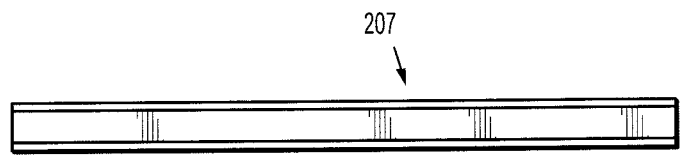
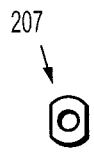
FIG. 10B  FIG. 10C
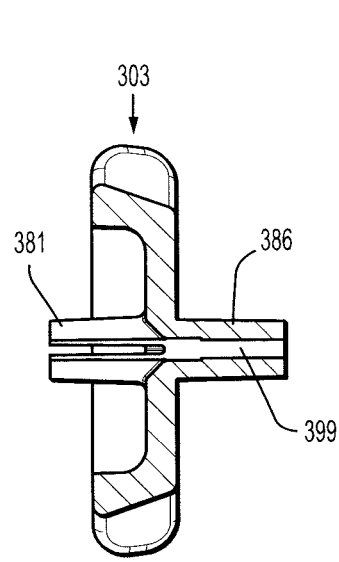
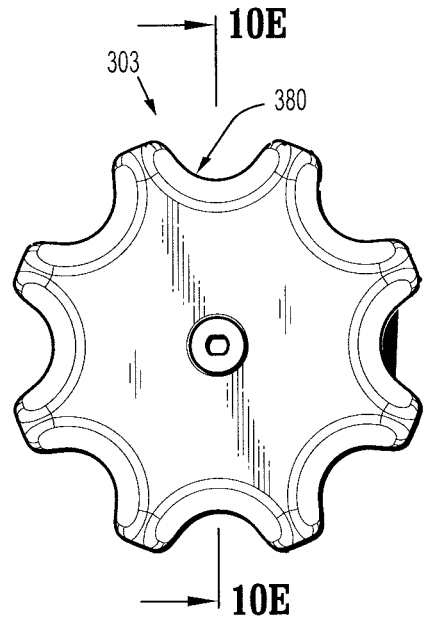
FIG. 10E  FIG. 10D

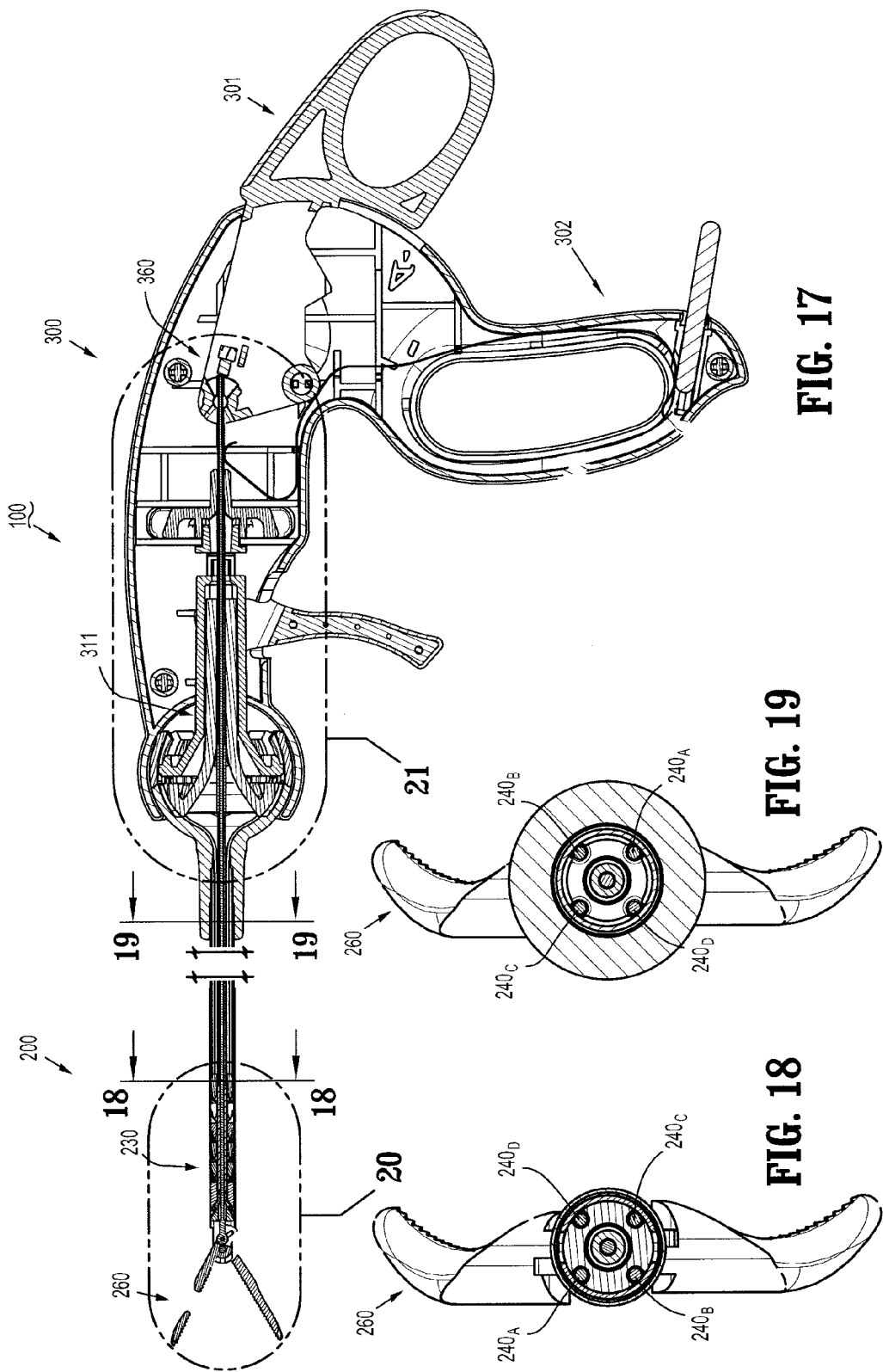

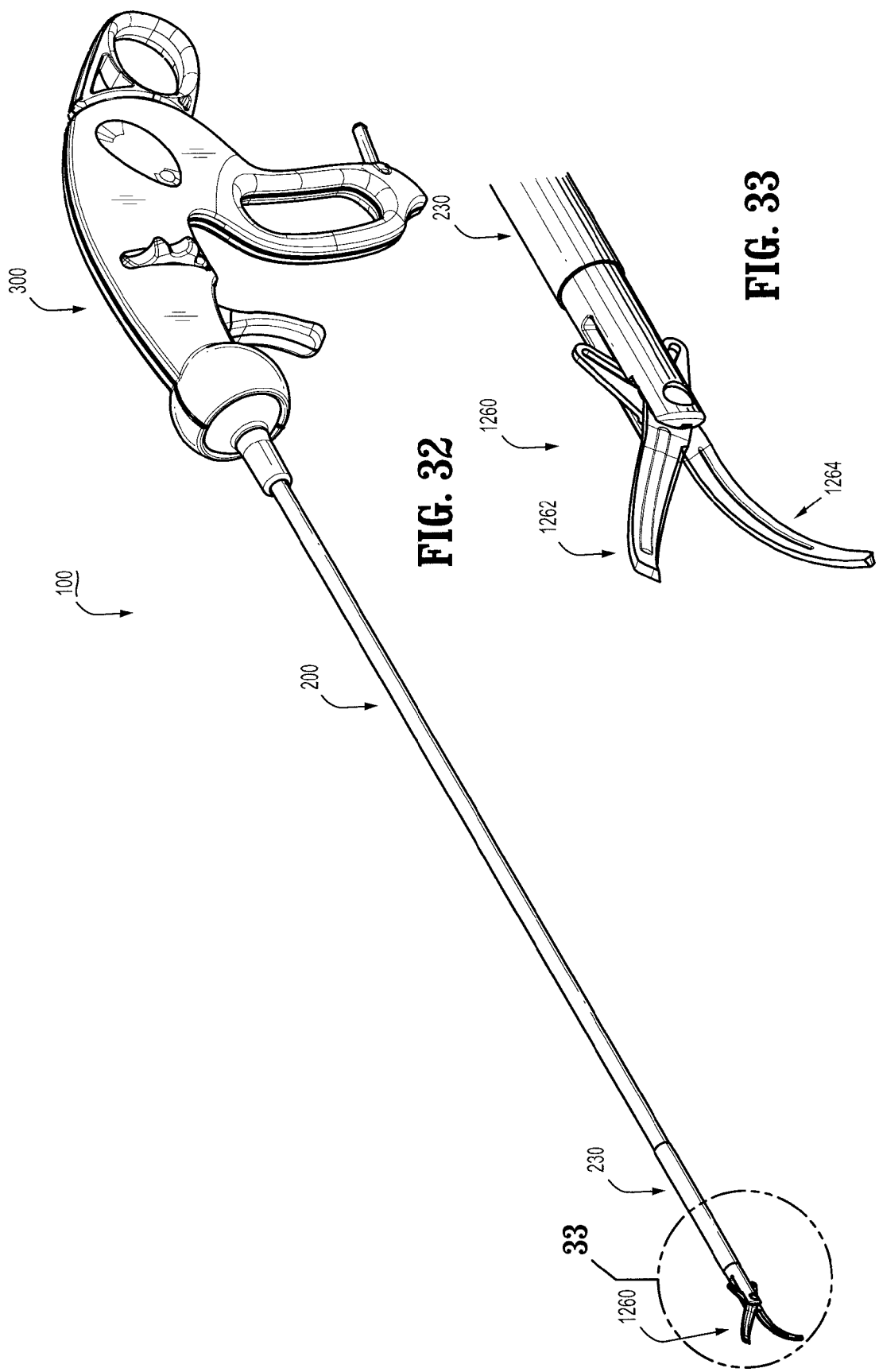

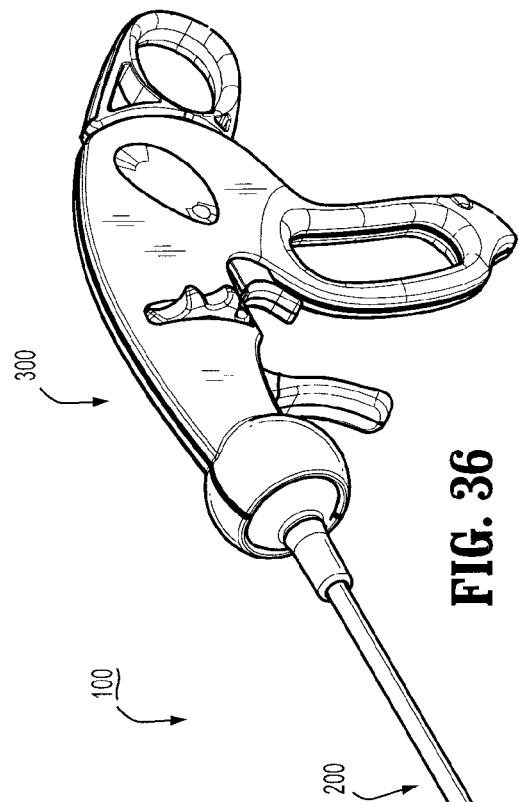
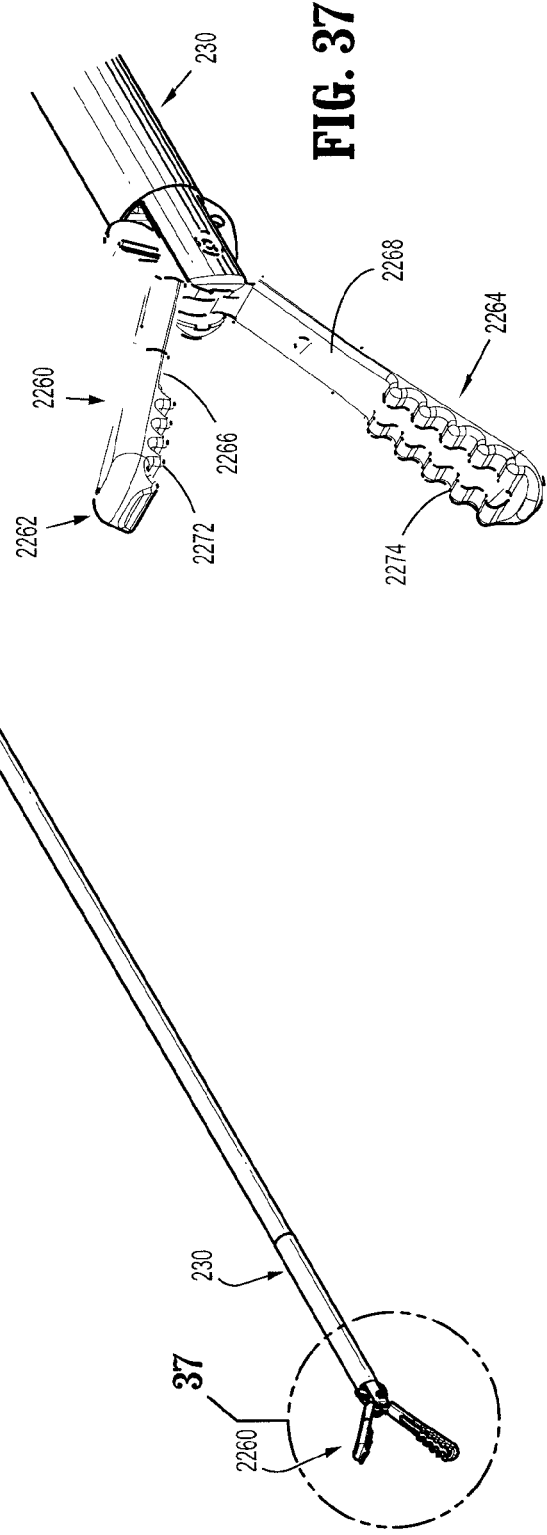

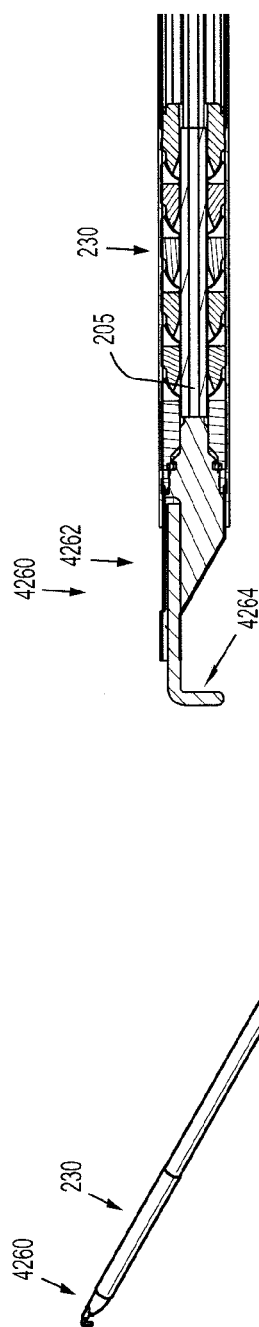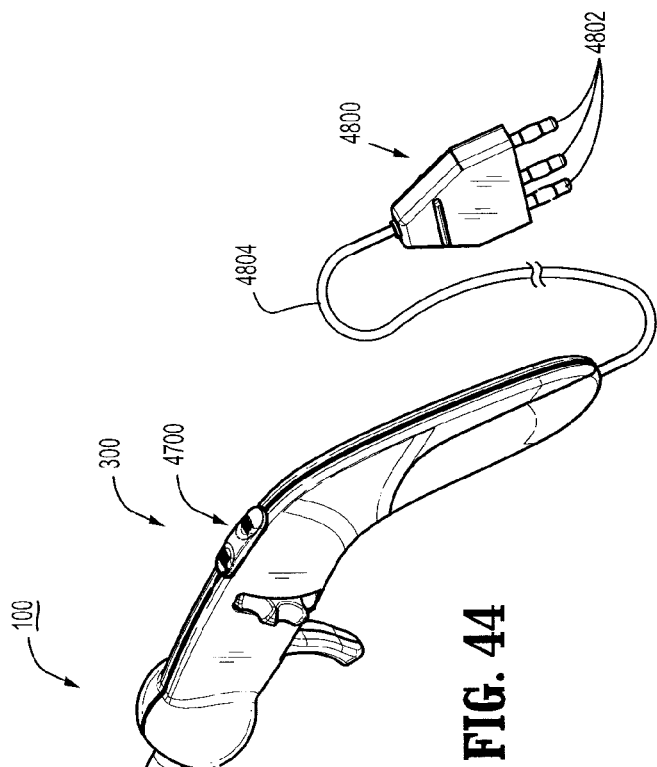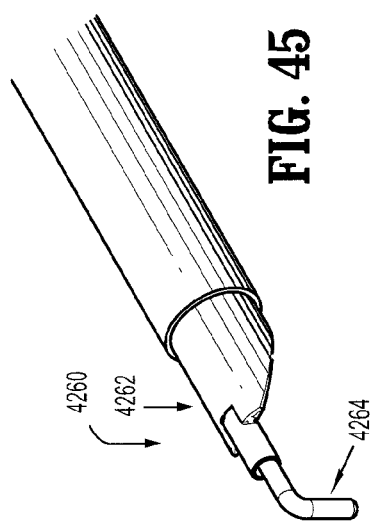
FIG. 46
FIG. 44
FIG. 45

ARTICULATING SURGICAL DEVICE

CROSS-REFERENCE TO RELATED APPLICATION

The present disclosure claims priority to, and the benefit of, U.S. Provisional Patent Application No. 61/085,997, filed on Aug. 4, 2008, the entire contents of which are hereby incorporated by reference.

BACKGROUND

1. Technical Field

The present disclosure relates to endoscopic surgical devices, and more particularly, to endoscopic surgical devices capable of multiple degrees of articulation.

2. Background of the Related Art

Endoscopic surgery is a minimally invasive technique for performing surgery intracorporeally without requiring a large incision. Typically, endoscopic surgery is conducted by inserting a number of ports through small incisions in the patient's skin to access a surgical site. One of the ports receives an endoscope, which is a video camera-like device. The surgeon views the surgical site via the endoscope and performs the surgery by inserting various surgical devices into the patient through the ports. During endoscopic surgery, the surgeon may introduce different surgical devices through the ports. For example, the surgeon may insert a hand operated endoscopic grasper, a dissector, shears, scissors and the like. This technique does not require "opening up" the patient, resulting in less invasive surgery than conventional procedures.

In an effort to reduce the number of incisions required, single incisions procedures and related surgical devices have been developed over the years. For instance, the surgeon may make one incision and maneuver a surgical device through the patient's body until it reaches the desired surgical site. However, it is often challenging to steer a surgical device through the complexities of the human anatomy. In light of this difficulty, a need exist for surgical devices capable of multitude degrees of operation and motion.

SUMMARY

The present disclosure relates to a surgical device capable of multiple degrees of articulation. This surgical device generally includes a handle assembly, an elongate member extending from the handle assembly, an articulation mechanism operatively associated with the handle assembly, and an end effector. The elongate member has an articulating section and straight section. The articulating section is configured to articulate with respect to the straight section. The articulation mechanism is operatively associated with the handle assembly and the articulating section such that the articulating section articulates toward a first direction relative to the straight section upon movement of the handle assembly towards the first direction with respect to the straight section. The end effector is operatively coupled to the articulating section of the elongate member and includes first and second jaw members. The first and second jaw members are configured to move relative to each other between an open position and an approximated position. The surgical device further includes a locking mechanism configured for fixing a relative position of first and second jaw members. The locking mechanism includes a first ratchet assembly and a second ratchet assembly positioned within the handle assembly. The first and second ratchet assemblies are moveable relative to each other between an engaged position to lock the relative position of the first and second jaw members and a disengaged position to unlock the relative position of the first and second jaw members.

BRIEF DESCRIPTION OF THE DRAWINGS

Embodiments of the presently disclosed surgical devices are described herein with reference to the accompanying drawings, wherein:

FIG. 4 is a top view of the surgical device of FIG. 1 with the articulating section in a straight position;

FIG. 5 is a top view of the surgical device of FIG. 1 with the articulating section in an articulated position;

FIG. 7 is a perspective sectional view of an end effector and the articulating section of the surgical device of FIG. 1, taken around section 7 of FIG. 1 and showing a sheath covering the articulating section of the surgical device;

FIG. 8 is a perspective sectional view of the end effector and the articulating section of the surgical device of FIG. 1, depicting the articulating section without the sheath shown in FIG. 7;

FIG. 10B is a side view of an alignment tube of the surgical device of FIG. 1;

FIG. 10C is a front view of the alignment tube shown in FIG. 10B;

FIG. 10D is a front view of a rotation wheel of the surgical device of FIG. 1;

FIG. 10E is a cross-sectional view of the rotation wheel shown in FIG. 10D, taken along section line 10E-10E of FIG. 10D;

FIG. 17 is a side cross-sectional view of the surgical device of FIG. 1;

FIG. 18 is a rear cross-sectional view of the surgical device of FIG. 1; taken along section line 18-18 of FIG. 17;

FIG. 19 is a rear cross-sectional view of the surgical device of FIG. 1; taken along section line 19-19 of FIG. 17;

FIG. 32 is a perspective view of a surgical device according to another embodiment of the present disclosure, showing an end effector including shearing blades;

FIG. 33 is a perspective view of the end effector and a portion of the articulating section of the surgical device of FIG. 32;

FIG. 36 is a perspective view of a surgical device according to a further embodiment of the present disclosure, showing an end effector including grasping forceps;

FIG. 37 is a perspective view of the end effector of the surgical device of FIG. 36;

FIG. 44 is a perspective view of a surgical device according to another embodiment of the present disclosure, showing an end effector having a probe;

FIG. 45 is a perspective view of the end effector and a portion of an articulating section of the surgical device of FIG. 44;

FIG. 46 is a side cross-sectional view of the end effector and the articulating section of the surgical device of FIG. 44;

DETAILED DESCRIPTION OF THE EMBODIMENTS

Figure 1:
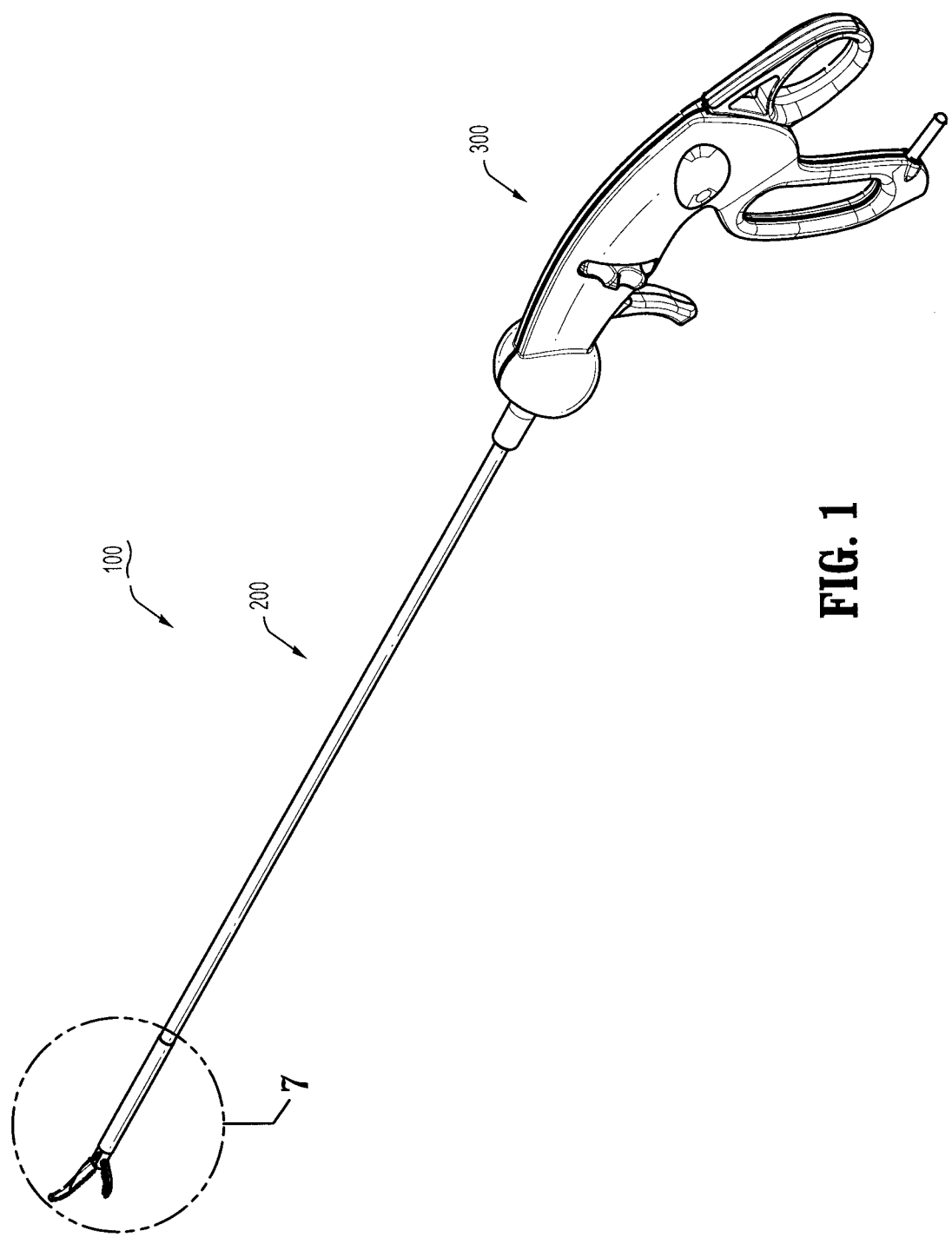
FIG. 1 is a rear perspective view of a surgical device according to an embodiment of the present disclosure.

Embodiments of the presently disclosed surgical device are described in detail with reference to the drawings, in which like reference numerals designate identical or corresponding elements in each of the several views. As used herein the term "distal" refers to that portion of the surgical device, or component thereof, farther from the user, while the term "proximal" refers to that portion of the surgical device, or component thereof, closer to the user.

FIG. 1 illustrates an endoscopic surgical device designated with reference number 100. Surgical device 100 generally includes a handle assembly 300 and an endoscopic assembly 200 extending distally from handle assembly 300. Handle assembly 300 is configured to move relative to endoscopic assembly 200. Endoscopic assembly 200 has an elongate configuration and is operatively associated with handle assembly 300. In some embodiments, handle assembly 300 can be held and operated with only one hand.

As seen in FIGS. 2-6, endoscopic assembly 200 includes an elongate outer tube 210 having a proximal end 212 and a distal end 214. Proximal end 212 of elongate outer tube 210 is secured to handle assembly 300. In the embodiment shown in FIG. 2, elongate outer tube 210 has a straight configuration and defines a longitudinal axis "X" therealong; however, elongate outer tube 210 may have a curved configuration. In some embodiments, elongate outer tube 210 is made wholly or partly from a substantially rigid or stiff biocompatible material such as polyetheretherketone (PEEK), titanium alloy, aluminum alloy, stainless steel, cobalt chromium alloy, or any combination thereof.

With continued reference to FIGS. 2-6, endoscopic assembly 200 further includes an articulating section 230 supported on distal end 214 of elongate outer tube 210. Articulating section 230 has a proximal end 236 and a distal end 238 and is configured to articulate towards a particular direction with respect to elongate outer tube 210 upon movement of handle assembly 300 towards the same direction with respect to elongate outer tube 210.

Figure 2:
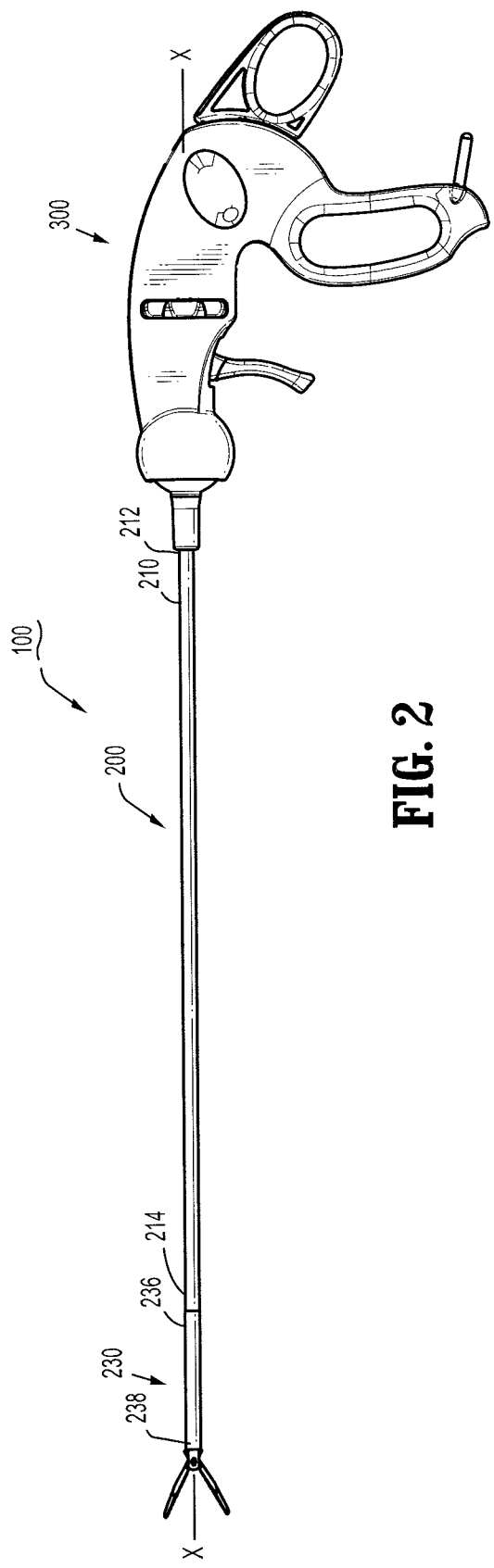
FIG. 2 is a side elevational view of the surgical device of FIG. 1 with an articulating section in a straight position.
Figure 3:
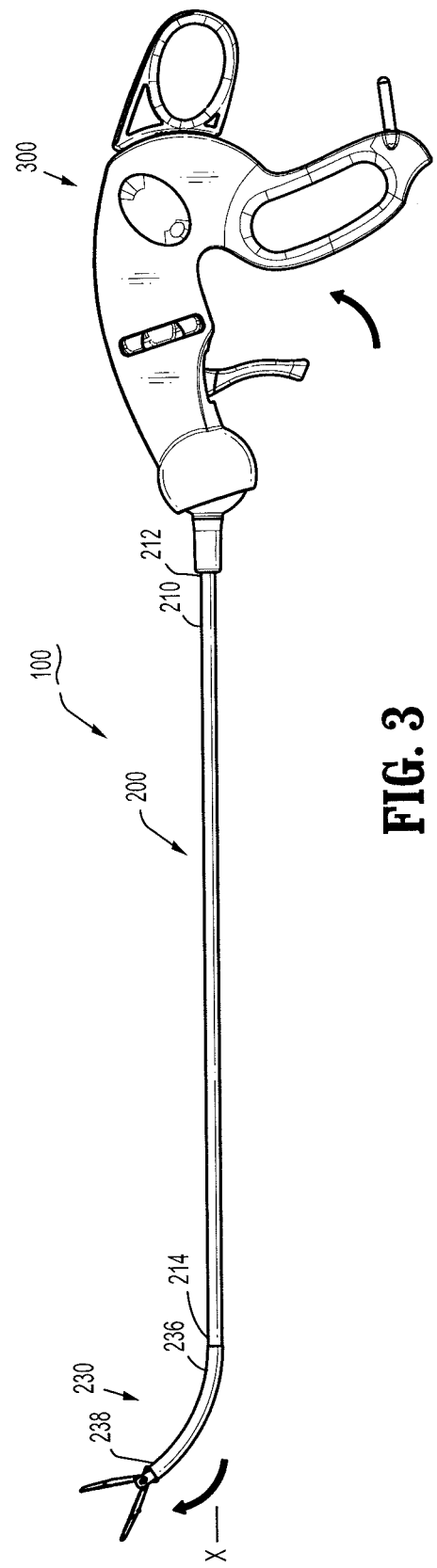
FIG. 3 is a side elevation view of the surgical device of FIG. 1 with the articulating section in an articulated position.

Elongate outer tube 210 and articulating section 230 are longitudinally aligned with each other when handle assembly 300 is positioned in a neutral position, as seen in FIGS. 2 and 4. When handle assembly 300 is moved relative to elongate outer tube 210 toward one direction, articulating section 230 articulates toward the same direction. For example, an operator can move handle assembly 300 upwardly relative to elongate outer tube 210 to articulate articulating section 230 upwardly relative to elongate outer tube 210, as depicted in FIG. 3. In addition to this upward motion, the operator can move handle assembly 300 laterally with respect to elongate outer tube 210 to articulate articulating section 230 laterally relative to elongate outer tube 210, as illustrated in FIG. 5. Although the drawings merely show upward and lateral movements of articulating section 230, articulating section 230 has multitude of degrees of motion. Irrespective of the specific degrees of motion, the movement of articulating section 230 relative to elongate outer tube 210 mirrors the motion of handle assembly 300 with respect to elongate outer tube 210.

Figure 6:
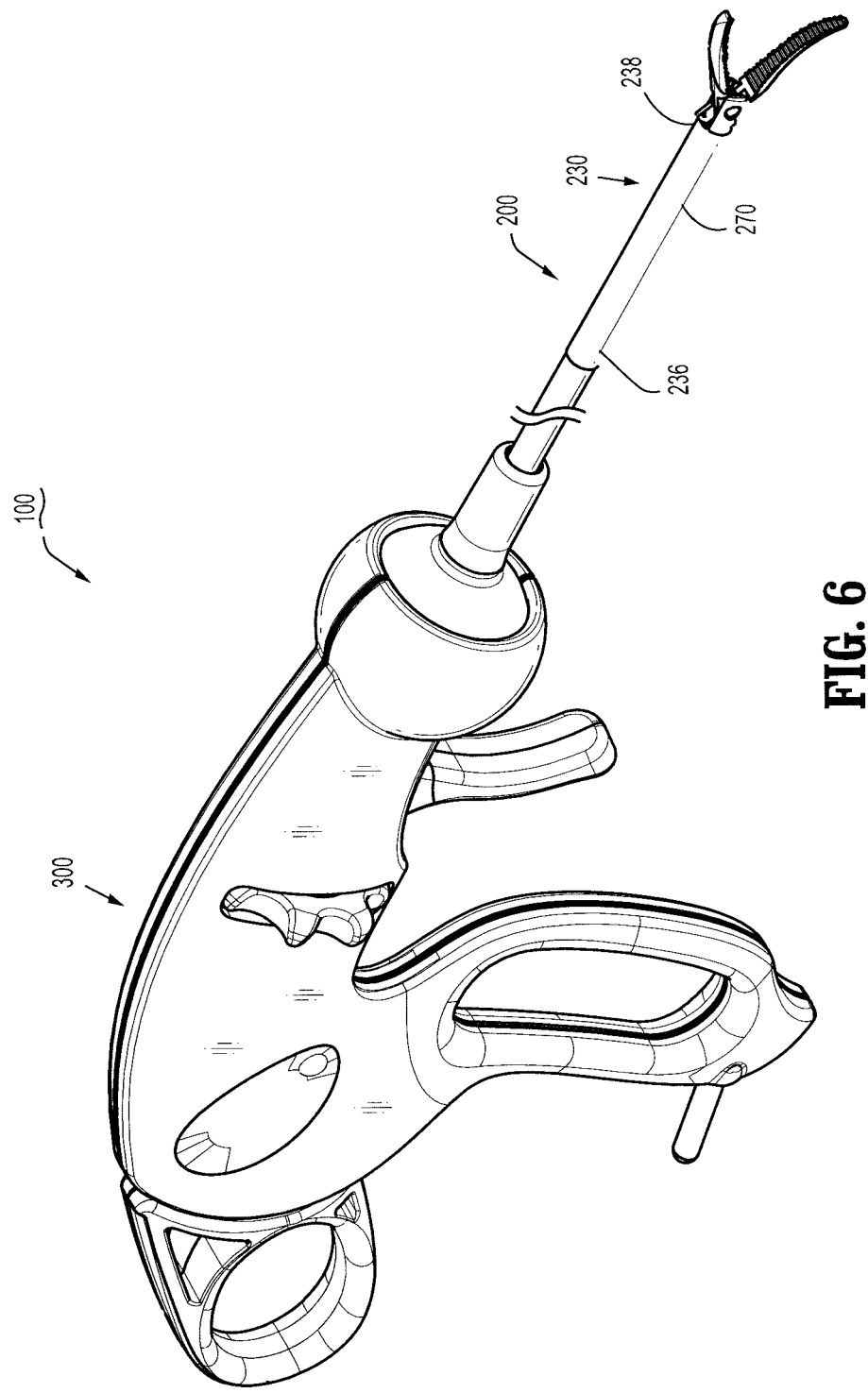
FIG. 6 is a front perspective view of the surgical device of FIG. 1.

With reference to FIGS. 6-8, endoscopic assembly 200 further includes a tool assembly or end effector 260 operatively coupled to distal end 238 of articulating section 230. In certain embodiments, articulating section 230 includes a sheath 270 covering at least a portion of articulating section 230. Sheath 270 is made (wholly or partly) of any suitable flexible material. In some embodiments, sheath 270 is made of a biocompatible polymer. Other embodiments of surgical device 100 do not include sheath 270. Articulating section 230 additionally includes at least two articulation links 232, 234 configured for pivotable movement relative to each other. However, articulating section 230 may include more articulation links. In the depicted embodiment, articulation section 230 includes ten (10) articulation links 232, 234. It is understood that a greater number of articulation links 232, 234 provides articulating section 230 with more degrees of articulation. Regardless of the exact number of articulation links 232, 234, articulation links 232, 234 allows articulating section 230 to articulate relative to elongate outer tube 210. In particular, articulating section 230 can move from a first position longitudinally aligned with elongate outer tube 210 to a myriad of positions that are not longitudinally aligned with elongate outer tube 210.

As discussed above, articulating section 230 is operatively associated with end effector 260. Although the drawings show a specific kind of end effector 260, it is envisioned that surgical device 100 may include any end effector suitable for engaging tissue. For example, an embodiment of surgical device 100 includes the end effector described in U.S. Patent Application Publication Serial No. 2009/0012520, filed on Sep. 19, 2008, which entire contents are herein incorporated by reference.

End effector 260 includes a first jaw member 262 and a second jaw member 264 pivotally coupled to each other. First and second jaw members 262, 264 are configured to move from a first or open position to a second or approximated position. In the first position, first and second jaw members 262, 264 are spaced apart from each other and can receive tissue between them (see FIGS. 7 and 8). In the second position, first and second jaw members 262, 264 are approximated to each other and can grasp or clamp any tissue positioned between them (see FIG. 31).

Each of first and second jaw members 262, 264 includes a tissue engaging surface 266, 268 and a housing 276, 278. Tissue engaging surfaces 266, 268 each include teeth 272, 274 extending along their lengths. Teeth 272, 274 aid in grasping tissue located between first and second jaw members 262, 264 when first and second jaw members 262, 264 are located in the approximated position.

In some embodiments, tissue engaging surfaces 266, 268 are made of an electrically conductive material and housings 276, 278 are formed of an electrical insulating material. As such, tissue engaging surfaces 266, 268 are adapted to receive electrosurgical energy and conduct electrosurgical energy to the tissue grasped between first and second jaw members 262, 264. First and second jaw members 262, 264 are electrically isolated from each other and form a bipolar arrangement. This electrical arrangement allows first and second jaw members 262, 264 to effectively transfer electrical energy through tissue. In a bipolar arrangement, the electrical current travels from one tissue engaging surface (266 or 268) to another tissue engaging surface (266 or 268) through the grasped tissue to complete the circuit. In an alternate embodiment, surgical device 100 has a monopolar electrical arrangement. In this embodiment, end effector 260 transmits electrosurgical energy to the tissue grasped between first and second jaw members 262, 264 and this electrosurgical energy passes through the patient's body until it reaches a patient return electrode (not shown) to complete the circuit. This patient return electrode is electrically coupled to surgical device 100. The user may control the intensity, frequency and duration of the electrosurgical energy applied to the tissue to cauterize, dissect, coagulate, desiccate, seal, and/or simply reduce or slow bleeding during a medical procedure. The electrosurgical energy received by first and second jaw members 262, 264 originates from an electrosurgical generator (not shown) or any other suitable source of electrosurgical energy. In certain embodiments, surgical device 100 is electrically coupled to an electrosurgical generator including a high voltage direct current (HVDC) power supply configured for supplying a DC voltage, an output filter for smoothing the switching of the HVDC into a DC level, and a radio frequency (RF) output stage coupled to the HVDC and configured to convert the DC energy generated by the HVDC into RF energy. In some embodiments, surgical device 100 is electrically coupled to the electrosurgical generator described in U.S. Pat. No. RE40, 388, filed on May 8, 2003, the entire contents of which are hereby incorporated by reference.

Figure 9:
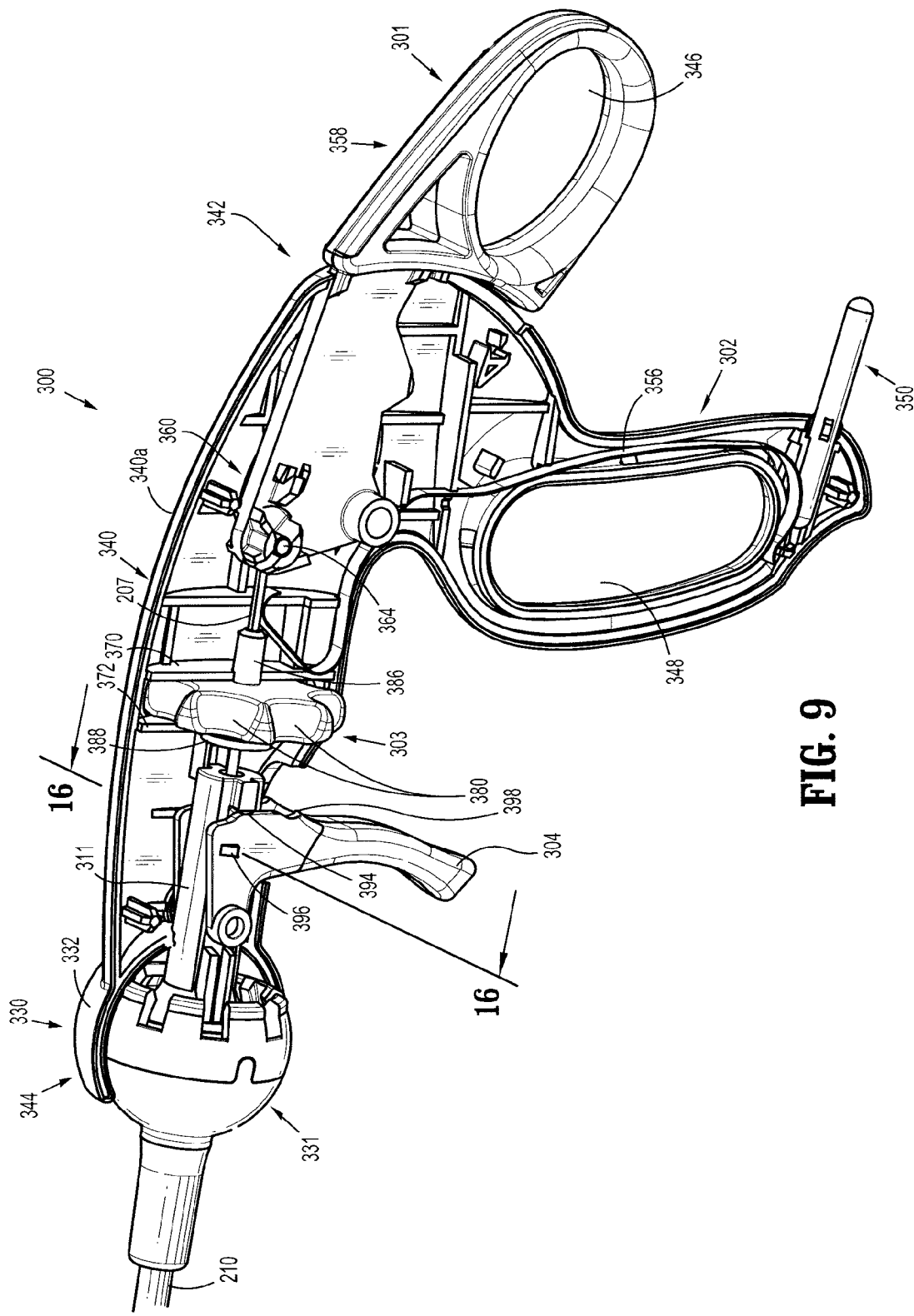
FIG. 9 is a perspective cutaway view of a handle assembly of the surgical device of FIG. 1, showing the internal components of the handle assembly.
Figure 10A:
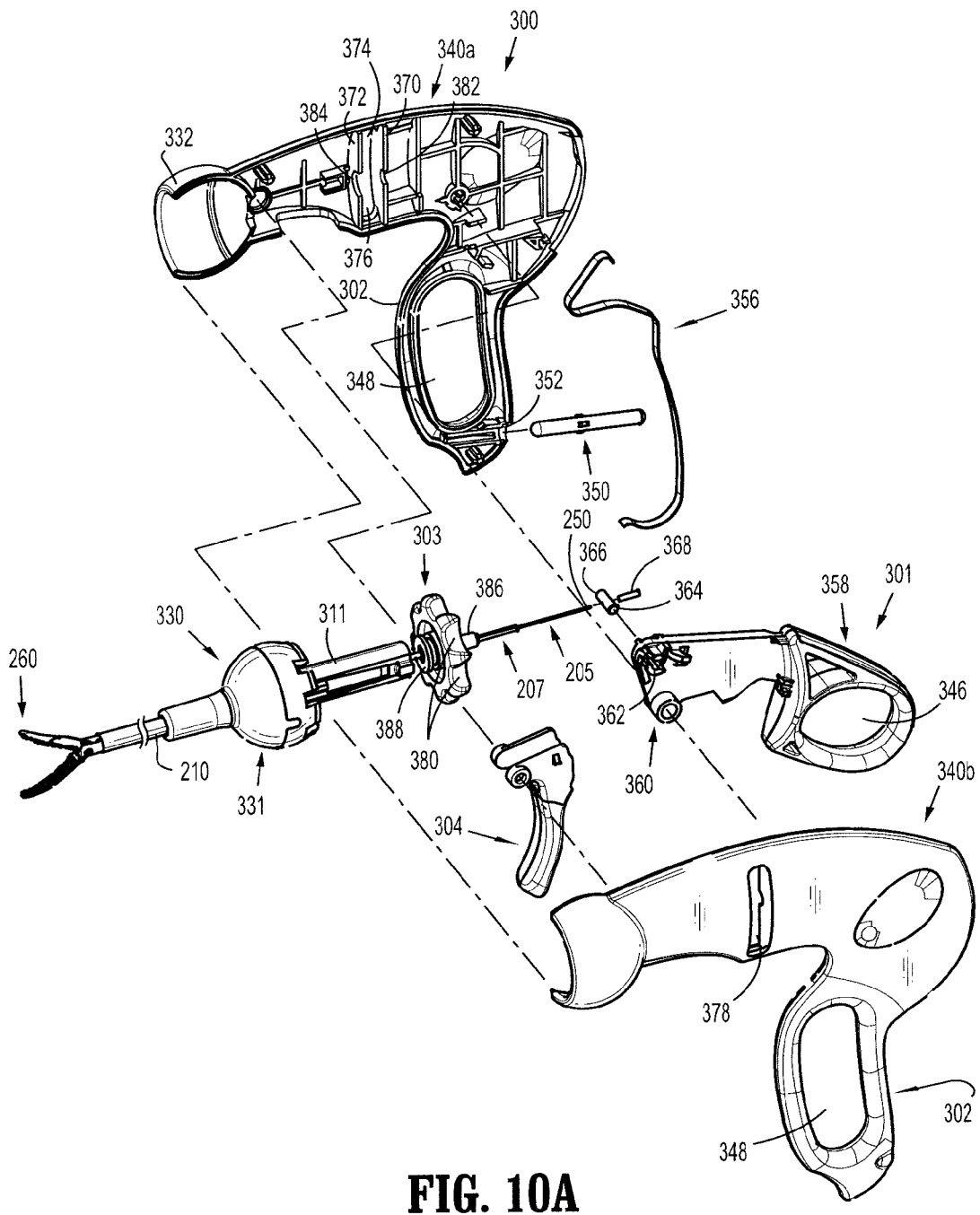
FIG. 10A is a perspective exploded view of the surgical device of FIG. 1.

With reference to FIGS. 9 and 10, handle assembly 300 is configured to be electromechanically coupled to an electrosurgical generator (not shown) and includes a housing 340 for storing, among other things, at least some parts of an articulation mechanism 330. As seen in FIG. 10A, housing 340 includes a first half 340a and a second half 340b configured to attach to one another. In several embodiments, first and second halves 340a, 340b may be made of a polymer (or any other suitable material). First and second halves 340a, 340b collectively form a cup 332 for holding a ball 331 of articulation mechanism 330. Cup 332 is positioned on a distal end portion 344 (FIG. 9) of handle assembly 300. Handle assembly 300 further includes a movable thumb loop 301 positioned on a proximal end portion 342 (FIG. 9) thereof. Movable thumb loop 301 is operatively connected to end effector 260 (FIG. 7) and is configured to move upwardly and downwardly relative to housing 340. In various embodiments, movable thumb loop 301 is pivotally secured to housing 340. Moving movable thumb loop 301 with respect to housing 340 causes end effector 260 to move between the open position and the approximated position, as discussed in detail below. Movable thumb loop 301 defines an aperture 346 dimensioned to receive a user's finger. Aperture 346 is located in a proximal end portion 358 of movable thumb loop 301. At least a distal end portion 360 of movable thumb loop 301 is positioned inside housing 340.

Handle assembly 300 further includes a finger loop 302 defining an opening 348 dimensioned to receive a user's finger. Finger loop 302 remains stationary relative to housing 340. Finger loop 302 includes a longitudinal cavity 352 (FIG. 10A) for retaining a post 350 adapted to facilitate electromechanical coupling between surgical device 100 and an electrosurgical generator (not shown). Post 350 is partially positioned within finger loop 302 and is made wholly or partly of an electrically conductive material. In one embodiment, an electrical and thermal insulating sheath (not shown) wraps a portion of post 350 located outside of finger loop 302. This insulating sheath protects the user from the electrical current traveling through post 350 during the operation of surgical device 100. The portion of post 350 located inside finger loop 302 is electromechanically coupled to an electrical connector 356 made of an electrically conductive material. Electrical connector 356 extends through finger loop 302 into an inner portion of housing 340. A portion of electrical connector 356 located inside housing 340 is disposed in electromechanical cooperation with an alignment tube 207 made of an electrically conductive material. Alignment tube 207 surrounds a portion of an actuation cable 205 (FIG. 10A). In some embodiments, actuation cable 205 is made of an electrically conductive material. In these embodiments, an electrical current traveling through alignment tube 207 can reach actuation cable 205.

A proximal end 250 (FIG. 10A) of actuation cable 205 is operatively connected to distal end portion 360 of movable thumb loop 301. In certain embodiments, distal end portion 360 of movable thumb loop 301 defines a longitudinal recess 362 aligned transversely relative to actuation cable 205. Longitudinal recess 362 is dimensioned to receive a pin 364. Pin 364 has a hole 366 longitudinally aligned with actuation cable 205. Longitudinal hole 366 is adapted to receive proximal end 250 of actuation cable 205. Ferrule 368 surrounds proximal end 250 of inner shaft 205 and retains proximal end 250 of actuation cable 205 within longitudinal hole 366 of pin 364. Pin 364 in turn connects proximal end 250 of actuation cable 205 to distal end portion 360 of movable thumb loop 301. Alignment tube 207 is crimped onto the actuation cable 205 distally of pin 364. Thus, ferrule 368 and alignment tube 207 sandwich pin 364, maintaining the axial relationship between actuation cable 205 and pin 364. Accordingly, when pin 364 is moved, actuation cable 205 moves as well. However, actuation cable 205 is capable of axial rotation in relation to the pin 364.

As seen in FIGS. 10B and 10C, alignment tube 207 does not have a circular external cross shape. Instead, alignment tube 207 has one or more flat sides. At least one side of alignment tube 207 may have a round profile. The non-circular external cross section of alignment tube 207 corresponds to the internal cross section of the internal passageway 399 extending through proximal elongated portion 386 (FIGS. 10A, 10D, and 10E) of rotation wheel 303. Thus, when the rotation wheel 303 is rotated, alignment tube 207 rotates as well and, because it is crimped to actuation cable 205, the actuation cable 205 will also rotate.

Figure 20:
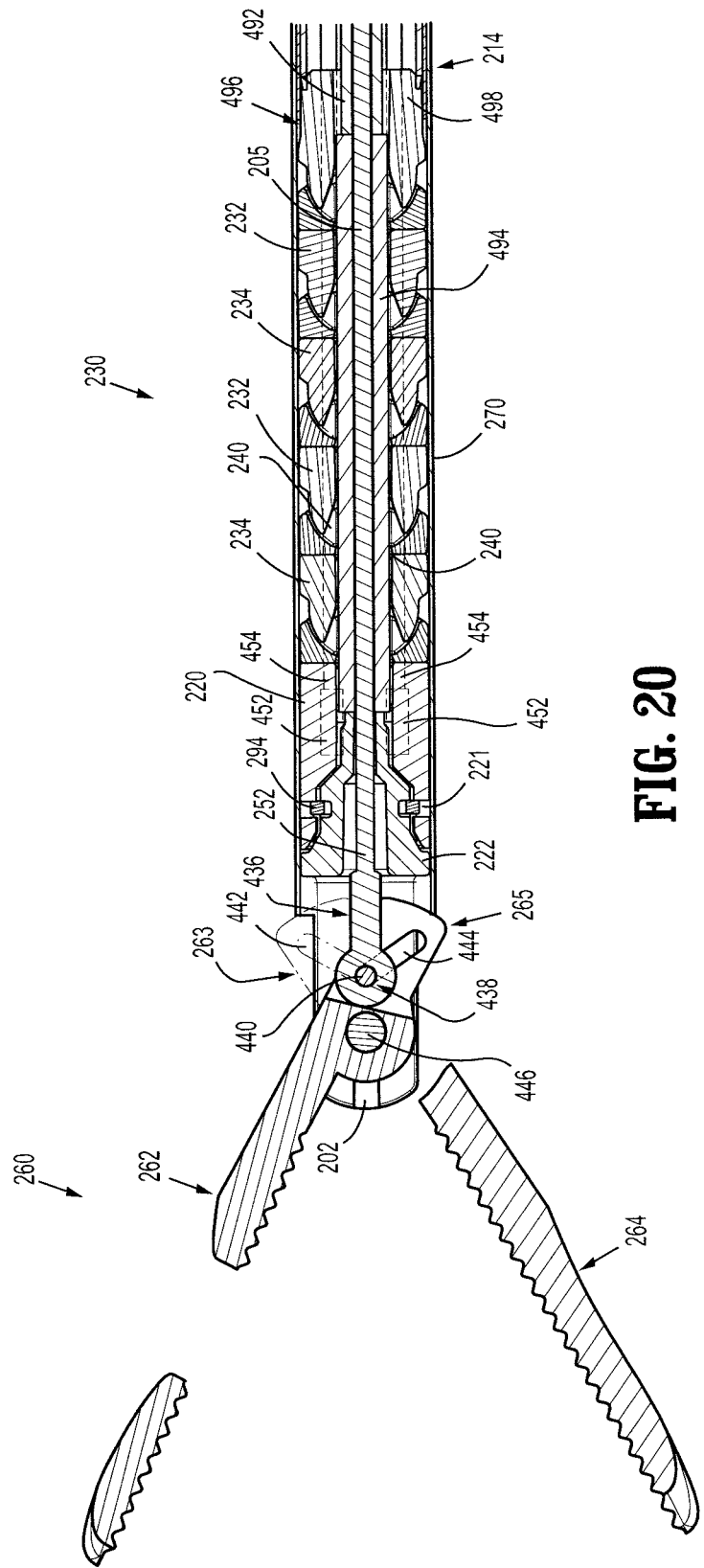
FIG. 20 is a side cross-sectional view of the end effector and the articulating section of the surgical device of FIG. 1, taken around section 20 of FIG. 17.
Figure 31:
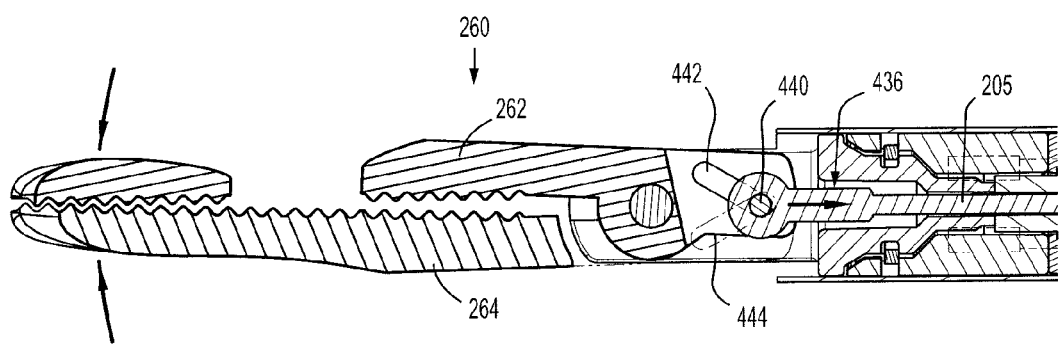
FIG. 31 is a side cross-sectional view of the end effector and a portion of the articulating section of the surgical device of FIG. 1, depicting end effector moving an approximated position in response to an actuation of the movable thumb loop shown in FIG. 30.

Movable thumb loop 301 is configured to move relative to housing 340 to actuate end effector 260. In various embodiments, movable thumb loop 301 can pivot toward and away from finger loop 302. When an operator moves movable thumb loop 301 toward finger loop 302, actuation cable 205 translates in a proximal direction. As a result of this proximal translation, first and second jaw members 262, 264 of end effector 260 move from an open position (FIG. 20) to an approximated position (FIG. 31). Moving movable thumb loop 301 away from finger loop 301, on the other hand, urges actuation cable 205 in a distal translation. In response to this distal translation, first and second jaw members 262, 264 of end effector 260 move from the approximated position (FIG. 31) to the open position (FIG. 20).

Handle assembly 300 also includes a rotation wheel 303 mounted on alignment tube 207. Rotation wheel 303 is configured to rotate relative to housing 340. Some portions of rotation wheel 303 stick out of housing 340, allowing an operator to reach rotation wheel 303. Other portions of rotation wheel 303 are secured within housing 340. Housing 340 includes a first inner wall 370 and a second inner wall 372 spaced apart from each other. First and second inner walls 370, 372 define a gap 374 (FIG. 10A) therebetween. Gap 374 is dimensioned to receive at least a portion of rotation wheel 303 and is disposed in communication with a first slot 376 (FIG. 10A) of first half 340a and a second slot 378 (FIG. 10A) of second half 340b of housing 340. At least some portions of rotation wheel 303 exit housing 340 through first and second slots 376, 378, thereby providing access to rotation wheel 303. Each of first and second inner walls 370, 372 defines a recess 382 and 384 (FIG. 10A) for holding portions of rotation wheel 303. Specifically, recess 382 of inner wall 370 supports a proximal elongate portion 386 of rotation wheel 303. Proximal elongate portion 386 extends proximally from rotation wheel 303 and surrounds at least a portion of alignment tube 207 (see FIG. 9). Recess 384 of second inner wall 372 supports a distal tubular member 388 releasably attached to a distal end of rotation wheel 303.

Figure 11A:
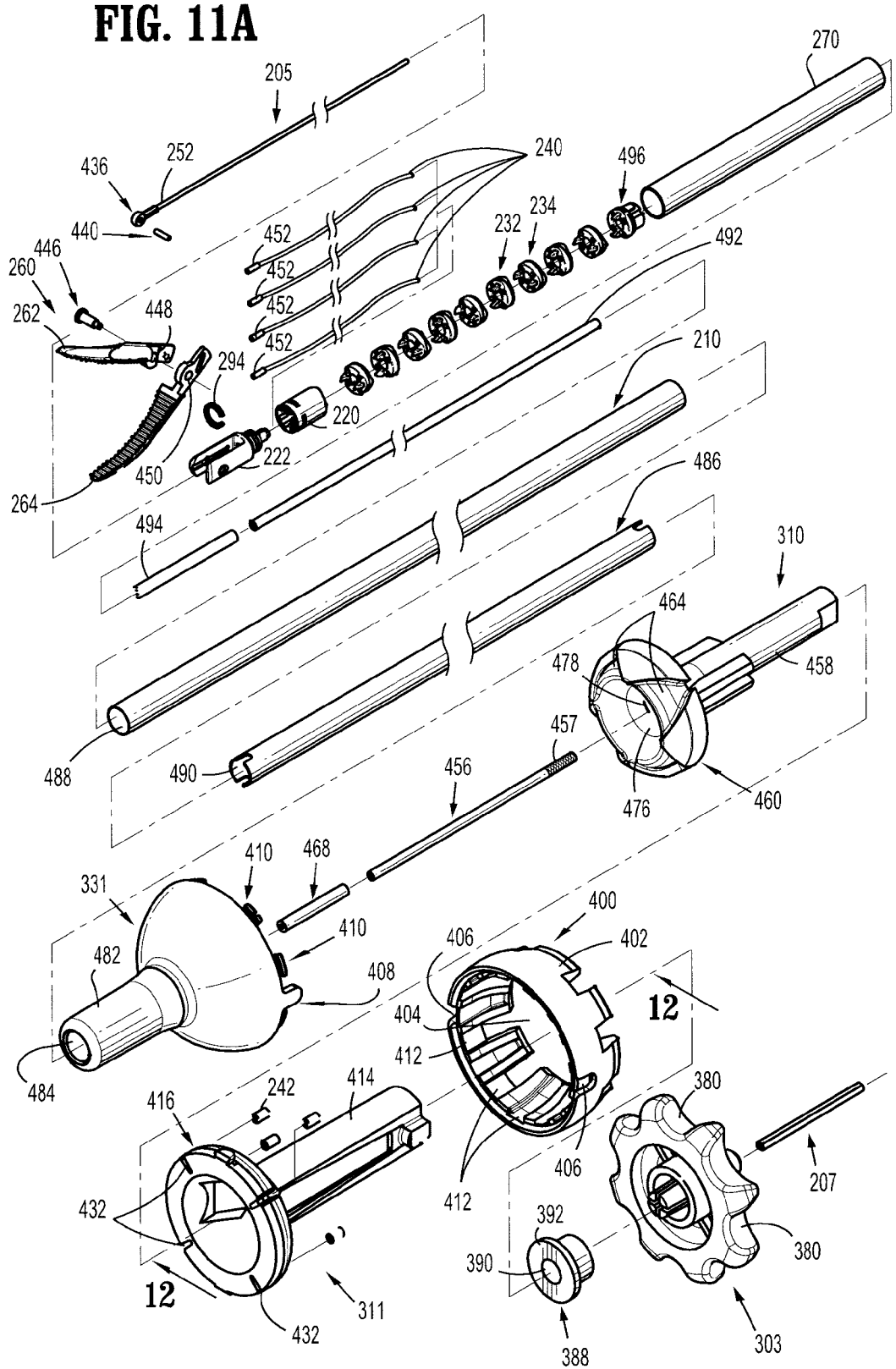
FIG. 11A is a perspective exploded view of an articulation mechanism, the end effector, and the articulating section of the surgical device of FIG. 1.
Figure 11B:
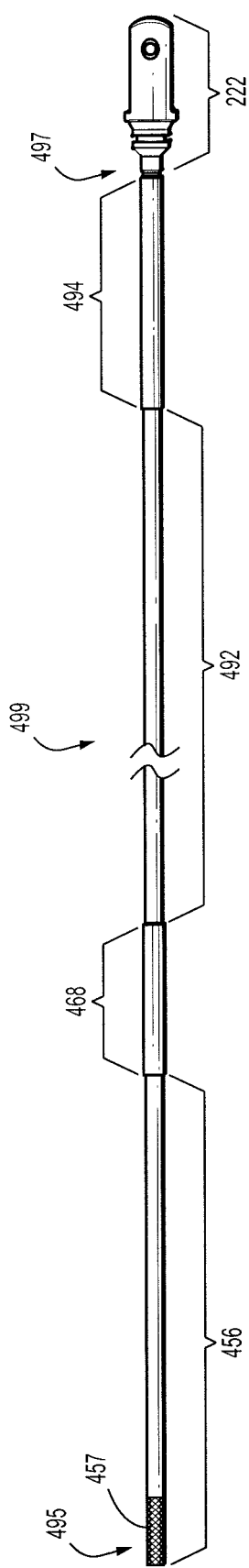
FIG. 11B is a side view of a torque shaft of the surgical device of FIG. 1.
Figure 11C:
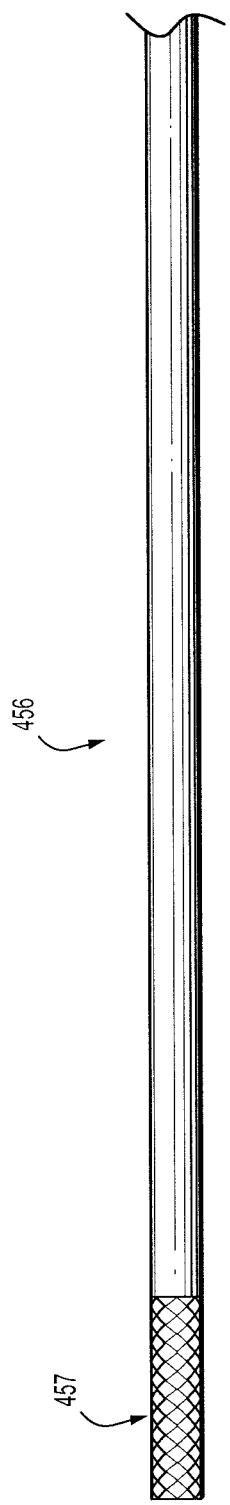
FIG. 11C is a side view of a proximal torque tube of the torque shaft shown in FIG. 11B.
Figure 21:
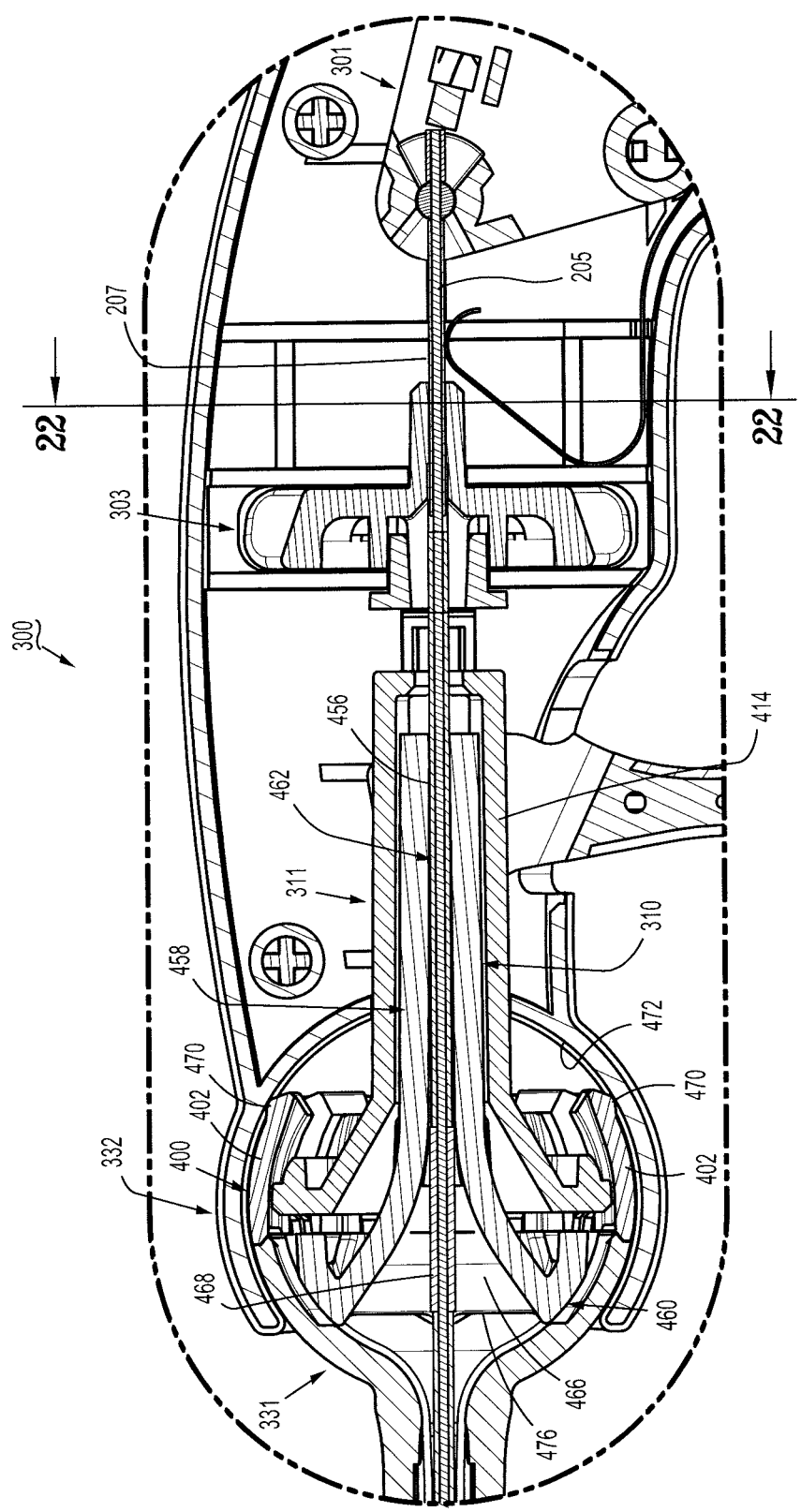
FIG. 21 is a side cross-sectional view of a portion of the handle assembly of the surgical device of FIG. 1, taken around section 21 of FIG. 17.
Figure 22:
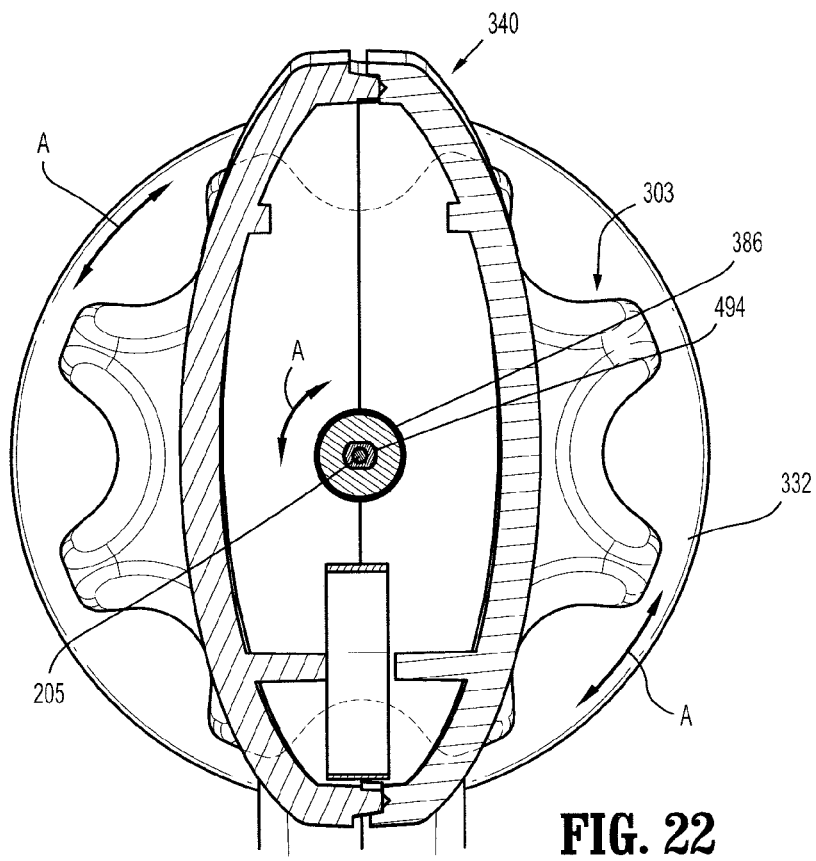
FIG. 22 is a rear cross-sectional view of a portion of the handle assembly of the surgical device of FIG. 1, taken along section line 22-22 of FIG. 21.

With reference to FIGS. 11B and 11C, a torque shaft 499 has a proximal end portion 495 and a distal end portion 497 and, during operation, transfers rotational torque from rotation wheel 303 (FIG. 11A) to end effector 260 (FIG. 8). The distal end portion 497 of torque shaft 499 is operatively connected to coupling member 222, while the proximal end portion 495 of torque shaft 499 is coupled rotation wheel 303 (FIG. 21). Torque shaft 499 includes a proximal torque tube 456, a proximal torque coil 468, a distal torque tube 492, and a distal torque coil 494. Each component of torque shaft 499 is connected to one another. In certain embodiments, all the components comprising torque shaft 499 are welded together and distal torque coil 494 is welded to coupling member 222. In some embodiments, proximal torque coil 468 and distal torque coil 494 are each made of three layers of torque coil sold by ASAHI INTECC CO., LTD. or equivalents. The different layers of the torque coil have opposite direction winds so that the coil can be rotated in either direction without unwinding. As seen in FIG. 11C, proximal torque tube 456 includes a diamond knurl patterned section 457 at its proximal end.

Figure 11D:
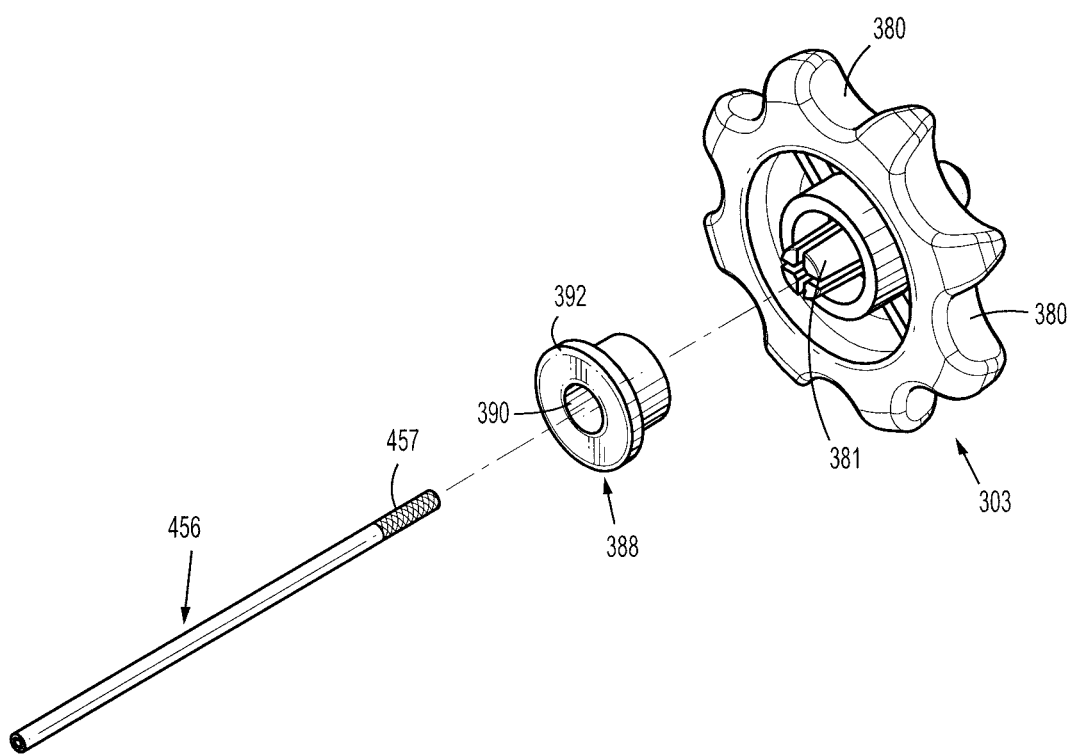
FIG. 11D is a perspective view of a rotation wheel, a distal tubular member 388, and a proximal torque tube 456 of the surgical device of FIG. 1.
Figure 23:
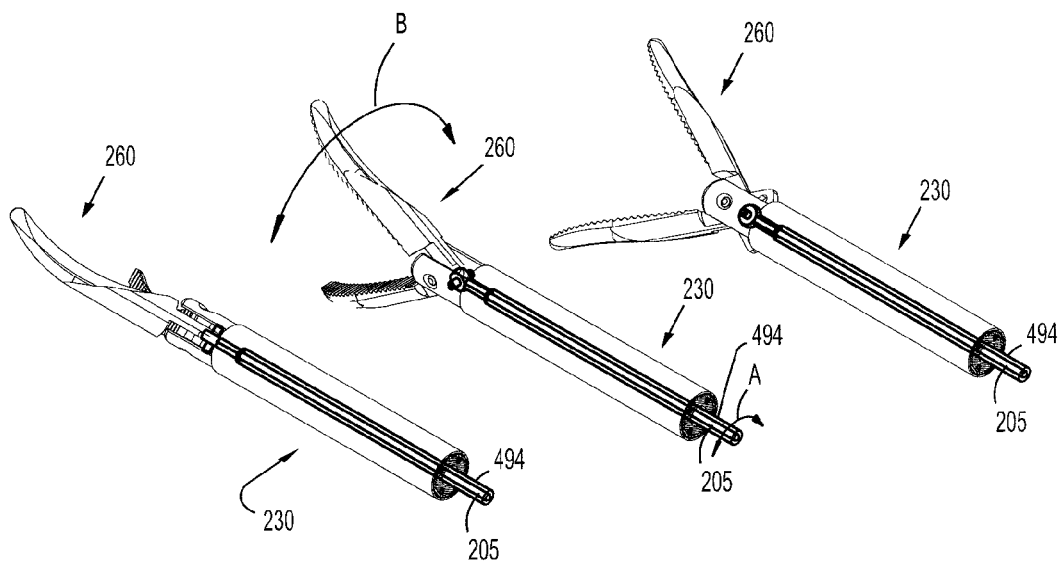
FIG. 23 is a perspective view of the end effector and the articulating section of the surgical device of FIG. 1 during various stages of rotation along its longitudinal axis.

Referring to FIG. 11D, rotating rotation wheel 303 causes proximal torque tube 456 to rotate in the same direction. The torque and resulting rotation is then transferred through the other elements of torque shaft 499 to the coupling member 222, thus rotating the end effector 260 (see FIG. 23). Rotation wheel 303 includes a plurality of undulations 380 positioned around its periphery and four distal extension members 381. Undulations 380 are ergonomically configured to receive a user's fingers and facilitate rotation of wheel 303 by the user. Proximal torque tube 456 fits within the four distal extension members 381 with at least a portion of the diamond knurled pattern section 457 contacting the inner surfaces of the four distal extending members 381. A distal tubular member 388 is placed over the four distal extension members 381. Distal tubular member 388 defines a longitudinal opening 390 dimensioned for receiving the four distal extension members 381 and includes a flange 392 disposed around a distal end thereof. Longitudinal opening 390 of distal tubular member 388 contacts the external surfaces of the four distal extension members 381. The internal diameter of the longitudinal opening 390 is such that, when distal tubular member 388 is placed over the four extension members 381 and the proximal torque tube 456, the four extension members 381 are pressed into the diamond knurled pattern section 457, creating a press fit.

With continued reference to FIGS. 9 and 10, articulation mechanism 330 includes an articulation lock trigger 304 positioned distally of rotation wheel 303 and configured for locking the position of articulating section 230 (FIG. 2) relative to elongate outer tube 210. Articulation lock trigger 304 is operatively coupled to an articulation cable plate 311 and can move relative to housing 340. In several embodiments, articulation lock trigger 304 can pivot with respect to housing 340 between a first or unlocked position and a second or locked position. When an operator moves articulation lock trigger 304 from the unlocked position toward the locked position, articulation cable plate 311 moves proximally with respect to housing 340 to lock the position of articulating section 230 with respect to elongate outer tube 210, as discussed in detail below. In the depicted embodiment, articulation lock trigger 304 defines a detent recess 398 positioned on a proximal surface therefore and adapted to receive a detent 394 of articulation cable plate 311. Detent 394 of articulation cable plate 311 engages detent recess 398 when articulation lock trigger 304 is located in the locked position. Articulation lock trigger 304 also include at least one tab 396 positioned within housing 340. In some embodiments, articulation lock trigger 304 includes two tabs 396 located on opposite sides of articulation lock trigger 304.

Figure 12:
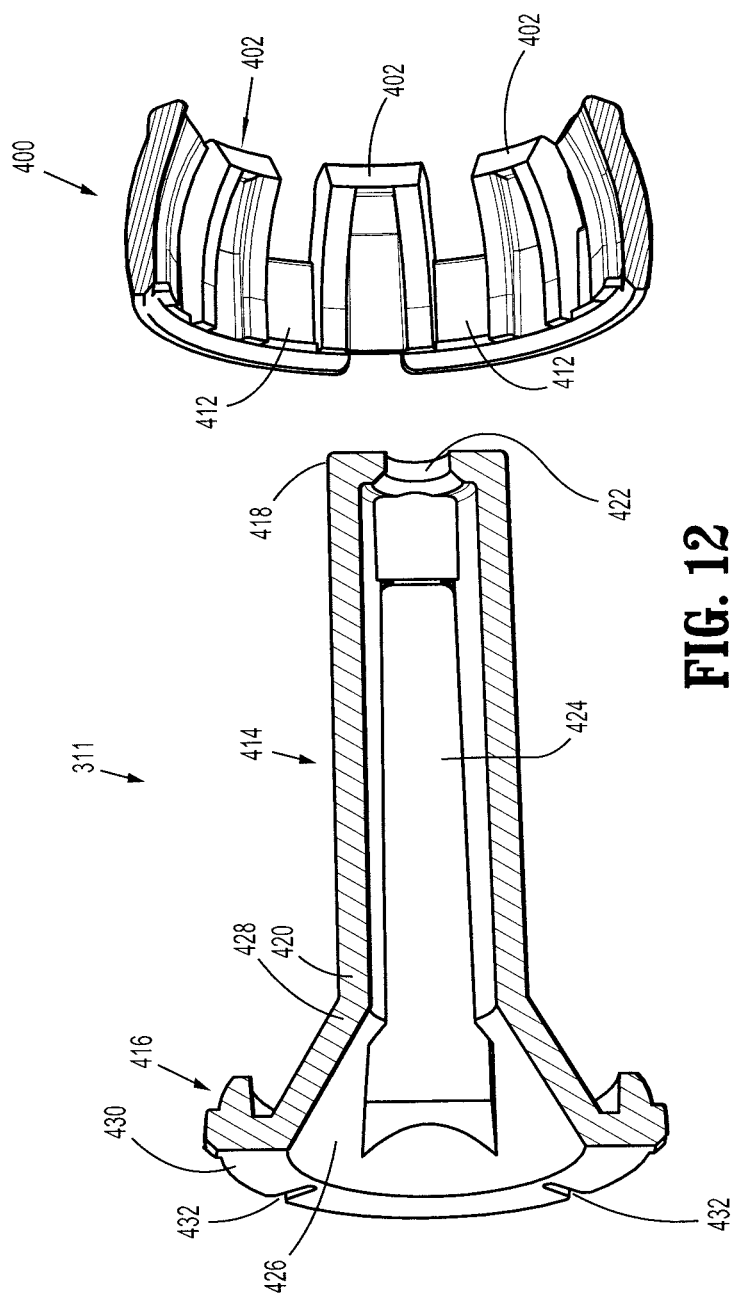
FIG. 12 is a perspective cross-sectional view of an articulation cable plate and an articulation lock ring of the articulation mechanism of FIG. 11A, taken along section line 12-12 of FIG. 11A.

Referring to FIGS. 11 and 12, articulation mechanism 330 includes an articulation lock ring 400 partially surrounding articulation lock plate 311. Articulation lock ring 400 defines an opening 404 (FIG. 11A) dimensioned to receive articulation lock plate 311 and includes a plurality of locking fingers 402 extending proximally therefrom. Locking fingers 402 are positioned around a periphery of articulation lock ring 400 and may be (wholly or partly) made of a resilient material. Articulation lock ring 400 is positioned inside cup 332 of housing 340 (FIG. 9) and includes two lateral slots 406 (FIG. 11A) disposed in a diametrically opposed relation to each other. Each lateral slot 406 is adapted to receive an extension member 408 of ball 331. In some embodiments, ball 331 includes two extension members 408 disposed in diametrically opposed relation to each other. Each extension member 408 extends proximally from ball 331. When extension members 408 of ball 331 engage slots 406 of articulation lock ring 400, ball 331 is precluded, or at least hindered, from rotating relative to articulation lock ring 400. Ball 331 further includes snap-fit detents 410, or any other apparatus, mechanism, or means suitable for facilitating secure engagement between the ball 331 and articulation lock ring 400. Snap-fit detents 410 are configured to securely engage engagement walls 412 located around an inner surface of articulation lock ring 400 and between fingers 402.

As shown in FIG. 11A, articulation lock ring 400 partially surrounds an articulation cable plate 311. Articulation cable plate 311 has an elongate portion 414 and a cable engaging portion 416. Elongate portion 414 of articulation cable plate 311 has a proximal end 418 and a distal end 420 and defines an opening 422 at proximal end 418 and a bore 424 extending therethrough. Opening 422 leads to bore 424 and is dimensioned to receive proximal torque tube 456 (FIG. 12). Bore 424 is also dimensioned to receive elongate section 458 of annular hub 310 (FIG. 10A).

With continued reference to FIG. 12, cable engaging portion 416 of articulation cable plate 311 is coupled to a distal end 420 of elongate portion 414 and defines an inner cavity 426. In some embodiments, cable engaging portion 416 has a frusto-conical shape. Inner cavity 426 is disposed in communication with bore 424. Additionally, cable engaging portion 416 includes a proximal section 428 connected to elongate portion 414 and a distal section 430 defining a plurality of channels 432. Channels 432 are positioned around the perimeter of distal section 430 of cable engaging portion 416 and each is configured to accommodate an articulation cable 240 (FIG. 11A) and a ferrule or crimp 242 (FIG. 11A).

Returning to FIG. 12, articulation mechanism 330 includes one or more articulation cables 240 operatively coupled to articulation cable plate 311. In the depicted embodiment, four articulation cables 240 are operatively connected to articulation cable plate 311. A ferrule 242 retains each of the four articulation cables 240 in articulation cable plate 311. Specifically, a ferrule 242 is positioned in a channel 432 of articulation cable plate 311 which surrounds and holds a portion of an articulation cable 240, thereby maintaining articulation cable 240 connected to articulation cable plate 311.

Figure 13:
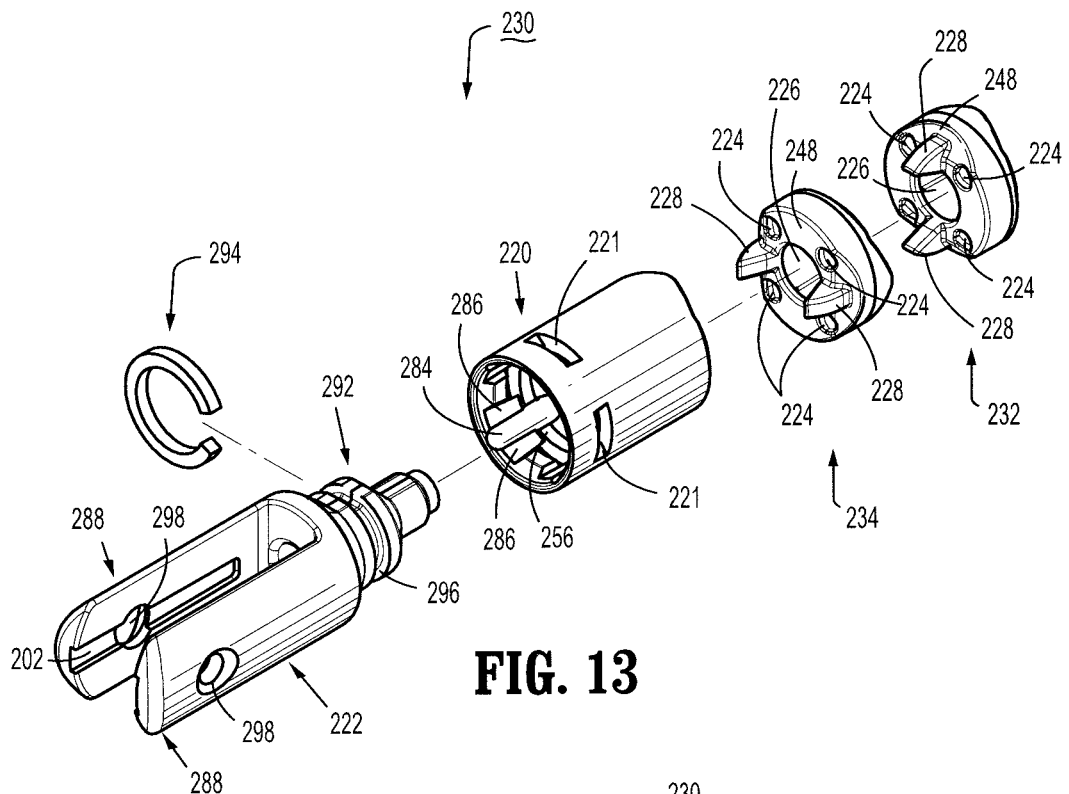
FIG. 13 is a front exploded view of a portion of the articulating section of the surgical device of FIG. 1.
Figure 14:
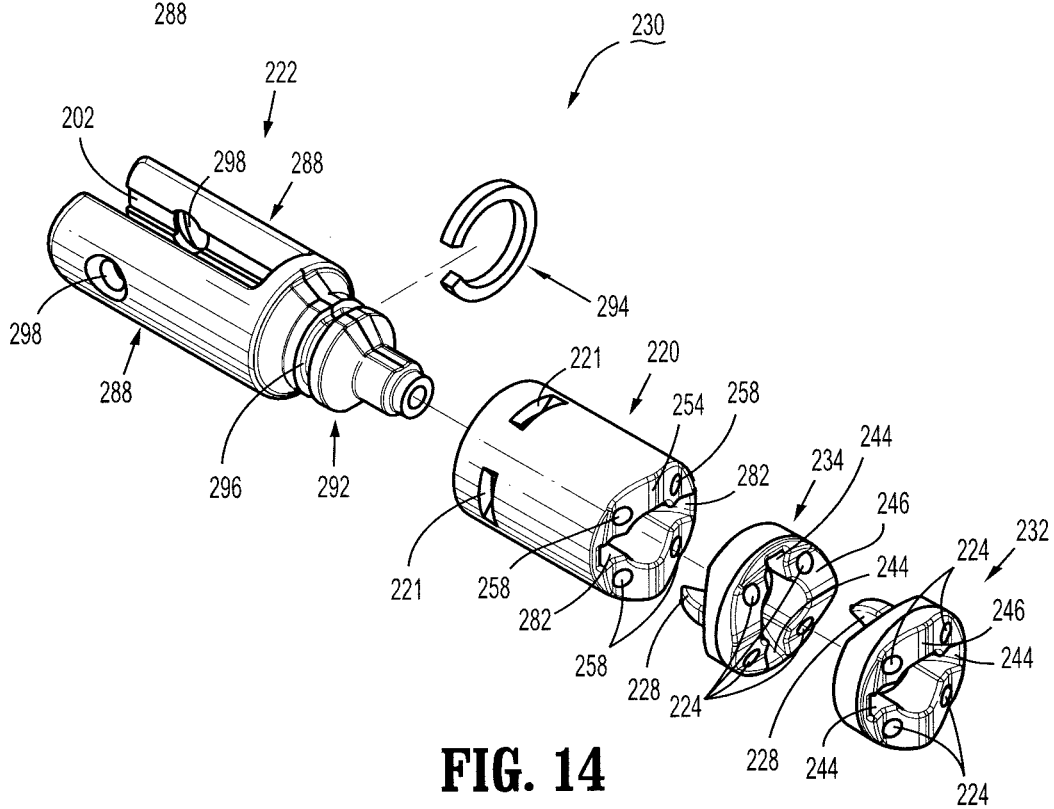
FIG. 14 is a rear exploded view of a portion of the articulating section the surgical device of FIG. 1.
Figure 15:
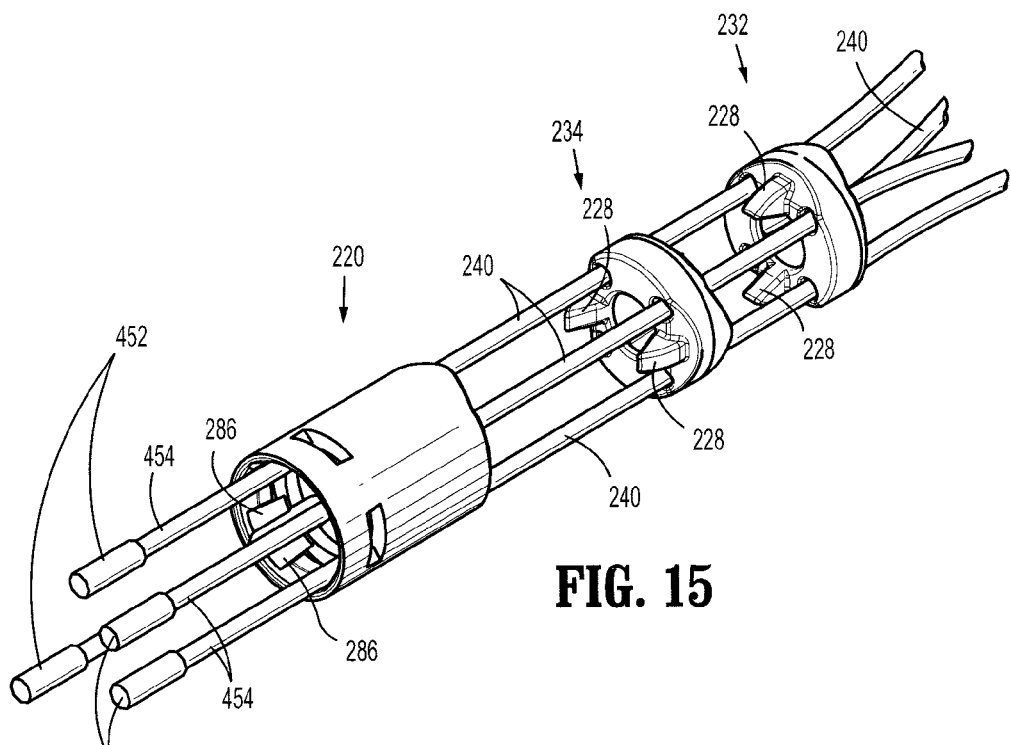
FIG. 15 is a perspective view of the articulating section of the surgical device of FIG. 1, showing articulation cables passing through articulation links and a distal outer tube of the articulating section.

With reference to FIGS. 13-15, articulation cables 240 are operatively coupled to articulating section 230 (see also FIG. 20). Articulating section 230 includes a plurality of articulation links 232, 234 (see also FIG. 11A), a distal outer tube 220, and a coupling member 222. In certain embodiments, coupling member 22 is a knuckle coupler. Each articulation link 232, 234 defines at least one bore 224 adapted to receive an articulation cable 240 (FIG. 15) and a central opening 226 adapted to receive distal torque tube 492 (FIG. 20). In the depicted embodiment, each articulation link 232, 234 includes four bores 224 located around central opening 226. Articulation links 232, 234 further include extension members 228 extending distally therefrom and recesses 244 (FIG. 14) for receiving extension members 228. Recesses 244 are positioned on a proximal surface 246 of each articulation link 232, 234. Proximal surfaces 246 of articulation links 232, 234 each have a contoured profile. The contoured profile of proximal surfaces 246 is configured to mate with the contoured profile of distal surfaces 248 of articulation links 232, 234. Although proximal surfaces 246 and distal surfaces 248 mate with each other, the contoured profile of these surfaces 246, 248 provide articulation links 232, 234 certain degree of motion relative to each other. In addition, articulation links 232, 234, albeit substantially similar, have different orientations with respect to each other. In some embodiments, articulation link 232 is oriented about 90 degrees relative to articulation link 234, as shown in FIG. 13.

With continued reference to FIGS. 13-15, distal outer tube 220 has a proximal surface 254 contoured to mate with distal surface 248 of either articulation link 232 or 234 while permitting movement of the adjacent articulation link 232 or 234 relative to distal outer tube 220. Recesses 282 are defined on proximal surface 254 and each is configured to receive an extension member 228 of articulation links 232, 234. Proximal surface 254 of distal outer tube 220 further defines one or more holes 258 dimensioned to receive articulation cables 240. In the depicted embodiment, distal outer tube 220 has four holes 258. It is envisioned, however, that distal outer tube 22 may have more or fewer holes 258. Moreover, distal outer tube 220 defines a central opening 256 adapted to receive at least a portion of coupling member 222 and at least one channel 284 for holding a portion of an articulation cable 240 within distal outer tube 220. In some embodiments, distal outer tube 220 includes four channels 284 disposed around an inner surface of distal outer tube 220. In addition, distal outer tube 220 include two retaining wall 286 positioned on opposite sides of each channel 284 to retain an articulation cable 240 in channel 284. (See also FIG. 15).

With continued reference to FIGS. 13-15, coupling member 222 includes two legs 288 defining a space therebetween and a proximal projection 292. Each leg 288 of coupling member 222 includes a transverse opening 298 and a longitudinal track 202 disposed along an inner surface thereof. Proximal projection 292 of coupling member 222 defines an annular recess 296 adapted to receive a seal or band 294. In the illustrated embodiment, band or seal 294 has a substantially C-shaped. Band 294 aids in securing coupling member 222 to distal outer tube 220 when band 294 is placed in recess 296 and proximal projection 292 is positioned inside distal outer tube 220. When projection 292 is placed within distal outer tube 220, portions of band 294 stick out through circumferential slots 221 of distal outer tube 220, securing coupling member 222 to distal outer tube 220. Distal outer tube 220 may have one or more circumferential slots 221. In the depicted embodiment, distal outer tube 220 has four circumferential slots 221 positioned around a periphery thereof.

Figure 16:
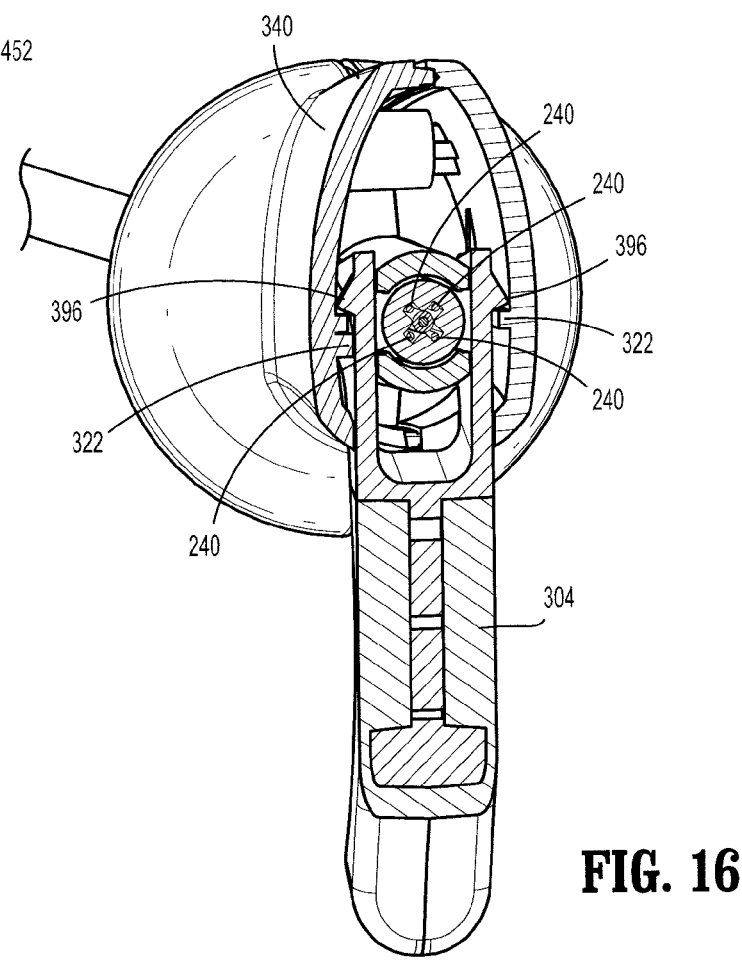
FIG. 16 is a rear cross-sectional view of the handle assembly of FIG. 9, taken along section line 16-16 of FIG. 9.

Referring to FIG. 16, articulation cables 240 are operatively coupled to articulation lock trigger 304. In some embodiments, articulation lock trigger 304 includes two tabs 396 located on opposite sides of articulation lock trigger 304, as discussed above. Articulation lock trigger 304 can move relative to housing 340 between a locked position and an unlocked position, as discussed in detail below. When articulation lock trigger 304 is placed in the locked position, articulation mechanism 330 (FIG. 9) fixes the position of articulation cables 240, thus precluding, or at least inhibiting, articulation of articulating section 230 relative to longitudinal axis "X." (See FIG. 2). Conversely, when articulation lock trigger 304 is placed in the unlocked position (FIG. 16), articulation mechanism 330 (FIG. 9) allows articulating section 230 to articulate relative to longitudinal axis "X." (See FIG. 2). In the unlocked position, tabs 396 of articulation lock trigger 304 seat on internal ribs 322 of housing 340, thereby holding articulation lock trigger 304 in the unlocked position.

As seen in FIGS. 17-19, an embodiment of surgical device 100 includes four (4) articulation cables $240_A$, $240_B$, $240_C$, $240_D$. Each articulation cable $240_A$, $240_B$, $240_C$, $240_D$ extends from articulation cable plate 311 to articulating section 230. While extending through surgical device 100, articulation cables $240_A$, $240_B$, $240_C$, $240_D$ change their position 180 degrees (see FIGS. 18 and 19), allowing articulating section 230 to articulate in the same direction as handle assembly 300.

With reference to FIG. 20, articulating section 230 is operatively coupled to end effector 260. Actuation cable 205 extends through articulating section 230 and is connected to end effector 260. A distal torque coil 494 surrounds a portion of actuation cable 205 extending through articulating section 230. In one embodiment, distal torque coil 494 is a SUS304 or SUS316 grade stainless steel torque coil sold by ASAHI INTECC CO., LTD. Distal end 252 of actuation cable 205 is operatively coupled to end effector 260. In some embodiments, a coupling 436 connects distal end 252 of actuation cable 205 to end effector 260 (see also FIG. 11A). Coupling 436 defines a transverse hole 438 dimensioned to receive a pin 440. In these embodiments, pin 440 passes through hole 438 and cam slots 442, 444 of first and second jaw members 262, 264, thereby pivotally coupling actuation cable 205 to end effector 260. First jaw member 262 has a cam slot 444 located at a proximal portion 265 thereof. Cam slot 444 defines an oblique angle relative to actuation cable 205. Second jaw member 264 has a cam slot 442 located at a proximal portion thereof 263. Cam slot 442 defines an angle with respect to actuation cable 205. Pin 440 is slidably positioned in cam slots 442, 442. As a consequence, first and second jaw members 262, 264 move between open and approximated positions upon longitudinal translation of actuation cable 205. As discussed in detail below, an operator can move first and second jaw members 262, 264 from the open position to the approximated position by moving movable thumb loop 301 toward finger loop 302 (see FIG. 17). As movable thumb loop 301 moves toward finger loop 302, actuation cable 205 translates proximally to urge pin 440 in a proximal direction. When pin 440 is urged proximally, pin 440 slides along cam slots 442, 440, causing first and second jaw members 262, 264 to move toward each other.

With continued reference to FIG. 20, first and second jaw members 262, 264 are pivotally coupled to each other. In certain embodiments, a pivot pin 446 pivotally interconnects first and second jaw members 262, 264. First jaw member 262 defines an opening 448 (FIG. 11A) dimensioned to receive pivot pin 446. Second jaw member 264 defines an opening 450 (FIG. 11A) dimensioned to receive pivot pin 446. As seen in FIGS. 13 and 14, coupling member 222 has a pair of traverse openings 298 configured to receive pivot pin 446 (FIG. 20). Longitudinal tracks 202 engage pivot pin 446 and guide the translation of pivot pin 446 during actuation of end effector 260.

FIG. 20 shows (in phantom) articulation cables 240 secured within distal outer tube 220 of articulating section 230. Articulation cables 240 pass through bores 224 (FIG. 13) of articulation links 232, 234 until reaching distal outer tube 220. In some embodiments, a ferrule or crimp 452 is attached to the distal end 454 of each articulation cable 240. (See also FIGS. 11 and 15). Ferrules 452 (shown in phantom) help retain distal ends 454 of articulation cables 240 within distal outer tube 220. As discussed above, distal outer tube 220 is operatively coupled with an articulation link 234. Articulation links 232, 234 are operatively coupled to each other. Such connection allows articulating section 230 to articulate relative to longitudinal axis "X" (FIG. 2). It is envisioned that the degrees of motion of articulating section 230 is directly proportional to the number of articulation links 232, 234. Articulating section 230 includes a most-proximal link 496. Most-proximal articulation link 496 is substantially similar to articulation links 232, 234. However, most-proximal articulation link 496 includes an extension 498 protruding proximally. Extension 498 is adapted to be securely received within distal end 214 of endoscopy assembly 200.

Referring to FIG. 21, actuation cable 205 is operatively connected to movable thumb loop 301. Alignment tube 207 surrounds a portion of actuation cable 205 extending from movable thumb loop 301 to rotation wheel 303. Handle assembly 300 further includes a proximal torque tube 456 surrounding a portion of actuation cable 205 extending from rotation wheel 303 to articulation cable plate 311 (see also FIG. 11A). Proximal torque tube 456 is partially positioned within an annular hub 310. Annular hub 310 is partially positioned inside articulation cable plate 311 and includes an elongate section 458 and a cable holding section 460. Elongate section 458 of annular hub 310 is at least partially positioned within elongate portion 414 of articulation cable plate 311 and defines a bore 462 dimensioned to receive actuation cable 205 and proximal torque tube 456. Cable holding section 460 includes a plurality of recesses 464 (FIG. 11A) configured to accommodate articulation cables 240 and an cavity 466 leading to bore 462 of elongate section 458. Another proximal torque coil 468 is partially positioned in cavity 466 and surrounds a portion of actuation cable 205 extending from elongate section 458 to cable holding portion 460 of annular hub 310 (see also FIG. 11A). In certain embodiments, proximal torque coil 468 is made of a flexible material. In several embodiments, proximal torque coil 468 is (wholly or partly) made of a shape-memory material such Nickel Titanium Alloy. In some embodiments, proximal torque coil 468 is made (wholly or partly) of a stainless steel torque coil sold by ASAHI INTECC CO., LTD. Cable holding section 460 further includes an elastic wall 476 covering cavity 466. Elastic wall 476 has a slit 478 (FIG. 11A) that allows passage of proximal torque coil 468 through elastic wall 476. Articulation lock ring 400 encircles at least a portion of annular hub 310. As discussed above, articulation lock ring 400 includes a plurality of locking fingers 402. Each locking finger 402 includes a detent 470 for engaging an inner surface 472 of cup 332. As explained below, inner surface 472 of cup 332 defines a plurality of cavities 474 (FIG. 26) each adapted to retain a detent 470. When detents 474 are placed in cavities 474, end effector 260 (FIG. 11A) is maintained in the neutral position.

In an alternate embodiment, rotating wheel 303 in a first direction causes actuation cable 205 to rotate in the same direction, as indicated by arrows "A". Upon rotation of actuation cable 205 in the first direction, end effector 260 rotates in the same direction, as indicated by arrows "B." For example, a clockwise rotation of rotation wheel 303 with respect to housing 340 causes end effector 260 to rotation in a clockwise direction as well.

Figure 24:
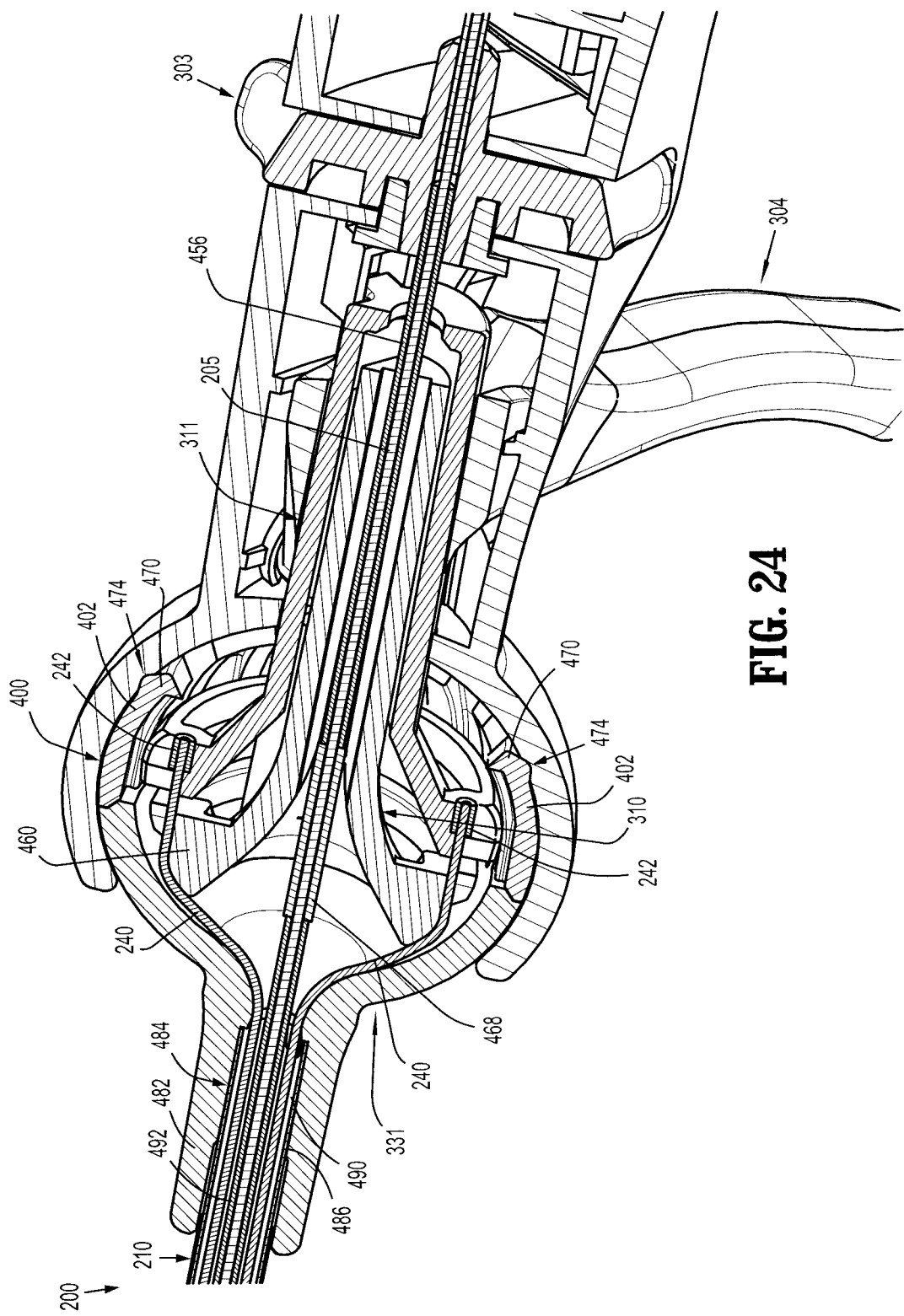
FIG. 24 is a perspective cutaway view of the handle assembly of the surgical device of FIG. 1.
Figure 25:
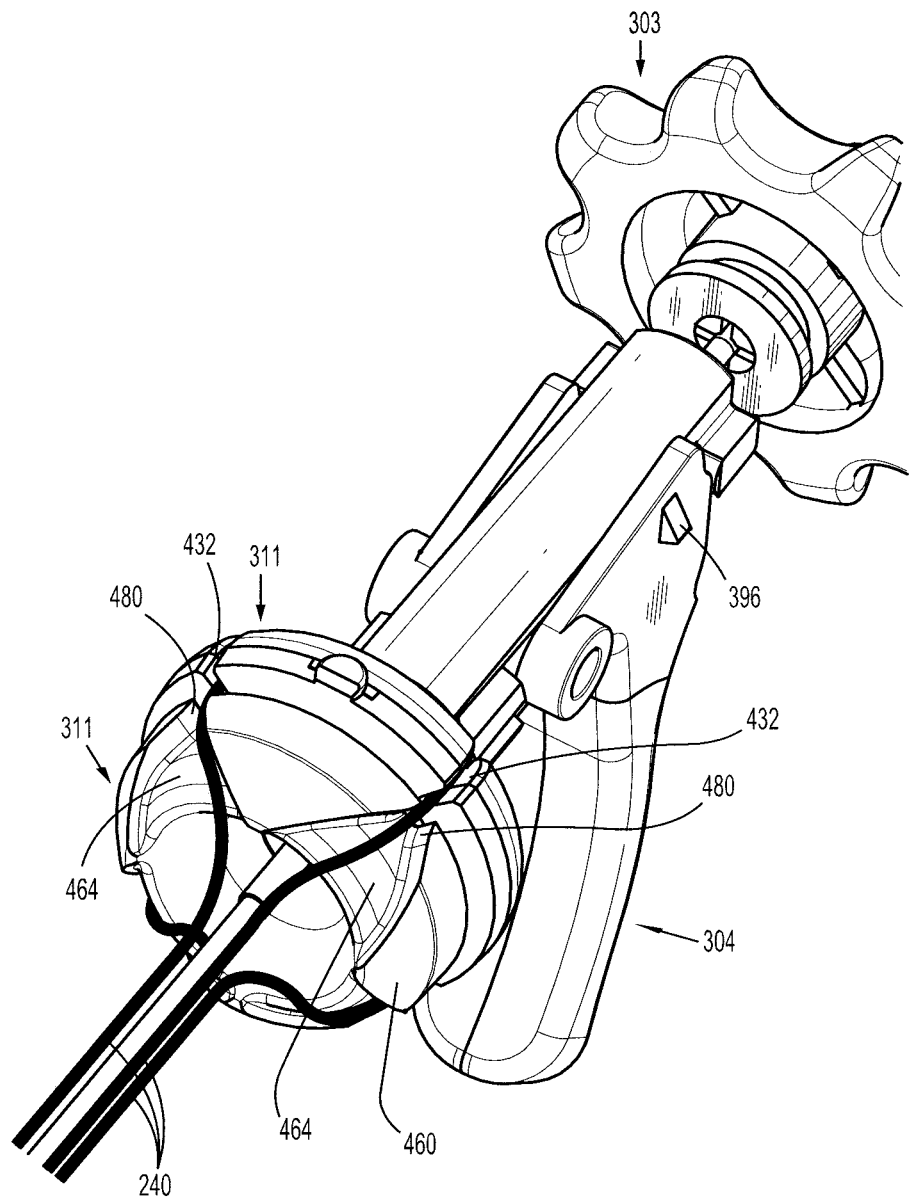
FIG. 25 is a perspective view of a portion of the articulation mechanism of the surgical device of FIG. 1.

With reference to FIGS. 24 and 25, articulation cables 240 are connected to articulation cable plate 311 through ferrules 242. Ferrules 242 are positioned in channels 432 (FIG. 25) of articulation cable plate 311. As a result, articulation cables 240 extend distally from channels 432 of articulation cable plate 311. Channels 432 are aligned with openings 480 (FIG. 25) defined around the perimeter of cable holding section 460. Each opening 480 leads to a recess 464 (FIG. 25) of cable holding section 460. Accordingly, each articulation cable 240 passes through a channel 432, an opening 480, and a recess 464. In certain embodiments, recesses 464 have a triangular profile. Articulation cables 240 also pass through ball 331 and endoscopic assembly 200, as shown in FIG. 24.

With continued reference to FIG. 24, ball 331 includes a distal tube 482 extending distally therefrom. Distal tube 482 defines a bore 484 dimensioned to receive a portion of elongate outer tube 210 and a portion of an elongate inner tube 486 of endoscopic assembly 200. Elongate outer tube 210 defines a bore 488 (FIG. 11A) configured to receive elongate inner tube 486. In turn, elongate inner tube 486 defines a bore 490 adapted to receive actuation cable 205, articulation cables 240, and a distal torque tube 492. Distal torque tube 492 surrounds a portion of actuation cable 205 extending from ball 331 to distal end 214 of endoscopic assembly 200 (see FIG. 20).

Figure 26:
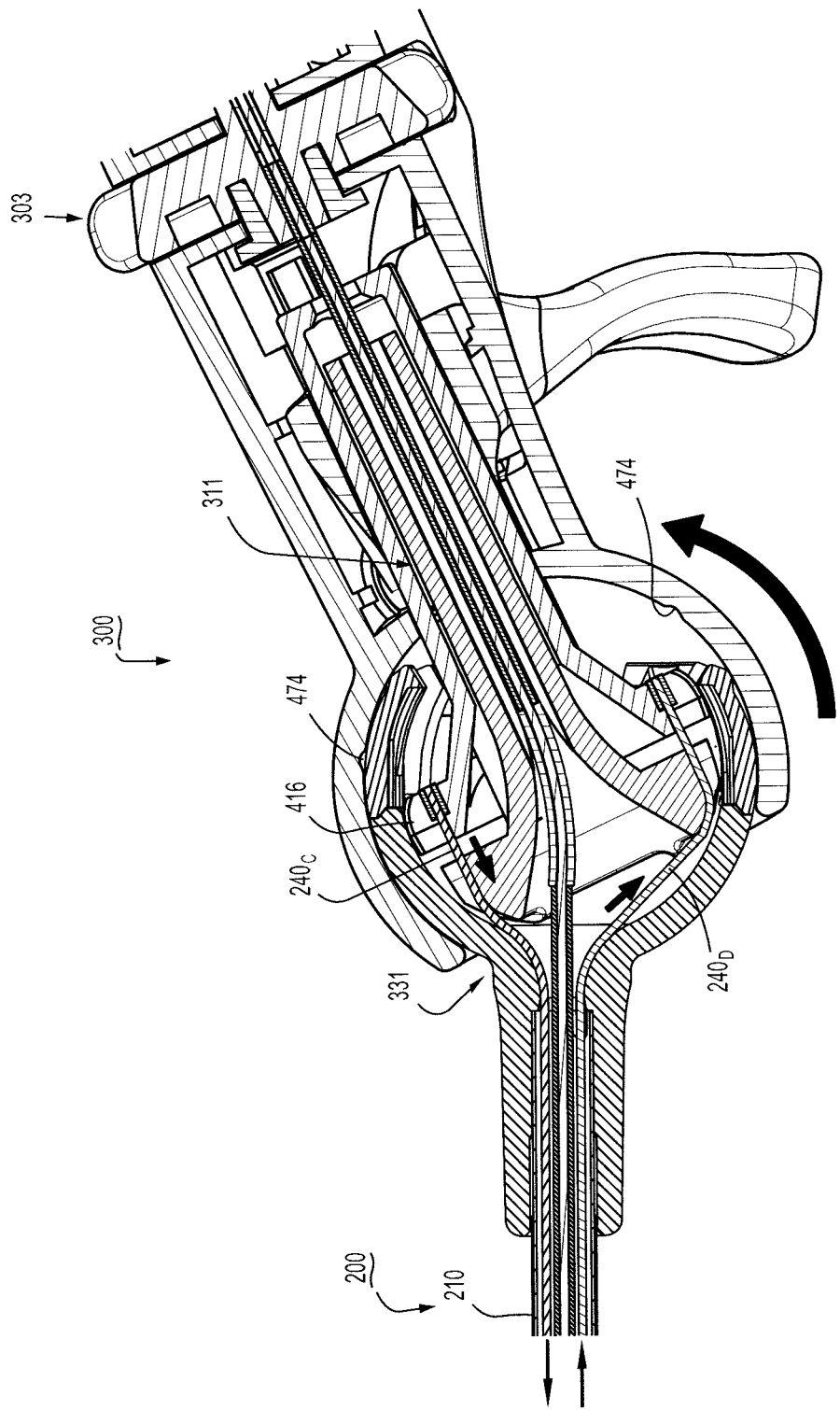
FIG. 26 is a side cross-sectional view of articulation mechanism of the surgical device of FIG. 1, showing a cup moving upwardly relative to a ball of the handle assembly.
Figure 27:
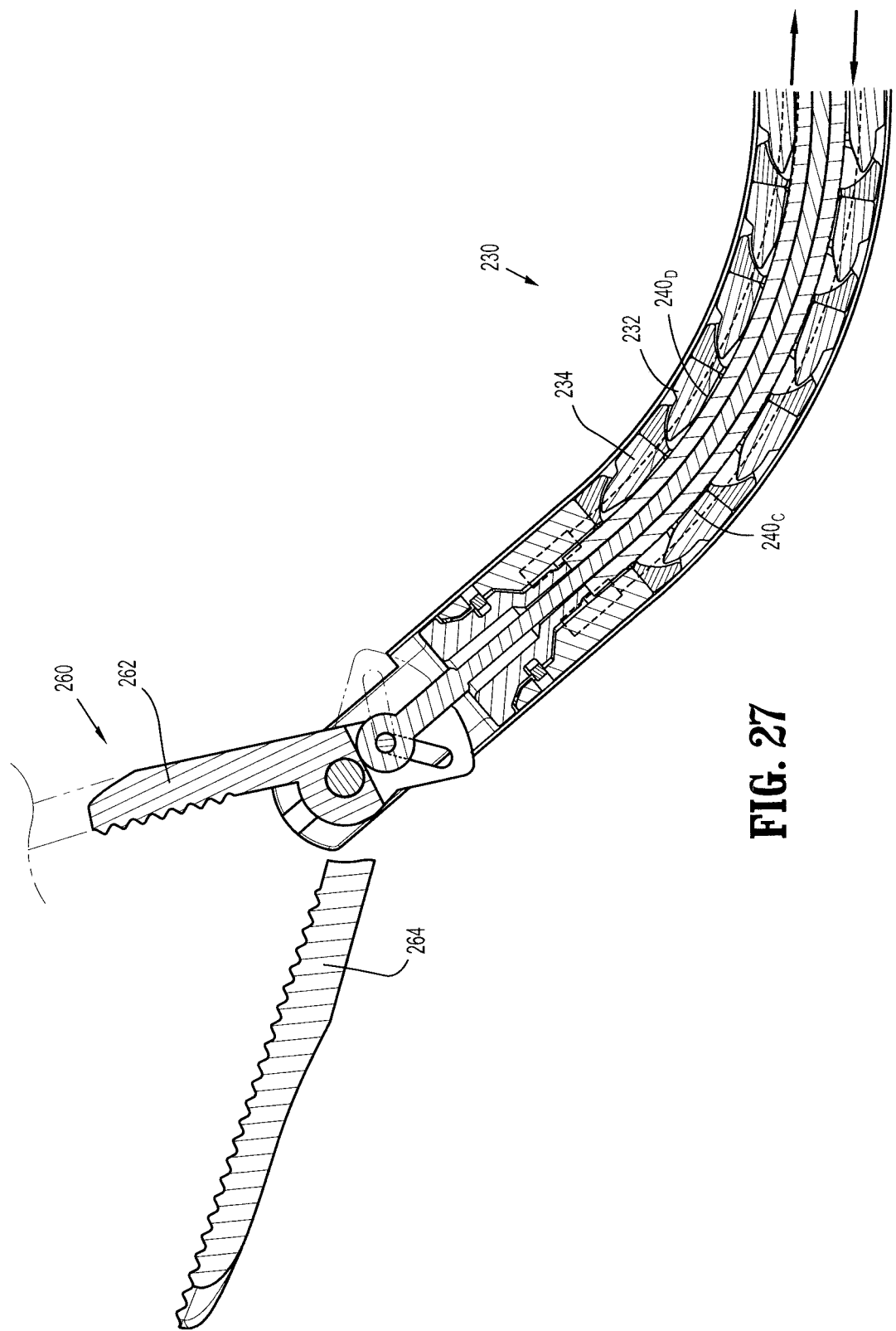
FIG. 27 is a side cross-sectional view of the end effector and the articulation section of the surgical device of FIG. 1, showing the articulating section in an articulated position.

Referring to FIGS. 26 and 27, surgical device 100 allows an operator to articulate articulating section 230 relative to longitudinal axis "X" (FIG. 2) with only one hand. In use, the operator grabs handle assembly 300 with one hand. For example, the operator may place the thumb in movable thumb loop 301 (FIG. 9) and some of the other fingers in finger loop 302 (FIG. 9). Once the operator has grabbed handle assembly 300, the operator moves the wrist to articulate handle assembly 300 relative to elongate outer tube 210 and ball 331. The operator may articulate handle assembly in any direction. FIG. 26, for example, shows handle assembly 300 articulated upwardly with respect to the elongate outer tube 210 (see also FIG. 3). Handle assembly 300, however, may be articulated downwardly or laterally, as shown in FIG. 5. Regardless of the articulation direction, articulating handle assembly 300 with respect to elongate outer tube 210 causes the articulation of articulating section 230, as seen in FIGS. 3 and 5. Articulating section 230 mirrors the movement of handle assembly 300 and articulates relative to elongate outer tube 210 in the same direction as handle assembly 300.

For instance, when the operator articulates handle assembly 300 upwardly with respect to elongate outer tube 210, one articulation cable $240_D$ moves proximally while another articulation cable $240_C$ moves distally. As a results, articulation cable $240_D$ tightens, while articulation cable $240_C$ slacks. In particular, articulation cable plate 311 moves along with handle assembly 300 upon articulation of handle assembly 300 while ball 331 remains stationary relative to elongate outer tube 210. Since articulation cable plate 311 is attached to articulation cables 240, moving articulation cable plate 311 causes articulation cables 240 to move. When articulation cable plate 311 is slanted upwardly relative to ball 331, an articulation cable $240_C$ move distally, while articulation cable $240_D$ moves proximally, as depicted in FIG. 26.

As seen in FIG. 27, the combination of a proximal motion by one articulation cable $240_D$ and the distal motion by articulation cable $240_C$ causes articulating section 230 to articulate upwardly relative to longitudinal axis "X" (FIG. 2). As explained above, articulation cables $240_C$, $240_D$ change positions along elongate outer tube 210. (See FIGS. 18 and 19). Although articulation cable 240$_C$ is positioned above articulation cable 240$_D$ at the proximal end 212 (FIG. 2) of elongate outer tube 210, articulation cables 240$_C$, 240$_D$ switch positions at some point along elongate outer tube 210. As a result, articulation cable 240$_C$ is positioned below articulation cable 240D at the distal end 214 (FIG. 2) of elongate outer tube 210 and in articulating section 230 (FIG. 27). Therefore, a distal translation of articulation cable 240$_C$ allows articulation cable 240$_C$ to slack, thereby loosening a lower portion of articulating section 230. Conversely, a proximal translation of articulation cable 240$_D$ causes tightening on articulation cable 240$_D$, compressing an upper portion articulating section 230. As a result of the compression of an upper portion of articulating section 230, articulating section 230 articulates upwardly relative to longitudinal axis "X" (FIG. 2). The operator may similarly articulate articulating section 230 downwardly or laterally by moving handle assembly 300 with respect to longitudinal axis "X" (FIG. 2). Upon movement of handle assembly 300 with respect to longitudinal axis "X," articulating section 230 articulates in the same direction as handle assembly 300.

Figure 28:
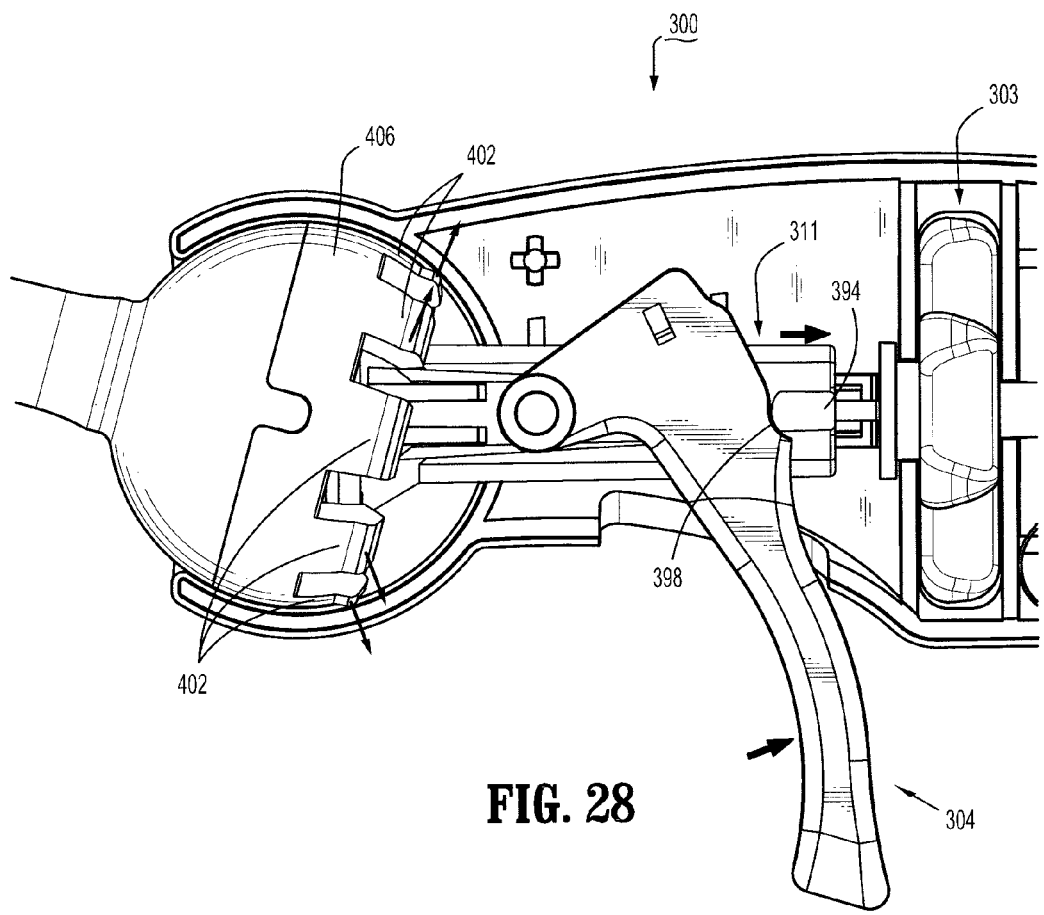
FIG. 28 is a side cutaway view of a portion of the articulation mechanism of the surgical device of FIG. 1, showing an articulation lock trigger being actuated.
Figure 29:
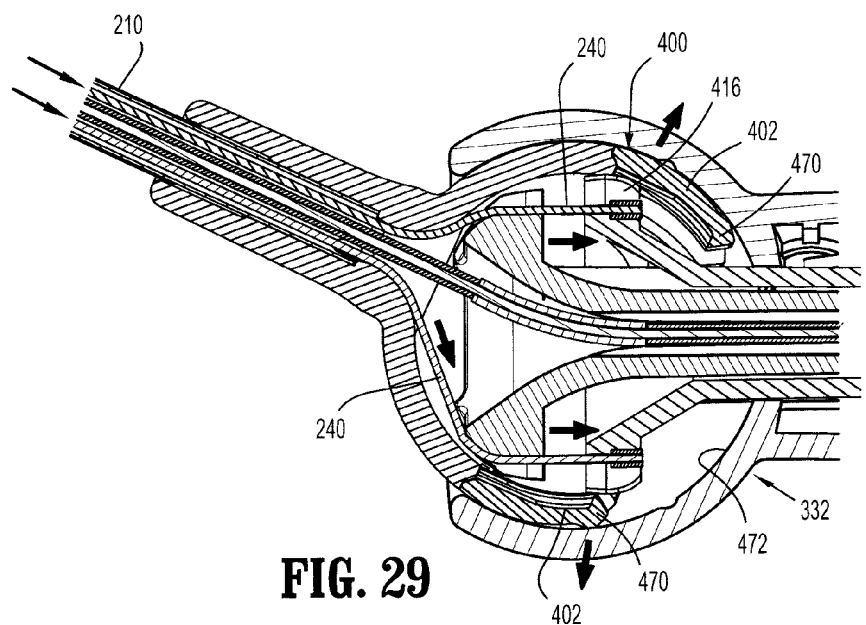
FIG. 29 is a side cross-sectional view of a portion of the articulation mechanism of the surgical device of FIG. 1, depicting articulation cables moving proximally in response to an actuation of the articulation lock trigger shown in FIG. 28.

Referring to FIGS. 28 and 29, the operator can fix the position of articulating section 230 by actuating articulation lock trigger 304. To actuate articulation lock trigger 304, the operator moves articulation lock trigger 304 toward rotation wheel 303, as shown in FIG. 28. Upon actuation of articulation lock trigger 304, detent recess 398 engages detent 394 of articulation cable plate 311, urging articulation cable plate 311 in a proximal direction. As articulation cable plate 311 moves proximally, cable engaging portion 416 of pushes fingers 402 of articulation lock ring 400 outwardly toward inner surface 472 of cup 332. When fingers 402 flex outwardly, detents 470 of fingers 402 frictionally engage inner surface 472 of cup 322, thereby locking the position of handle assembly 300 with respect to elongate outer tube 210 and ball 331. In addition, the proximal translation of articulation cable plate 311 causes all articulation cables 240 to move proximally. As a consequence of this proximal motion, all articulation cables 240 are tightened, compressing articulation links 232, 234 together. Therefore, the compressed articulation links 232, 234 fix the position of articulating section 230 (FIG. 27) relative to elongate outer tube 210.

Figure 30:
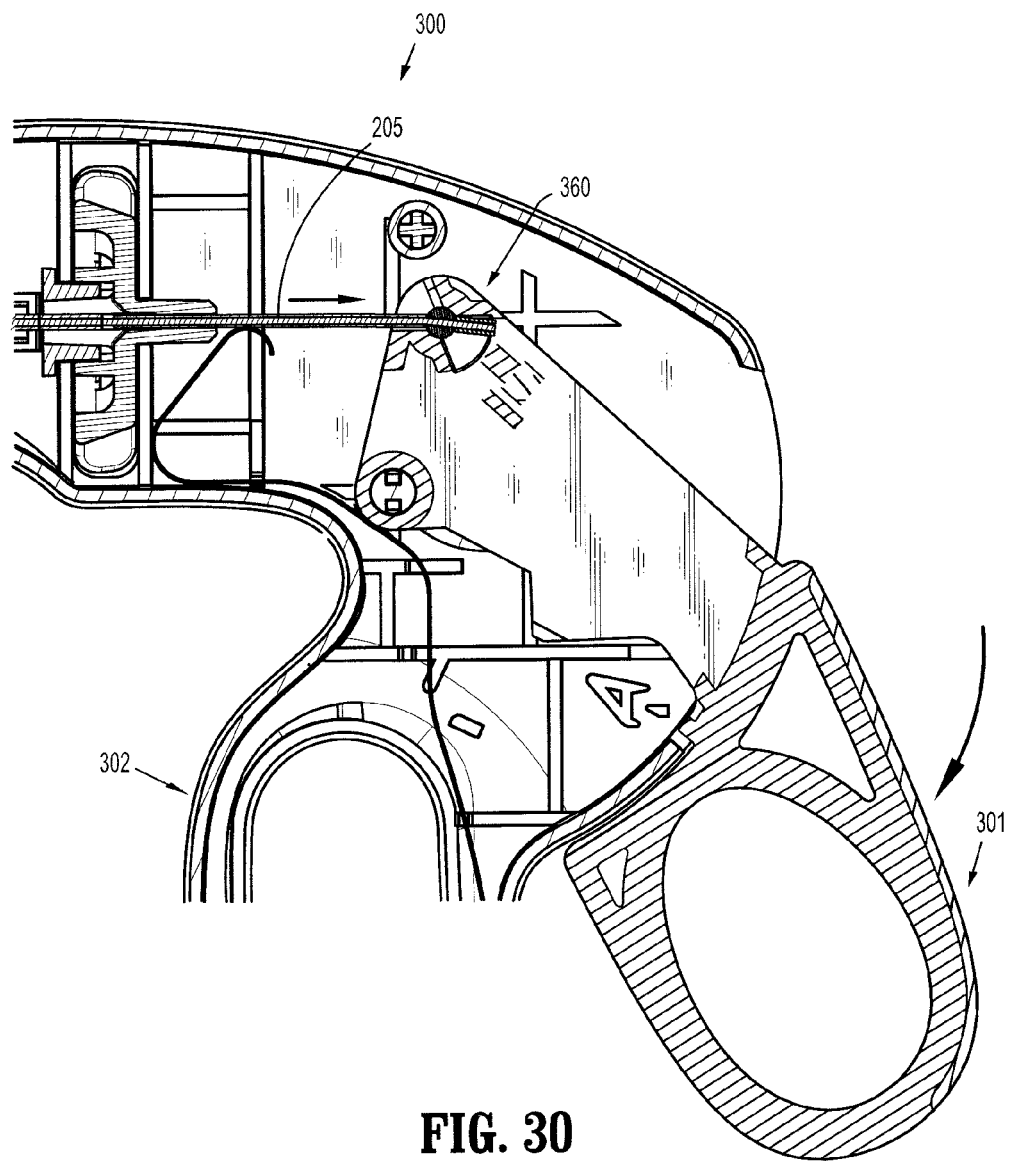
FIG. 30 is a side cross-sectional view of a portion of the handle assembly of the surgical device of FIG. 1, showing a movable thumb loop being actuated.

With reference to FIGS. 30 and 31, the operator can move first and second jaw members 262, 264 between an open position (FIG. 27) and an approximated position (FIG. 31) by actuation of movable thumb loop 301. To actuate end effector 260, the operator moves movable thumb loop 301 toward finger loop 302, as shown in FIG. 30. Since distal end portion 360 of movable thumb loop 301 is operatively connected to actuation cable 205, the actuation of movable thumb loop 301 causes the proximal translation of actuation cable 205. As actuation cable 205 moves proximally, coupling member 436, which interconnects end effector 260 and actuation cable 205, urges pin 440 proximally. The proximal motion of pin 440 along cam slots 442, 444 urges first and second jaw members 262, 264 toward each other. An operator may initial place tissue between first and second jaw members 262, 264 while end effector 260 is in the open position and then move first and second jaw members 262, 264 to the approximated position to clamp the tissue.

FIGS. 32 and 33 show an embodiment of surgical device 100 substantially similar to the embodiments depicted in FIGS. 1-4, except for end effector 1260. End effector 1260 includes first and second shearing blades 1262, 1264 configured to mechanically or electromechanically cut tissue. First and second shearing blades 1262, 1264 are electrically isolated from one another and are adapted to move between an open position and an approximated position.

Figure 34:
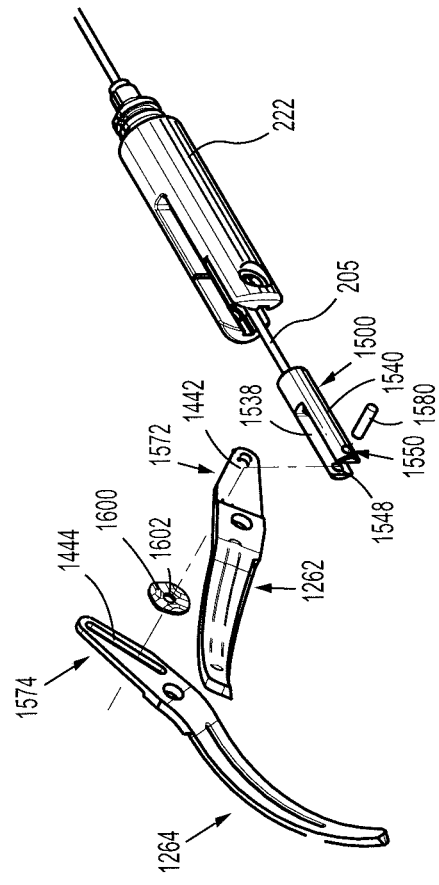
FIG. 34 is a perspective exploded view of the end effector of the surgical device of FIG. 32.
Figure 35:
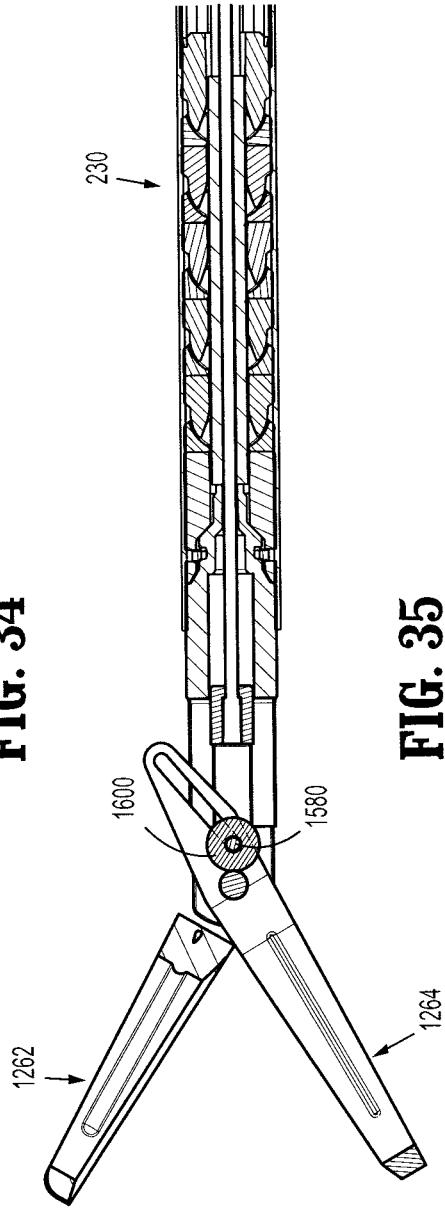
FIG. 35 is a side cross-sectional view of the articulating section and the end effector of the surgical device of FIG. 32.

With reference to FIGS. 34 and 35, although coupling member 222 connects articulating section 230 to end effector 1260, end effector 1260 additionally includes a clevis coupler 1500. Clevis coupler 1500 is attached to actuation cable 205 and includes two legs 1538, 1540 extending distally therefrom. First and second legs 1538, 1540 define a space therebetween dimensioned to receive proximal portions 1572, 1574 of first and second shearing blades 1262, 1264. Each leg 1538, 1540 defines a hole 1548, 1550 adapted to receive a pin 1580. Pin 1580 is also configured to be slidably received in cam slots 1442, 1444 of first and second shearing blades 1262, 1264. Cam slot 1442 is defined along a proximal portion 1572 of shearing blade 1262, whereas cam slot 1444 is defined along a proximal portion 1574 of shearing blade 1264. A disk made 1600 of electrically insulating material electrically isolates shearing blades 1262, 1264 from each other. As seen in FIG. 34, disk 1600 is positioned between first and second shearing blades 1262, 1264 and defines a hole 1602 configured to receive pin 1580.

Figure 38:
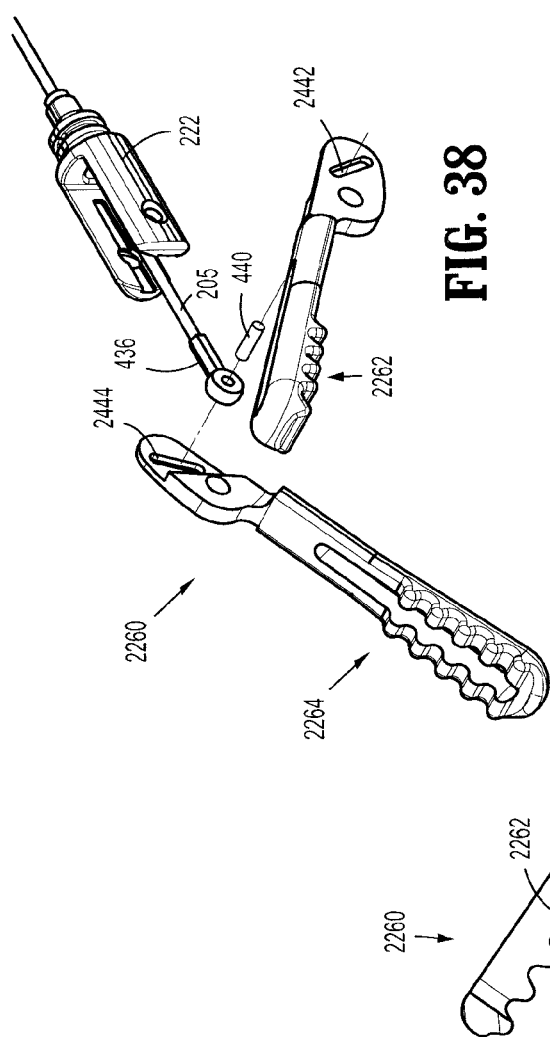
FIG. 38 is a perspective exploded view of the end effector of the surgical device of FIG. 36.

FIGS. 37 and 38 depict another embodiment of surgical device 100. The structure and operation of this embodiment is substantially similar to the embodiment shown in FIGS. 1-5. This embodiment of surgical device 100 includes an end effector 2260 configured for grasping tissue. End effector 2260 includes first and second grasping forceps 2262, 2264 configured to grasp tissue. Although the drawings of this embodiment show surgical device 100 without a post 350 (FIG. 10A), this embodiment of surgical device 100 may include a post 350 for electrically coupling end effector 2226 to a generator. First and second grasping forceps 2262, 2264 are configured to move between an open position and an approximated position. Each of the first and second grasping forceps 2262, 2264 includes a tissue engaging surface 2266, 2268. Both tissue engaging surfaces 2266, 2268 includes a plurality of teeth 2272, 2274 for engaging tissue.

Figure 39:
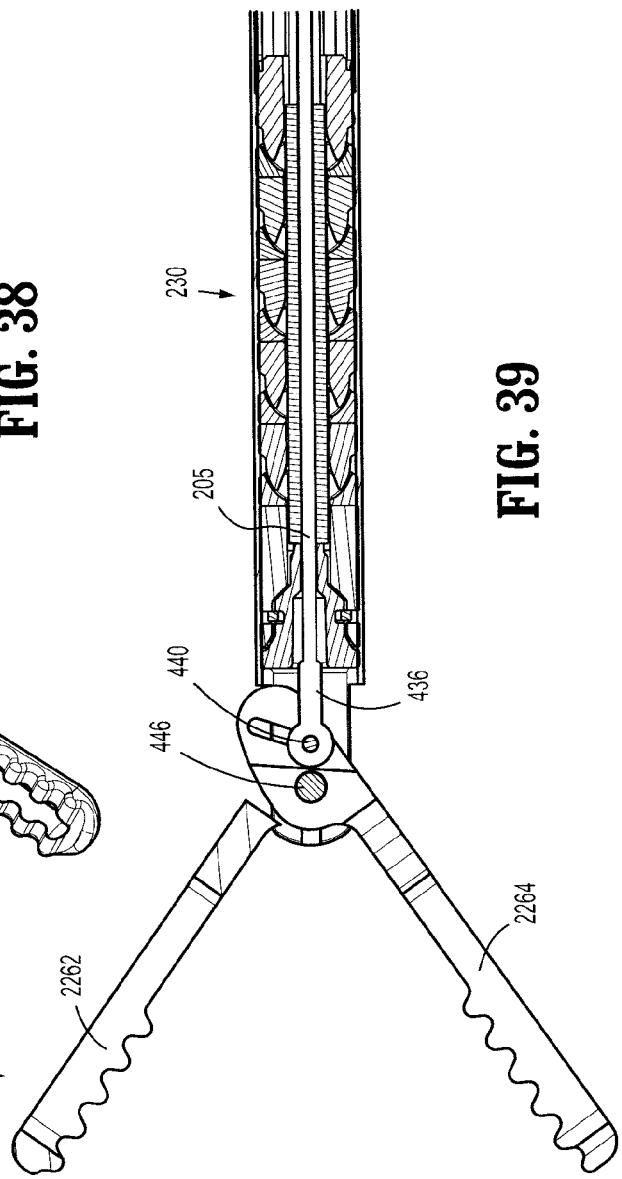
FIG. 39 is a side cross-sectional view of an articulating section and the end effector of the surgical device of FIG. 36.
Figure 40:
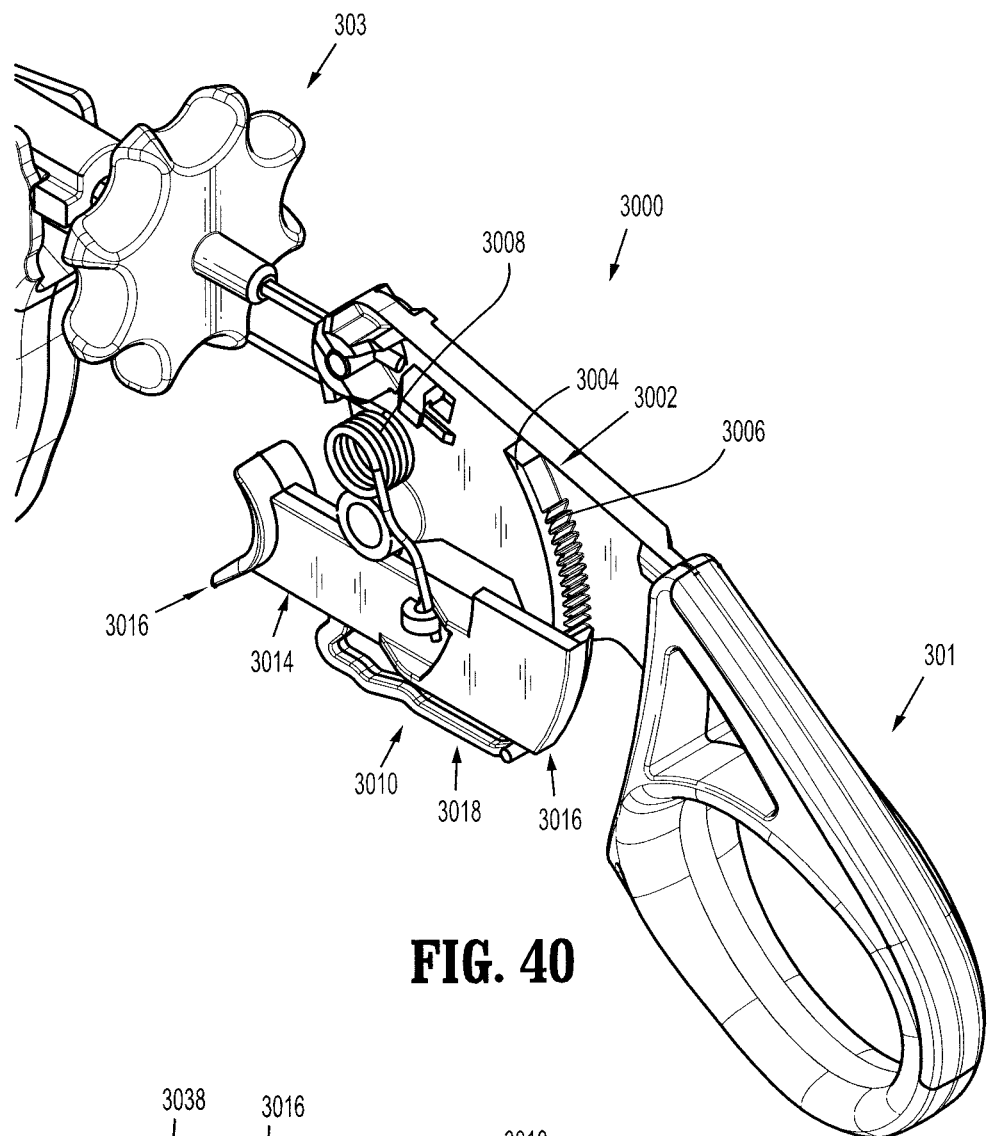
FIG. 40 is a perspective view of a locking mechanism for any of the embodiments of the surgical device shown above.
Figure 41:
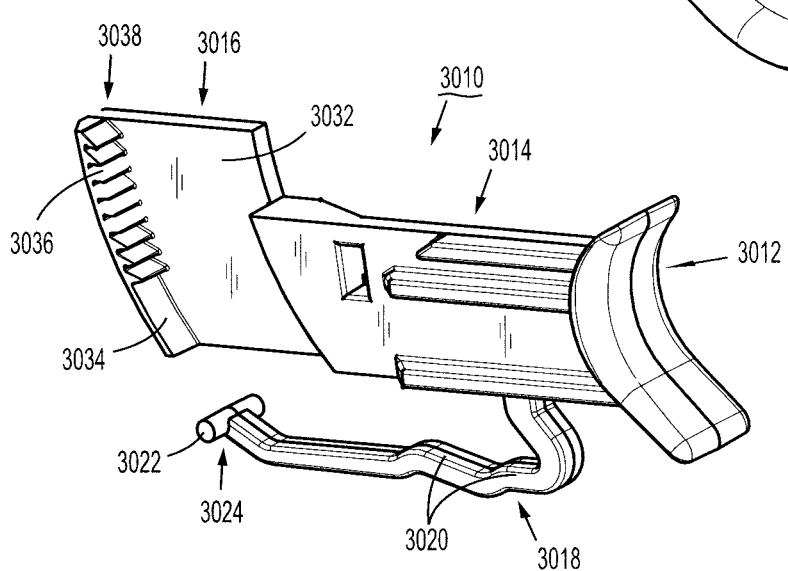
FIG. 41 is a perspective view of a release assembly of the locking mechanism of FIG. 40.

With reference to FIGS. 38 and 39, first and second grasping forceps 2262, 2664 are pivotally connected to each other by pivot pin 446. End effector 2260 is operatively coupled to actuation cable 205 through coupling 436 and pin 440. Each of the first and second grasping forceps 2262, 2264 includes cam slots 2442, 2444 adapted for slidably receiving pin 440. Such connection allows first and second grasping forceps 2262, 2264 to move to the approximated position upon a proximal motion of actuation cable 205.

Referring to FIGS. 40-43, any of the embodiments of surgical device 100 may include a locking mechanism 3000 for fixing the relative position of first and second jaw members 262, 264. As discussed above, movable thumb loop 301 is operatively coupled to first and second jaw members 262, 264. In operation, pivoting movable thumb loop 301 toward finger loop 301 causes first and second jaw members 262, 264 to move from the open position and the approximated position. (See FIGS. 30 and 31). Thus, maintaining movable thumb loop 301 close to finger loop 302 would keep first and second jaw members 262, 264 in the approximated position. In use, locking mechanism 3000 can maintain thumb loop 301 close to finger loop 302 to fix first and second jaw members 262, 264 in the approximated position. In some embodiments, locking mechanism 3000 includes a first ratchet assembly 3002 attached to the movable thumb loop 301. Specifically, first ratchet assembly 3002 is attached to the lateral wall of a portion of movable thumb loop located inside handle assembly 300. First ratchet assembly 3002 includes a curved column 3004 and a plurality of teeth 3006 extending proximally from curved column 3004. Each tooth 3006 is angled upwardly relative to movable thumb loop 301.

Locking mechanism 3000 further includes biasing member 3008, such as a spring, secured to a portion of movable thumb loop 301 located within handle assembly 300 and operatively coupled to a release assembly 3010. Biasing member 3008 biases release assembly 3010 in a distal direction. In the depicted embodiment, biasing member 3008 is a torsion spring. It is contemplated, however, that biasing member 3008 may be any apparatus or means suitable for biasing release assembly 3010 distally.

Release assembly 3010 includes a trigger 3012 adapted to receive a finger, an elongate section 3014 extending proximally from trigger 3012, a second ratchet assembly 3016 configured to securely engage first ratchet assembly 3002, and a guiding bar 3018 protruding from a lower portion of elongate section 3014.

Guiding bar 3018 has camming surfaces 3020 and transverse pin 3022 disposed at a proximal end 3024 thereof. Camming surfaces 3020 are configured to slidably engage projections 3026, 3028 of handle assembly 300 (FIGS. 42 and 43) to guide the translation of release assembly 3010 through handle assembly 300. Transverse pin 3022 is configured to engage a mechanical stop 3030 disposed inside handle assembly 300 to prevent, or at least inhibit, further proximal advancement of release assembly 3010.

As discussed above, release assembly 3010 also includes a second ratchet assembly 3016 configured to engage first ratchet assembly 3002. Second ratchet assembly 3016 includes a wall 3032 extending proximally from elongate section 3014 and a curved column 3034 positioned along a proximal end 3038 of wall 3032. A plurality of teeth 3036 protrude distally from at least a portion of curved column 3034. Teeth 3036 are adapted to securely engage teeth 3006 of first ratchet assembly 3002. In some embodiments, teeth 3036 are angled downwardly with respect to movable thumb loop 301. When teeth 3036 of second ratchet assembly 3016 engage teeth 3006 of first ratchet assembly 3002, the position of movable thumb loop 301 is fixed relative to finger loop 302. (See FIG. 42).

Figure 42:
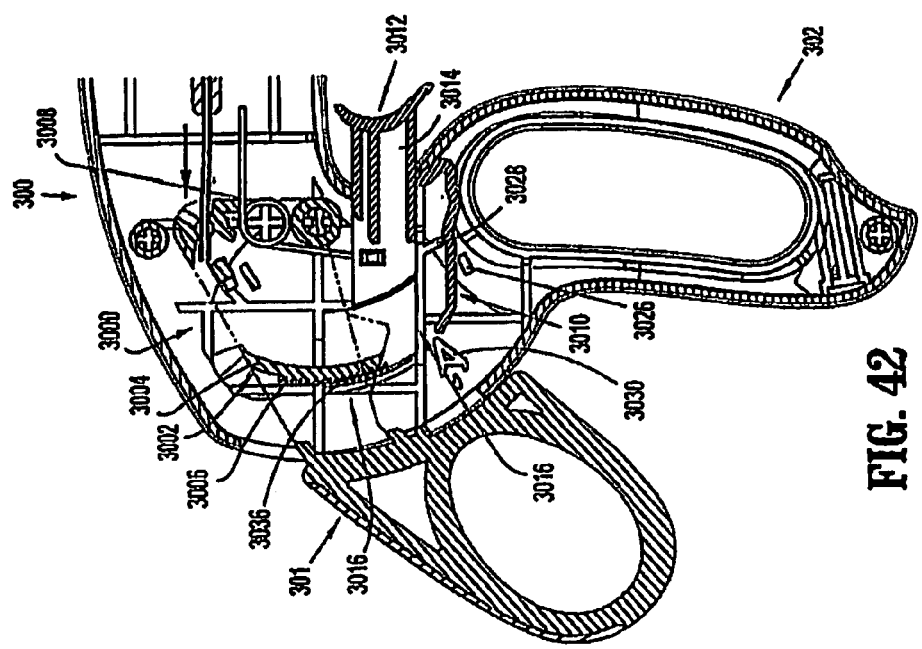
FIG. 42 is a side cross-sectional view of the locking mechanism of FIG. 40 in a locked position.

In operation, an operator can utilize locking mechanism 3000 to fix the relative position of first and second jaw members 262, 264 (FIG. 31). Initially, the operator moves movable thumb loop 301 toward finger loop 302 to move first and second jaw members 262, 264 (FIG. 31) toward the approximated position. As movable thumb loop 301 moves toward finger loop 302, teeth 3006 of first ratchet assembly 3002 engage teeth 3036 of second ratchet assembly 3016. The orientation of teeth 3006 and teeth 3036 precludes, or at least hinders, movable thumb loop 301 from moving away from finger loop 302 while allowing movable thumb loop 301 to move further toward finger loop 302. As a result, locking mechanism 3000 fixes the position of movable thumb loop 301 relative to finger loop 302, as shown in FIG. 42. Since movable thumb loop 301 is operatively connected to first and second jaw members 262, 264 (FIG. 31), the relative position of first and second jaw members 262, 264 is fixed when locking mechanism 300 fixes the position of movable thumb loop 301 with respect to finger loop 302. Once locking mechanism 300 has locked the position of movable thumb loop 301, the operator may further advance movable thumb loop 301 toward finger loop 302 until first and second jaw members 262, 264 (FIG. 31) reach the approximated position.

Figure 43:
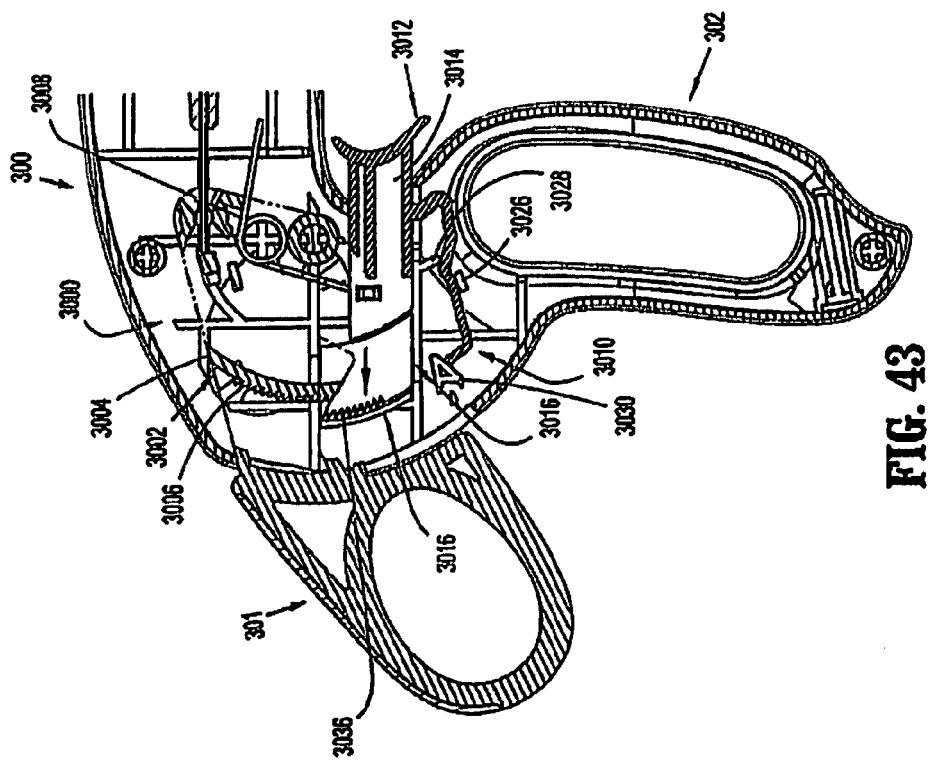
FIG. 43 is a side cross-sectional view of the locking mechanism of FIG. 40 in an unlocked position.

To release movable thumb loop 301, the operator presses trigger 3012 proximally against the influence of biasing member 3008. When trigger 3012 moves proximally, teeth 3036 of second ratchet assembly 3016 move proximally and disengages teeth 3002 of first ratchet assembly 3002. Consequently, movable thumb loop 301 moves away from finger loop 302 under the influence of biasing member 3008, thereby moving first and second jaw members 262, 264 toward the open position, as shown in FIG. 43. (See also FIG. 20).

FIGS. 44-46 show another embodiment of surgical device 100. The operation and structure of this embodiment of surgical device 100 is substantially similar to the embodiments described above. In this embodiment, surgical device 100 includes an end effector 4260 including an electrode assembly 4262. Electrode assembly 4262 includes at least one probe or electrode 4264 adapted to conduct and apply electrosurgical energy to tissue. In the depicted embodiment, electrode assembly 4262 has one probe 4264 having a hook-like shape. Probe 4264, however, may have any suitable shape or configuration. Regardless of its shape, probe 4264 is electrically linked to actuation cable 205 of surgical device 100, as shown in FIG. 46.

With continued reference to FIGS. 44-46, this embodiment of surgical device 100 includes an electrical switch 4700 supported on handle assembly 300. Electrical switch 4700 is configured to set surgical device 100 to one of a number of modes of operation, such as cutting, blending, and/or coagulating. More specifically, electrical switch 4700 is adapted to vary the waveform and/or amount of energy that is delivered from the source of electrosurgical energy to electrode assembly 4262. In several embodiments, electrical switch 4700 has two discrete positions. In a first discrete position, electrical switch 4700 sets surgical device 100 to transmit "a cutting waveform" output to electrode assembly 4262 and, in a second discrete position, electrical switch 4700 sets surgical device 100 to transmit a "coagulating waveform" output to electrode assembly 4262. It is envisioned that electrical switch 4700 may also include some measure of tactile feedback capable of being felt by the operator and/or some measure of audible feedback produced by electrical switch 4700 (e.g., "click" sound).

In addition to electrical switch 4700, surgical device 100 includes an electrical interface or plug 4800 configured to be mechanically and electrically connected to a source of electrosurgical energy such as a generator. Plug 4800 includes a plurality of prongs 4802 adapted to mechanically and electrically coupled plug 4800 to a source of electrosurgical energy. An electrical cable 4804 electrically links plug 4800 with handle assembly 300.

Figure 47:
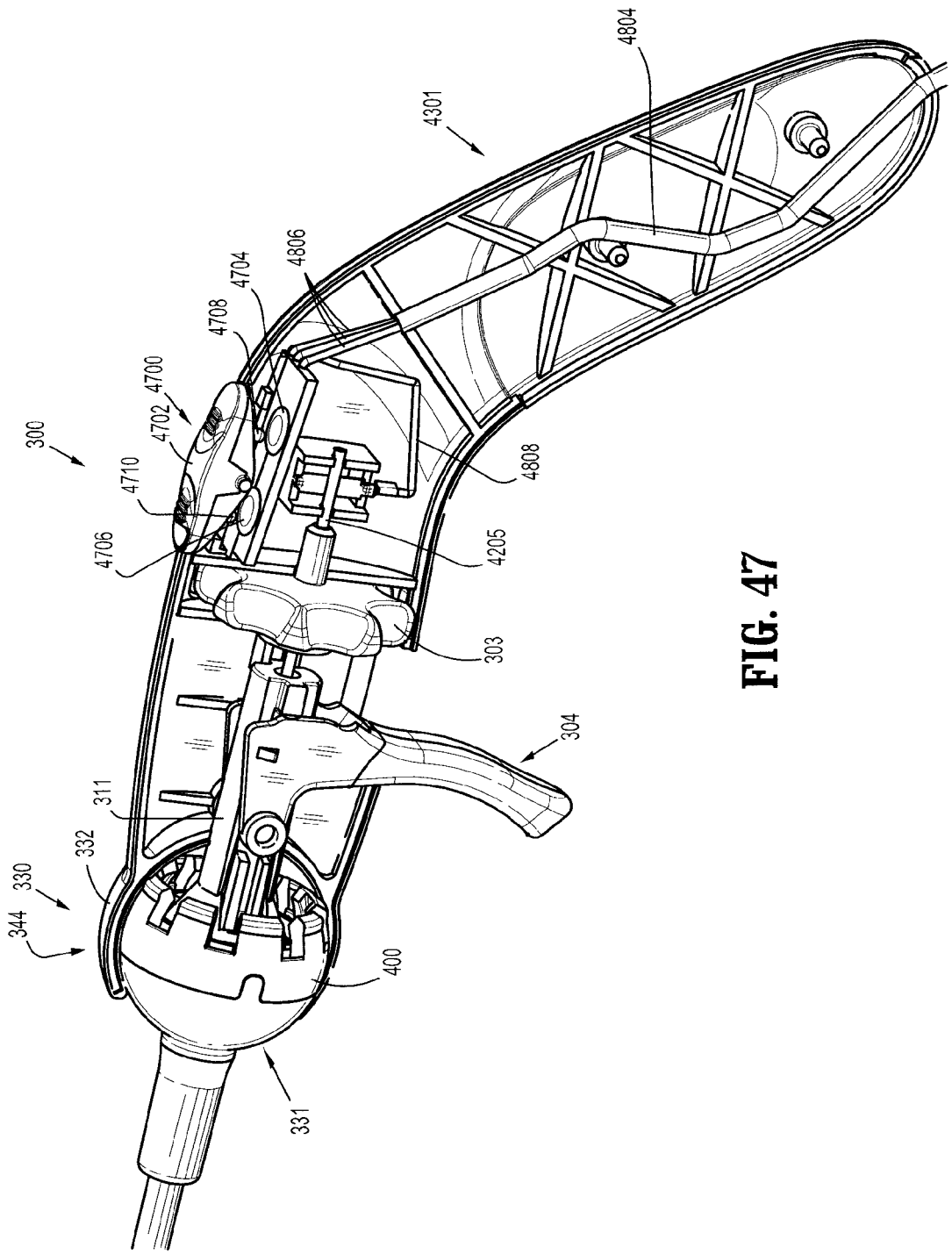
FIG. 47 is a side cutaway view of a handle assembly of the surgical device of FIG. 44.

Referring to FIG. 47, this embodiment of surgical device 100 includes a stationary handle 4301 housing a portion of electrical cable 4804. Electrical cable 4804 encompasses a plurality of electrical wires 4806 configured to transmit electrosurgical energy from a source of electrosurgical energy (not shown). Electrical wires 4806 are electrically coupled to electrical switch 4700.

In the embodiment shown in FIG. 47, electrical switch 4700 includes a button 4702 configured to move between a first position and a second position and first and second transducers 4704, 4706. It is contemplate that transducers 4704, 4706 may be pressure transducers. Button 4702 includes first and second prongs 4708, 4710 extending downwardly toward first and second transducers 4704, 4706. When button 4702 is located in the neutral position, as shown in FIG. 47, first and second prongs 4708, 4710 are not in contact with first and second transducers 4704, 4706. Button 4702, however, may be moved between first and second positions. In the first position, first prong 4708 contacts and applies pressure to first transducer 4704. In response, first transducer 4704 converts this pressure into a signal that is transmitted to the electrosurgical generator (not shown) via electrical wires 4806. In turn, the electrosurgical generator transmits a corresponding amount of electrosurgical energy (such as RF energy) or an appropriate waveform output to electrode assembly 4262. As such, button 4702, in combination with first and second transducers 4704, 4706 allow the operator to control the amount of energy and/or waveform output of the electrosurgical generator (not shown) electrically coupled to surgical device 100. For example, when button 4702 is placed in the first position, a "cutting-type" waveform is selected. Conversely, when button 4702 is placed in the second position, second prong 4710 contacts and applies pressure to second transducer 4706. In turn, second transducer 4706 converts this pressure into a signal that is transmitted to the electrosurgical generator (not shown) via electrical wires 4806. In response to this signal, electrosurgical generator transmits a "cutting-type" waveform output to electrode assembly 4262. Accordingly, the operator can select the therapeutic effect desired by simply moving button 4702 between the first and second positions. It is envisioned that surgical device 100 may be deactivated (i.e., de-energized) when button 470 is in the neutral position.

Handle assembly 300 further includes an electrical wire 4808 electrically linking electrical switch 4700 and inner rod 4205. Inner rod 4205 is made of an electrically conductive material and electrically couples electrode assembly 4262 with an electrosurgical generator (not shown) connected to surgical device 100.

Figure 48:
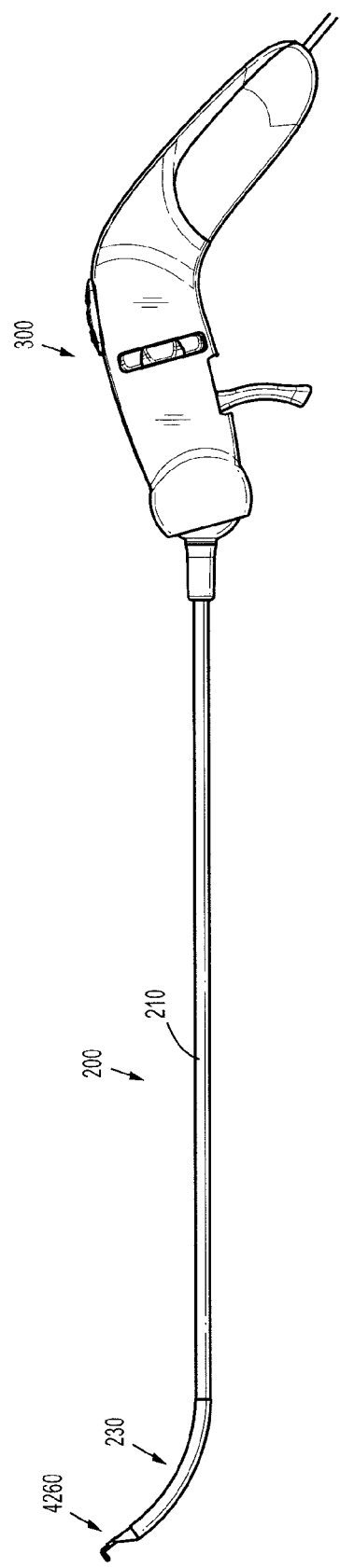
FIG. 48 is a side elevational view of the surgical device of FIG. 44, depicting the articulating section in an articulated position.
Figure 49:
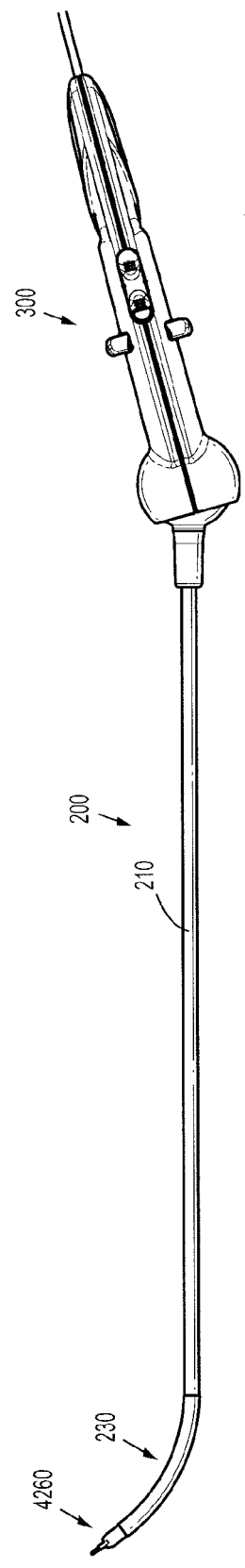
FIG. 49 is a top view of the surgical device of FIG. 44, depicting the articulating section in an articulated position.

With continued reference to FIG. 47, this embodiment of surgical device 100 also includes articulation mechanism 330 operatively associated with articulating section 230 of endoscopic assembly 200. Articulating section 230 is configured to articulate towards a particular direction with respect to elongate outer tube 210 upon movement of handle assembly 300 toward the same direction with respect to elongate outer tube 210, as seen in FIGS. 48 and 49.

Figure 50:
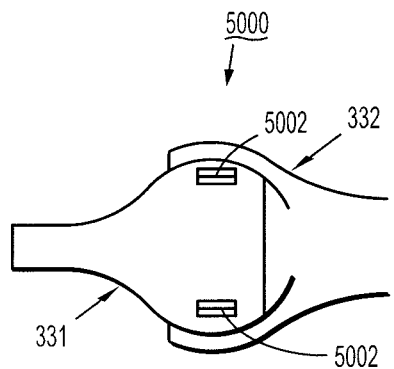
FIG. 50 is a side cutaway view of an embodiment of a straightening mechanism for incorporation in any of the embodiments of the surgical device discussed above.
Figure 51:
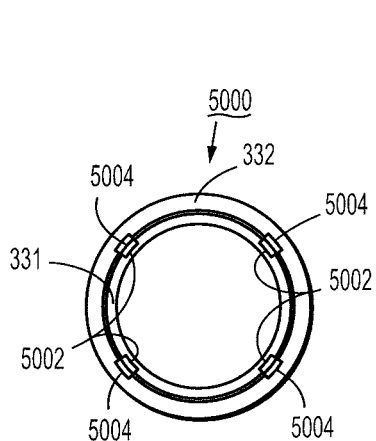
FIG. 51 is a front view of the straightening mechanism of FIG. 50.
Figure 52:
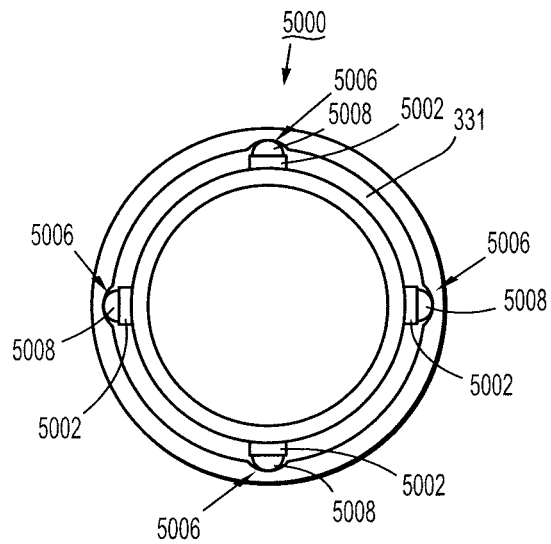
FIG. 52 is a front view of the straightening mechanism of FIG. 50 with detents for securing an articulation mechanism in a neutral position.

Referring to FIGS. 50-51, any of the embodiments of surgical device 100 may include a straightening mechanism 5000 for returning articulating section 230 (FIG. 2) into longitudinal alignment with elongate outer tube 210 (FIG. 2) after articulation. Straightening mechanism 5000 includes a first set of magnets 5002 attached to ball 331 and a second set of magnets 5004 attached to cup 332. It is envisioned that magnets 5002, 5004 may be rear earth magnets 5002. Magnets 5002, 5004 may be permanent magnets or electromagnets. In the embodiments where magnets 5002, 5004 are permanent magnets, magnets 5002, 5004 are oriented so that opposite poles of magnets 5002, 5004 face each other, thus triggering attraction forces. Magnets 5002 are disposed around the periphery of ball 331, whereas magnets 5004 are positioned around an inner surface of cup 331. (See FIG. 51). When articulating section 230 is longitudinal aligned with elongate outer tube 210, magnets 5002 are radially aligned with magnets 5004. The position and orientation of magnets 5002 relative to magnets 5004 trigger attraction forces between them. The attraction forces between magnets 5002, 5004 maintain cup 332 aligned with ball 331. As discussed above, when ball 331 is aligned with cup 332, articulating section 230 is longitudinal aligned with elongate outer tube 210. (See FIG. 2). If cup 332 is moved relative to ball 331 to articulate articulating section 230, the attraction forces of magnets 5002, 5002 draws ball 331 back into alignment with cup 332, as seen in FIG. 2. As seen in FIG. 51, in some embodiments, ball 331 includes detents 5008 attached to each magnets 5002. In turn, cup 332 includes concavities 5006 adapted to securely receive detents 5008. The engagement between detents 5008 and concavities 5006 help secure ball 331 in the neutral position.

Figure 53:
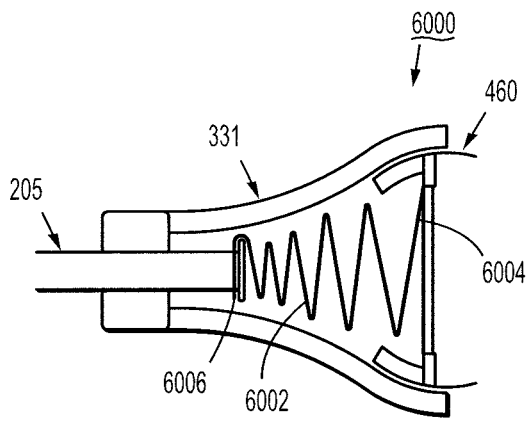
FIG. 53 is side cutaway view of another embodiment of a straightening mechanism with a helix spring for incorporation in any of the embodiments of the surgical device discussed above.

With reference to FIG. 53, any of the embodiments of surgical device 100 may include a straightening mechanism 6000 for returning articulating section 230 (FIG. 2) into longitudinal alignment with elongate outer tube 210 (FIG. 2) after articulation. Straightening mechanism 6000 includes a conical helical spring 6002 positioned within ball 331. Conical helical spring 6002 has a proximal end 6004 attached to cable holding section 460 and a distal end 6006 attached to actuation cable 205. When handle assembly 300 is articulated relative to elongate outer tube 210 (FIG. 3), one side of conical helical spring 6002 is in tension, while the other side of conical helical spring 6002 is in compression, creating a moment that urges handle assembly 300 back to its neutral position (see FIG. 2). As discussed above, when handle assembly 300 is in its neutral position, articulating section 230 is longitudinally aligned with elongate outer tube 210. It is envisioned that conical helical spring 6002 may be pretensioned to increase the moment.

Figure 54:
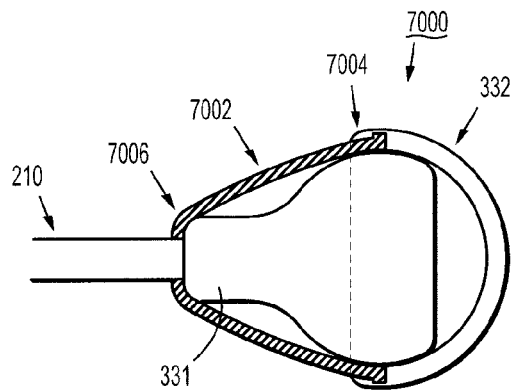
FIG. 54 is a side cross-sectional view of an embodiment of a straightening mechanism including an elastomeric boot for incorporation in any of the embodiments of the surgical device discussed above.

With reference to FIG. 54, any of the embodiments of surgical device 100 may include a straightening mechanism 7000 for returning articulating section 230 (FIG. 2) into longitudinal alignment with elongate outer tube 210 (FIG. 2) after articulation. Straightening mechanism 7000 includes a flexible boot 7002 covering ball 331. It is contemplated that flexible boot 7002 may be made of an elastomeric material or any other suitable material. Flexible boot 7002 has a proximal end portion 7004 attached to cup 332 and a distal end portion 7006 attached to a portion of elongate outer tube 210 located adjacent ball 331. In operation, when cup 332 is moved relative to ball 331, one side of flexible boot 7002 stretches and is in tension, creating a moment that urges ball 331 back to its neutral position (see FIG. 2).

Figure 55:
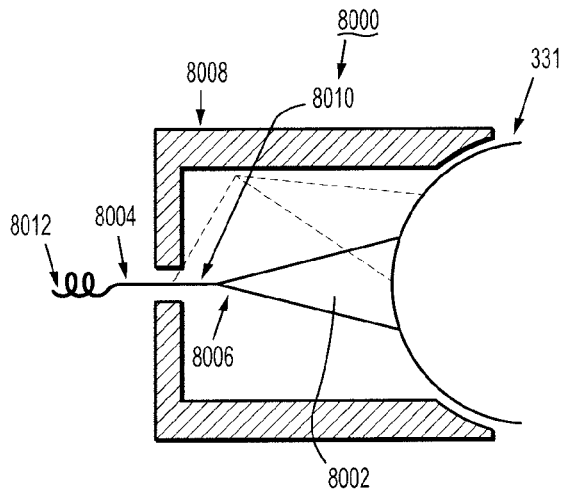
FIG. 55 is a side cross-sectional view of an embodiment of a straightening mechanism having an elastomeric member for incorporation in any of the embodiments of the surgical device discussed above.

With reference to FIG. 55, any of the embodiments of surgical device 100 may include a straightening mechanism 8000 for returning articulating section 230 (FIG. 2) into longitudinal alignment with elongate outer tube 210 (FIG. 2) after articulation. Straightening mechanism 8000 includes a protruding member 8002 extending proximally from ball 331 and an elastic member 8004 attached to a proximal end 8006 of protruding member 8002. Elastic member 8004 has a distal end 8010 attached to protruding member 8002 and a proximal end 8012 attached to articulation cable plate 311 (FIG. 21). A housing 8008 encloses protruding member 8002 and at least a portion of elastic member 8004. In operation, when ball 331 is moved relative to cup 332 (FIG. 21), elastic member 8004 stretches (as shown in phantom). As a result, tension builds up on elastic member 8004. This tension creates a restoring moment that biases ball 331 toward the neutral position. (See FIG. 2).

Figure 56:
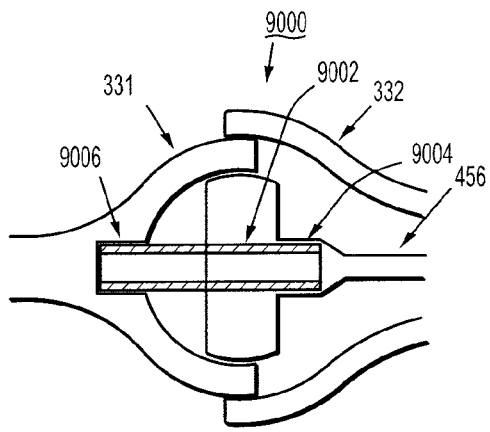
FIG. 56 is a side cross-sectional view of an embodiment of a straightening mechanism having a superelastic member for incorporation in any of the embodiments of the surgical device discussed above.

With reference to FIG. 56, any of the embodiments of surgical device 100 may include a straightening mechanism 9000 for returning articulating section 230 (FIG. 2) into longitudinal alignment with elongate outer tube 210 (FIG. 2) after articulation. Straightening mechanism 9000 includes a tube or rod 9002 made of a material exhibiting superelastic properties. It is envisioned that tube 9002 is substantially resilient. In some embodiments, tube 9002 is wholly or partly made of a shape memory material such as Nitinol. Tube 9002 has a proximal end 9004 and a distal end 9006. Proximal end 9004 of rod 9002 is attached to proximal torque tube 456, while distal end 9006 of rod 9002 is fixed to ball 331. When ball 331 is articulated with respect to cup 332, tube 9002 articulates and creates a moment that biases ball 331 towards its neutral position (see FIG. 2). In some embodiments, tube 9002 corresponds to proximal torque coil 468 shown in FIG. 24.

Figure 57:
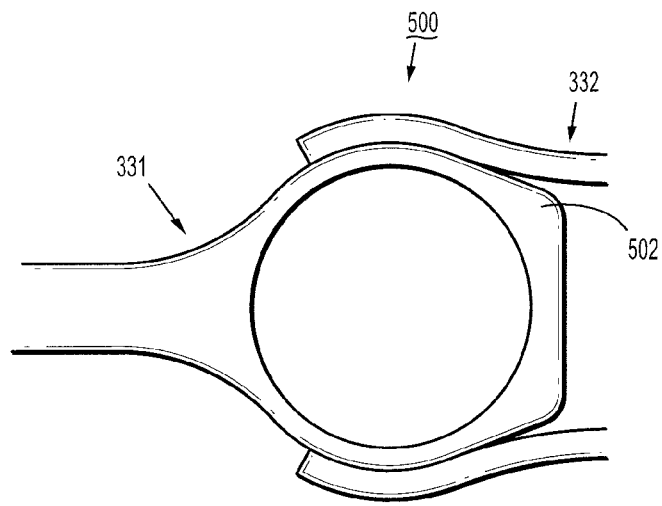
FIG. 57 is side cut-away view of an embodiment of a straightening mechanism with an elongate ball for incorporation in any of the embodiments of the surgical device discussed above.

With reference to FIG. 57, any of the embodiments of surgical device 100 may include a straightening mechanism 500 for returning articulating section 230 (FIG. 2) into longitudinal alignment with elongate outer tube 210 (FIG. 2) after articulation. In straightening mechanism 500, ball 331 includes an elongate portion 502 extending proximally therefrom. When ball 331 is moved relative to cup 332, elongate portion 502 spreads cup 332. As a consequence, cup 332 exerts a force on elongate portion 502 and urges ball 331 to its neutral position (see FIG. 2).

Figure 58:
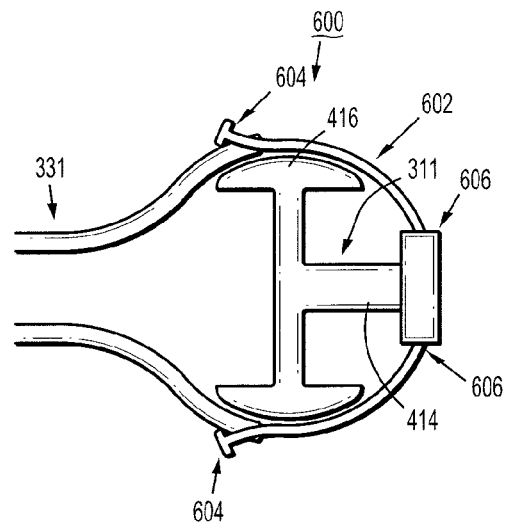
FIG. 58 is side cut-away view of an embodiment of a straightening mechanism with elastic bands for incorporation in any of the embodiments of the surgical devices discussed above.

With reference to FIG. 58, any of the embodiments of surgical device 100 may include a straightening mechanism 600 for returning articulating section 230 (FIG. 2) into longitudinal alignment with elongate outer tube 210 (FIG. 2) after articulation. Straightening mechanism 600 includes a plurality of elastic bands 602 configured to bias ball 331 to a neutral position (see FIG. 2). Each elastic band 602 has a proximal end 606 and a distal end 604. Proximal ends 606 of each elastic band 602 are attached to elongate portion 414 of articulation cable plate 311. Distal ends 604 of each elastic band are attached to a distal portion of ball 331. During operation, when ball 331 is moved relative to cup 332 (FIG. 21), at least one elastic bands 602 stretches and biases ball 331 toward its neutral position (see FIG. 2). It some embodiments, straightening mechanism 600 includes three elastic bands 602, but it is envisioned that straightening mechanism 600 may include more or fewer elastic bands 602.

Figure 59:
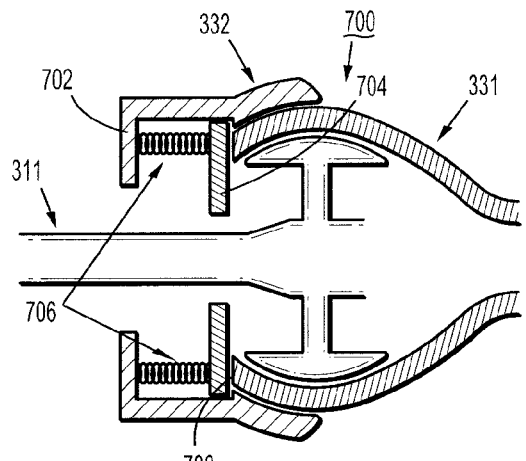
FIG. 59 is a side cross-sectional view of an embodiment of straightening mechanism with proximally-located springs for incorporation in any of the embodiments of the surgical device discussed above.

With reference to FIG. 59, any of the embodiments of surgical device 100 may include a straightening mechanism 700 for returning articulating section 230 (FIG. 2) into longitudinal alignment with elongate outer tube 210 (FIG. 2) after articulation. Straightening mechanism 700 includes an annular wall 702 extending radially and inwardly from an inner surface of cup 332 and a ring 704 positioned adjacent a proximal portion 708 of ball 331. Moreover, straightening mechanism 700 includes a plurality of springs 706 located between annular wall 702 and ring 704. Springs 706 are configured to bias ball 331 to its neutral position (see FIG. 2) upon movement of ball 331 with respect to cup 332. In operation, when ball 331 is moved relative to cup 332, some springs 706 compress, while other springs 706 stretch. The combined elongation and compression of springs 706 urges ball 331 back to its neutral position (see FIG. 2).

Figure 60:
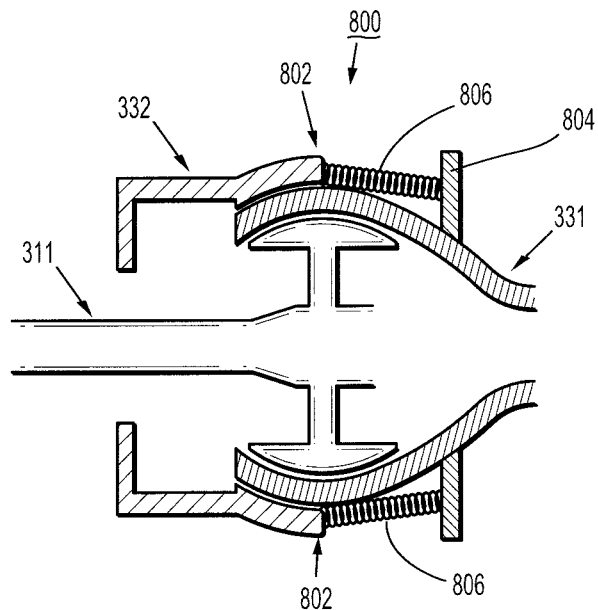
FIG. 60 is a side cross-sectional view of an embodiment of straightening mechanism with distally-located springs for incorporation in any of the embodiments of the surgical device discussed above.

With reference to FIG. 60, any of the embodiments of surgical device 100 may include a straightening mechanism 800 for returning articulating section 230 (FIG. 2) into longitudinal alignment with elongate outer tube 210 (FIG. 2) after articulation. Straightening mechanism 800 includes a ring 804 positioned distally of cup 332 and around a portion of ball 331. Moreover, straightening mechanism 800 includes a plurality of springs 806 located between ring 804 and a distal end 802 of cup 332. Springs 806 are configured to bias ball 331 to its neutral position (see FIG. 2) upon movement of ball 331 with respect to cup 332. In operation, when ball 331 is moved relative to cup 332, some springs 806 compress, while other springs 806 stretch. The combined elongation and compression of springs 806 urges ball 331 back to its neutral position (see FIG. 2).

Figure 61:
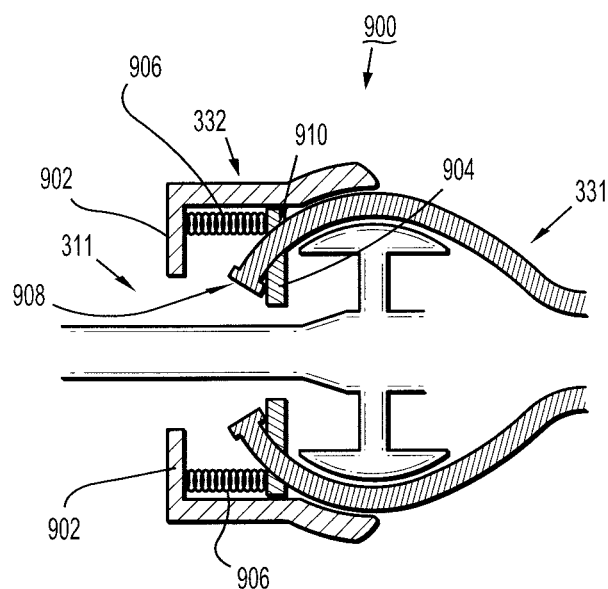
FIG. 61 is a side cross-sectional view of an embodiment of a straightening mechanism with a ring and springs for incorporation in any of the embodiments of the surgical device discussed above.

With reference to FIG. 61, any of the embodiments of surgical device 100 may include a straightening mechanism 900 for returning articulating section 230 (FIG. 2) into longitudinal alignment with elongate outer tube 210 (FIG. 2) after articulation. Straightening mechanism 900 includes an annular wall 902 extending radially and inwardly from an inner surface of cup 332 and a ring 904 positioned adjacent a proximal portion 908 of ball 331. Ring 904 defines an annular slot 910 configured to slidably receive proximal portion 908 of ball 331. Moreover, straightening mechanism 900 includes a plurality of springs 906 located between annular wall 902 and ring 904. Springs 906 are configured to bias ball 331 to its neutral position (see FIG. 2) upon movement of ball 331 with respect to cup 332. In operation, when ball 331 is moved relative to cup 332, springs 906 elongate, causing tension in springs 906. As a result of the tension, springs 906 urges ball 331 back to its neutral position (see FIG. 2).

It will be understood that various modifications may be made to the embodiments of the presently disclosed surgical device. Therefore, the above description should not be construed as limiting, but merely as exemplifications of embodiments. Those skilled in the art will envision other modifications within the scope and spirit of the present disclosure.

What is claimed is:

1. A surgical device for performing surgery, comprising:
a handle assembly including a cup portion;
an elongate member extending from the handle assembly, the elongate member having an articulating section and a straight section, wherein the articulating section is configured to articulate with respect to the straight section;
an articulation mechanism operatively associated with the handle assembly and the articulating section such that the articulating section articulates toward a first direction relative to the straight section upon movement of the handle assembly towards the first direction with respect to the straight section, the articulation mechanism including:
an articulation cable plate disposed at least partially within the cup portion, the articulation cable plate coupled with the articulating section of the elongate member; and
an articulation lock ring disposed within the cup portion of the handle assembly, the articulation lock ring having a plurality of circumferentially arranged fingers, the articulation cable plate movable between a locked position in which the plurality of fingers engage an inner surface of the cup portion to lock position of the handle assembly with respect to the elongate member and an unlocked position in which the plurality of fingers disengage from the inner surface of the cup portion, whereby the handle assembly is movable with respect to the elongate member;
an end effector operatively coupled to the articulating section of the elongate member, the end effector having first and second jaw members, wherein the first and second jaw members are configured to move relative to each other between an open position and an approximated position; and
a locking mechanism configured for fixing a relative position of first and second jaw members, the locking mechanism including a first ratchet assembly and a second ratchet assembly positioned within the handle assembly, the first and second ratchet assemblies being moveable relative to each other between an engaged position to lock the relative position of the first and second jaw members and a disengaged position to unlock the relative position of the first and second jaw members.

2. The surgical device of claim 1, wherein the articulating section includes a plurality of articulation links for facilitating articulation of articulating section relative to the straight section.

3. The surgical device of claim 2, wherein the articulation mechanism includes a plurality of articulation cables passing through the articulation links.

4. The surgical device of claim 3, wherein the plurality of articulation cables operatively connect the articulation cable plate with the articulating section, the plurality of articulation cables pulled proximally when the articulation cable plate is in the locked position.

5. The surgical device of claim 4, wherein the articulation mechanism further includes an articulation lock trigger operatively coupled with the articulation cable plate, the articulation lock trigger is configured to move the articulation cable plate between the locked position and the unlocked position.

6. The surgical device of claim 4, wherein the articulation cable plate includes an annular portion and an elongate portion, the annular portion disposed at least partially within the articulation lock ring, whereby the annular portion causes outward flexing of the plurality of fingers when the articulation cable plate is in the locked position.

7. The surgical device of claim 6, wherein the plurality of articulation cables are fixed securely to the annular portion of the articulation cable plate.

8. The surgical device of claim 1, wherein the handle assembly includes a thumb loop operatively connected to the end effector such that actuation of the thumb loop causes an actuation of the end effector.

9. The surgical device of claim 1, wherein the locking mechanism includes a release assembly configured to disengage the first ratchet assembly from the second ratchet assembly.

10. The surgical device of claim 9, wherein the locking mechanism includes a biasing member for biasing the release assembly in a distal direction.

11. The surgical device of claim 9, wherein the release assembly of the locking mechanism includes a trigger, the release assembly being configured to disengage the first ratchet assembly from the second ratchet assembly upon movement of the trigger in a proximal direction.

12. The surgical device of claim 1, wherein the second ratchet assembly is configured to move longitudinally along the handle assembly.

13. The surgical device of claim 1, wherein the end effector is configured to transmit electrosurgical energy to tissue.

14. The surgical device of claim 1 further comprising, a rotational wheel operatively coupled with the end effector, wherein rotation of the rotational wheel causes concomitant rotation of the end effector.

15. The surgical device of claim 14, wherein the rotational wheel is configured to be rotatable independent of the articulation mechanism.

16. The surgical device of claim 1, wherein the articulation cable plate is configured to urge the plurality of fingers radially outward when the articulation cable plate is in the locked position.

17. The surgical device of claim 1, wherein the fingers are made of resilient material.

18. A surgical device for performing surgery, comprising:
a handle assembly including a cup portion;
an elongate member extending from the handle assembly, the elongate member having an articulating section and a substantially stiff section, wherein the articulating section is configured to articulate with respect to the substantially stiff section;
an articulation mechanism operatively associated with the handle assembly and the articulating section, wherein moving the handle assembly in a first direction relative to the substantially stiff section causes the articulating section to articulate towards the first direction relative to the substantially stiff section, the articulation mechanism including:
an articulation cable plate disposed at least partially within the cup portion, the articulation cable plate coupled with the articulating section of the elongate member; and
an articulation lock ring disposed within the cup portion of the handle assembly, the articulation lock ring having a plurality of circumferentially arranged fingers, the articulation cable plate movable between a locked position in which the plurality of fingers engage an inner surface of the cup portion to lock position of the handle assembly with respect to the elongate member and an unlocked position in which the plurality of fingers disengage from the inner surface of the cup portion, whereby the handle assembly is movable with respect to the elongate member;
an end effector operatively coupled to the articulating section of the elongate member, the end effector having first and second jaw members, wherein the first and second jaw members are configured to move relative to each other between an open position and an approximated position; and
a locking mechanism configured for fixing a relative position of first and second jaw members, the locking mechanism including a first ratchet assembly and a second ratchet assembly positioned within the handle assembly, the first and second ratchet assemblies being moveable relative to each other between an engaged position to lock the relative position of the first and second jaw members and a disengaged position to unlock the relative position of the first and second jaw members.

19. The surgical device of claim 18, wherein the articulating section includes a plurality of articulation links for facilitating articulation of articulating section relative to the substantially stiff section.

20. The surgical device of claim 19, wherein the articulation mechanism includes a plurality of articulation cables passing through the articulation links.

21. The surgical device of claim 18, wherein the handle assembly includes a thumb loop operatively connected to the end effector such that actuation of the thumb loop causes an actuation of the end effector.

22. The surgical device of claim 18, wherein the locking mechanism includes a release assembly configured to disengage the first ratchet assembly from the second ratchet assembly.

23. The surgical device of claim 22, wherein the locking mechanism includes a biasing member for biasing the release assembly in a distal direction.

24. The surgical device of claim 22, wherein the release assembly of the locking mechanism includes a trigger, the release assembly being configured to disengage the first ratchet assembly from the second ratchet assembly upon movement of the trigger in a proximal direction.

25. The surgical device of claim 24 wherein the second ratchet assembly is configured to move longitudinally along the handle assembly.

26. The surgical device of claim 18, wherein the end effector is configured to transmit electrosurgical energy to tissue.

27. A surgical device for performing surgery, comprising:
a handle assembly including a cup portion;
an elongate member extending from the handle assembly, the elongate member having an articulating section and a substantially straight section, the articulating section configured to articulate with respect to the substantially straight section;

an articulation mechanism operatively associated with the handle assembly and the articulating section, the articulation mechanism including:
  an articulation cable plate movable at least partially within the cup portion and operable to effect articulation of the articulating section of the elongate member; and
  an articulation lock ring operable with the articulation cable plate, the articulation cable plate selectively movable to engage the articulation lock ring which, in turn, causes the articulation lock ring to engage the cup portion to maintain a relative position of the articulating section with respect to the substantially straight section;

an end effector operably coupled to the articulating section of the elongate member, the end effector having first and second jaw members movable relative to each other between an open position and an approximated position; and a locking mechanism configured for fixing a relative position of the first and second jaw members.

28. The surgical device of claim 27, wherein the articulation lock ring includes a plurality of radially spaced fingers.

29. The surgical device of claim 28, wherein the plurality of radially spaced fingers is configured to frictionally engage the cup portion.

30. The surgical device of claim 27, wherein the handle assembly is movable with respect to the straight portion.

31. The surgical device of claim 30, wherein the articulation lock ring is operable to maintain the handle assembly in a position relative to the substantially straight portion.

32. The surgical device of claim 27, wherein the articulation lock ring surrounds at least a portion of the articulation lock plate.

* * * * *